US005695964A

United States Patent [19]

Nii et al.

[11] Patent Number: 5,695,964
[45] Date of Patent: *Dec. 9, 1997

[54] RECOMBINANT DNA VECTORS, INCLUDING PLASMIDS, AND HOST CELLS FOR PRODUCTION OF TRUNCATED THROMBOMODULIN

[75] Inventors: Atsushi Nii; Hideaki Morishita; Akio Uemura; Ei Mochida, all of Tokyo, Japan

[73] Assignee: Mochida Pharmaceutical Co., Ltd., Tokyo, Japan

[*] Notice: The term of this patent shall not extend beyond the expiration date of Pat. No. 5,516,659.

[21] Appl. No.: 587,389

[22] Filed: Jan. 17, 1996

Related U.S. Application Data

[62] Division of Ser. No. 307,444, Sep. 19, 1994, Pat. No. 5,516,659, which is a continuation of Ser. No. 835,436, Mar. 27, 1992, abandoned.

[30] Foreign Application Priority Data

Jun. 27, 1990 [JP] Japan .................. Hei 2-168766

[51] Int. Cl.$^6$ .................. C12N 15/12; C12N 15/63; C12N 15/85
[52] U.S. Cl. .................. 435/69.6; 435/243; 435/320.1; 435/325; 435/358
[58] Field of Search .................. 435/69.1, 69.6, 435/70.1, 240.1, 252.3, 320.1, 243, 325, 358; 536/23.1, 23.5; 530/350, 395

[56] References Cited

U.S. PATENT DOCUMENTS

| | | | |
|---|---|---|---|
| 4,912,207 | 3/1990 | Majerus et al. | 536/23.51 |
| 5,047,503 | 9/1991 | Aoki et al. | 530/350 |
| 5,202,421 | 4/1993 | Kunihiro et al. | 530/350 |
| 5,256,770 | 10/1993 | Glaser et al. | 530/381 |
| 5,273,962 | 12/1993 | Doi et al. | 514/8 |
| 5,300,490 | 4/1994 | Kunihiro et al. | 514/8 |

FOREIGN PATENT DOCUMENTS

| | | |
|---|---|---|
| A-0 155 852 | 3/1985 | European Pat. Off. . |
| A-0 230 945 | 1/1987 | European Pat. Off. . |
| A-0 312 598 | 1/1988 | European Pat. Off. . |
| A-0 290 419 | 5/1988 | European Pat. Off. . |
| A-0 376 251 | 12/1989 | European Pat. Off. . |
| 60-199819 | 10/1985 | Japan . |
| 63-30423 | 2/1988 | Japan . |
| 63-146898 | 6/1988 | Japan . |
| 63-301791 | 12/1988 | Japan . |
| 2-19399 | 1/1990 | Japan . |
| WO 88/09811 | 12/1988 | WIPO . |

OTHER PUBLICATIONS

R.W. Jackman, et al., "Human Thrombomodulin Gene is Intron Depleted: Nucleic Acid Sequences of the cDNA and Gene Predict Protein Structure and Suggest Sites of Regulatory Control", *Proc. Natl. Acad. Sci. USA*, vol. 84, pp. 6425–6429, 1987.

D. Wen, et al., "Human Thrombomodulin: Complete cDNA Sequence and Chromosome Localization of the Gene", *Biochemistry*, vol. 26, pp. 4350–4357, 1987.

K. Suzuki, et al., "Structure and Expression of Human Thrombomodulin, a Thrombin Receptor on Endothelium Acting as a Cofactor for Protein C Activation", *The EMBO Journal*, vol. 6, No. 7, pp. 1891–1897, 1987.

N.L. Esmon, et al., "Isolation of a Membrane–Bound for Thrombin–Catalyzed Activation of Protein C", *The Journal of Bio. Chem.*, vol. 257, No. 2, pp. 859–864, 1982.

I. Maruyama, et al., "Human Thrombomodulin is not an Efficient Inhibitor of the Procoagulant Activity of Thrombin", *J. Clin. Invest.*, vol. 75, pp. 987–991, 1985.

H.H. Salem, et al., "Isolation and Characterization of Thrombomodulin from Human Placenta" *The Journal Of Bio. Chem.*, vol. 259, No. 19, pp. 12246–12251, 1984.

S. Kurosawa, et al., "Preparation of Thrombomodulin from Human Placenta" *Thrombosis Research*, vol. 37, pp. 353–364, 1985.

K. Suzuki, et al., "Functionally Active Thrombomodulin is Present in Human Platelets", *The Journal of Bio. Chem.*, vol. 104, pp. 628–632, 1988.

H. Ishii, et al., "Thrombomodulin is Present in Human Plasma and Urine", *J. Clin. Invest.*, vol. 76, pp. 2178–2181, 1985.

H. Ishii, et al., "The Property of Plasma and Urinary Thrombomodulin", 108th Yakugakkai Abstract 6F05, 11–1, 1988 (with English translation).

S. Kurosawa, et al., "A 10–kDa Cyanogen Bromide Fragment from the Epidermal, Growth Factor Homology Domain of Rabbit Thrombomodulin Contains the Primary Thrombin Binding Site", *The Journal of Bio. Chem.*, vol. 263, No. 13, pp. 5993–5996, 1988.

K. Suzuki, et al., "A Domain Composed of Epidermal Growth Factor–Like Structures of Human Thrombomodulin is Essential for Thrombin Binding and for Protein C Activation", *The Journal of Bio. Chem.*, vol. 264, No. 9, pp. 4872–4876, 1989.

M. Zushi, et al., "The Last Three Consecutive Epidermal Growth Factor–Like Structures of Human Thrombomodulin Comprise the Minimum Functional Domain for Protein C–Activating Cofactor Activity and Anticoagulant Activity", *The Journal of Bio. Chem.*, vol. 264, No. 18, pp. 10351–10353, 1989.

(List continued on next page.)

*Primary Examiner*—Vasu S. Jagannathan
*Assistant Examiner*—Christine Saoud
*Attorney, Agent, or Firm*—Oliff & Berridge

[57] ABSTRACT

This invention relates to novel vectors and host cells containing nucleic acids coding for a polypeptide having thrombin binding ability, anticoagulant activity and thrombolytic activity. The polypeptide can be efficiently produced in large quantities by means of genetic recombination techniques using the vectors and host cells of the present invention. Since the polypeptide exhibits anticoagulant activity and thrombolytic activity without generating side effects such as bleeding tendencies, it can be applied effectively to the prevention and treatment of hypercoagulability-related diseases.

15 Claims, 32 Drawing Sheets

OTHER PUBLICATIONS

K. Gomi, et al., "Abstracts", *Thrombosis and Haeomostasis.*, vol. 62, pp. 334, 1039, 1989.

J.F. Parkinson, et al., "Stable Expression of a Secretable Deletion Mutant of Recombinant Human Thrombomodulin in Mammalian Cells", *The Journal of Bio. Chem.*, vol. 265, No. 21, pp. 12602–12610, 1990.

H. Land, et al., "5'-Terminal Sequences of Eucaryotic mRNA can be Cloned with High Efficiency", *Nucleic Acids Res.*, vol. 9, No. 10, pp. 2251–2266, 1981.

H. Okayama, et al., "High-Efficiency Cloning of Full-Length cDNA", *Mol. Cell. Bio.*, vol. 2, pp. 161–170, 1982.

U. Gubler, et al., "A Simple and Very Efficient Method for Generating cDNA Libraries", *Gene*, vol. 25, pp. 263–269, 1983.

R.B. Wallace, et al., "The Use of Synthetic Oligonucleotides as Hybridization Probes. II. Hybridization of Oligonucleotides of Mixed Sequence to Rabbit β-Globin DNA", *Nucleic Acids Res.*, vol. 9, pp. 879–894, 1981.

W. Kramer, et al., "The Gapped Duplex DNA Approach to Oligonucleotide–Directed Mutation Construction", *Nucleic Acids Res.*, vol. 12, pp. 9441–9456, 1984.

W. Kramer, et al., "Oligonucleotide–Directed Construction of Mutations via Gapped Duplex DNA", *Methods in Enzymology*, vol. 154, pp. 350–367, 1987.

K. O'Hare, et al., "Transformation of Mouse Fibroblasts to Methotrexate Resistance by a Recombinant Plasmid Expressing a Prokaryotic Dihydrofolate Reductase", *Proc. Natl. Acad. Sci. USA*, vol. 78, No. 3, pp. 1527–1531, 1981.

T. Kanamori, et al., "Expression and Excretion of Human Pancreatic Secretory Trypsin Inhibitor in Lipoprotein–Deletion Mutant of *Escherichia coli*", *Gene*, vol. 66, pp. 295–300, 1988.

P. Gunning, et al., "A Human β–Actin Expression Vector System Directs High–Level Accumulation of Antisense Transcripts", *Proc. Natl. Acad. Sci. USA*, vol. 84, pp. 4831–4835, 1987.

R.J. Kaufman, et al., "Construction of a Modular Dihydrofolate Reductase cDNA Gene: Analysis of Signals Utilized for Efficient Expression", *Mol. Cell. Biol.*, vol. 2, pp. 1304–1319, 1982.

Y. Takebe, et al., "SRa Promotor: an Efficient and Versatile Mammalian cDNA Expression System Composed of the Simian Virus 40 Early Promotor and the R–U5 Segment of Human T–Cell Leukemia Virus Type 1 Long Terminal Repeat", *Mol. Cell. Biol.*, vol. 8, pp. 466–472, 1988.

L.M. Sompayrac, et al., "Efficient Infection of Monkey Cells with DNA of Simian Virus 40", *Proc. Natl. Acad. Sci. USA*, vol. 78, No. 12, pp. 7575–7578, 1981.

C.H.W. Hirs, "Reduction and S–Carboxymethylation of Proteins", *Methods in Enzymology*, vol. 11, pp. 199–203, 1967.

D. Zerbib, et al., "Electric Field Mediated Transformation: Isolation and Characterization of a $TK^+$ Subclone", *Biochem. Biophys. Res. Comm.*, vol. 129, pp. 611–618, 1985.

S. Yokoyama, et al., "Action of Crystalline Acid Carboxypeptidase from Penicillium Janthinellum", *Biochem. Biophys. Acta*, vol. 397, pp. 443–448, 1975.

G. Urlaub, et al., "Isolation of Chinese Hamster Cell Mutants Deficient in Dihydrofolate Reductase Activity", *Proc. Natl. Acad. Sci. USA*, vol. 77, pp. 4216–4220, 1980.

Shirai et al., "Gene Structure of Human Thrombomodulin . . .", *J. Biochem.* 103: 281–285 (1988).

Sambrook, *Molecular Cloning*, p. 16.3 (1989).

Yamamoto et al., "Antithrombotic Properties of Recombinant Human Thrombomodulin", *Thromb. Haem.* 62(1):334, abstract #1040 (Aug. 1989).

```
GCTTTCCCCG GCGCCTGCAC GCGGCGCGCC TGGGTAAC ATG         41
                                                Met

CTT GGG GTC CTG GTC CTT GGC GCG CTG GCC CTG           74
Leu Gly Val Leu Val Leu Gly Ala Leu Ala Leu
            -15             -10

GCC GGC CTG GGG TTC CCC GCA    CCC GCA GAG CCG       107
Ala Gly Leu Gly Phe Pro Ala    Pro Ala Glu Pro
     -5                 -1  1                 5

CAG CCG GGT GGC AGC CAG TGC GTC GAG CAC GAC          140
Gln Pro Gly Gly Ser Gln Cys Val Glu His Asp
                     10              15

TGC TTC GCG CTC TAC CCG GGC CCC GCG ACC TTC          173
Cys Phe Ala Leu Tyr Pro Gly Pro Ala Thr Phe
                 20                  25
```

FIG. 3(a)

```
CTC AAT GCC AGT CAG ATC TGC GAC GGA CTG CGG        206
Leu Asn Ala Ser Gln Ile Cys Asp Gly Leu Arg
        30                  35

GGC CAC CTA ATG ACA GTG CGC TCC TCG GTG GCT        239
Gly His Leu Met Thr Val Arg Ser Ser Val Ala
        40                  45

GCC GAT GTC ATT TCC TTG CTA CTG AAC GGC GAC        272
Ala Asp Val Ile Ser Leu Leu Leu Asn Gly Asp
 50              55                  60

GGC GGC GTT GGC CGC CGG CGC CTC TGG ATC GGC        305
Gly Gly Val Gly Arg Arg Arg Leu Trp Ile Gly
                65                  70

CTG CAG CTG CCA CCC GGC TGC GGC GAC CCC AAG        338
Leu Gln Leu Pro Pro Gly Cys Gly Asp Pro Lys
        75                  80
```

FIG. 3(b)

```
CGC CTC GGG CCC CTG CGC GGC TTC CAG TGG GTT        371
Arg Leu Gly Pro Leu Arg Gly Phe Gln Trp Val
        85                  90

ACG GGA GAC AAC AAC ACC AGC TAT AGC AGG TGG        404
Thr Gly Asp Asn Asn Thr Ser Tyr Ser Arg Trp
    95                  100

GCA CGG CTC GAC CTC AAT GGG GCT CCC CTC TGC        437
Ala Arg Leu Asp Leu Asn Gly Ala Pro Leu Cys
105                 110                 115

GGC CCG TTG TGC GTC GCT GTC TCC GCT GCT GAG        470
Gly Pro Leu Cys Val Ala Val Ser Ala Ala Glu
                        120         125

GCC ACT GTG CCC AGC GAG CCG ATC TGG GAG GAG        503
Ala Thr Val Pro Ser Glu Pro Ile Trp Glu Glu
            130                 135
```

FIG. 3(c)

```
CAG CAG TGC GAA GTG AAG GCC GAT GGC TTC CTC         536
Gln Gln Cys Glu Val Lys Ala Asp Gly Phe Leu
        140                 145

TGC GAG TTC CAC TTC CCA GCC ACC TGC AGG CCA         569
Cys Glu Phe His Phe Pro Ala Thr Cys Arg Pro
        150                 155

CTG GCT GTG GAG CCC GGC GCC GCG GCT GCC GCC         602
Leu Ala Val Glu Pro Gly Ala Ala Ala Ala Ala
160                 165                 170

GTC TCG ATC ACC TAC GGC ACC CCG TTC GCG GCC         635
Val Ser Ile Thr Tyr Gly Thr Pro Phe Ala Ala
                175                 180

CGC GGA GCG GAC TTC CAG GCG CTG CCG GTG GGC         668
Arg Gly Ala Asp Phe Gln Ala Leu Pro Val Gly
                185                 190
```

FIG. 3(d)

```
AGC TCC GCC GCG GTG GCT CCC CTC GGC TTA CAG        701
Ser Ser Ala Ala Val Ala Pro Leu Gly Leu Gln
        195                 200

CTA ATG TGC ACC GCG CCG CCC GGA GCG GTC CAG        734
Leu Met Cys Thr Ala Pro Pro Gly Ala Val Gln
        205                 210

GGG CAC TGG GCC AGG GAG GCG CCG GGC GCT TGG        767
Gly His Trp Ala Arg Glu Ala Pro Gly Ala Trp
215                 220                 225

GAC TGC AGC GTG GAG AAC GGC GGC TGC GAG CAC        800
Asp Cys Ser Val Glu Asn Gly Gly Cys Glu His
                230                 235

GCG TGC AAT GCG ATC CCT GGG GCT CCC CGC TGC        833
Ala Cys Asn Ala Ile Pro Gly Ala Pro Arg Cys
                240                 245
```

FIG. 3(e)

```
CAG TGC CCA GCC GGC GCC GCC CTG CAG GCA GAC        866
Gln Cys Pro Ala Gly Ala Ala Leu Gln Ala Asp
        250                 255

GGG CGC TCC TGC ACC GCA TCC GCG ACG CAG TCC        899
Gly Arg Ser Cys Thr Ala Ser Ala Thr Gln Ser
        260                 265

TGC AAC GAC CTC TGC GAG CAC TTC TGC GTT CCC        932
Cys Asn Asp Leu Cys Glu His Phe Cys Val Pro
270                 275                 280

AAC CCC GAC CAG CCG GGC TCC TAC TCG TGC ATG        965
Asn Pro Asp Gln Pro Gly Ser Tyr Ser Cys Met
                285                 290

TGC GAG ACC GGC TAC CGG CTG GCG GCC GAC CAA        998
Cys Glu Thr Gly Tyr Arg Leu Ala Ala Asp Gln
        295                 300
```

FIG. 3(f)

```
CAC CGG TGC GAG GAC GTG GAT GAC TGC ATA CTG              1031
His Arg Cys Glu Asp Val Asp Asp Cys Ile Leu
        305                 310

GAG CCC AGT CCG TGT CCG CAG CGC TGT GTC AAC              1064
Glu Pro Ser Pro Cys Pro Gln Arg Cys Val Asn
        315                 320

ACA CAG GGT GGC TTC GAG TGC CAC TGC TAC CCT              1097
Thr Gln Gly Gly Phe Glu Cys His Cys Tyr Pro
325                 330                 335

AAC TAC GAC CTG GTG GAC GGC GAG TGT GTG GAG              1130
Asn Tyr Asp Leu Val Asp Gly Glu Cys Val Glu
                    340                 345

CCC GTG GAC CCG TGC TTC AGA GCC AAC TGC GAG              1163
Pro Val Asp Pro Cys Phe Arg Ala Asn Cys Glu
                350                 355
```

FIG. 3(g)

```
TAG CAG TGC CAG CCC CTG AAC CAA ACT AGC TAC        1196
Tyr Gln Cys Gln Pro Leu Asn Gln Thr Ser Tyr
        360                 365

CTC TGC GTC TGC GCC GAG GGC TTC GCG CCC ATT        1229
Leu Cys Val Cys Ala Glu Gly Phe Ala Pro Ile
        370                 375

CCC CAC GAG CCG CAC AGG TGC CAG ATG TTT TGC        1262
Pro His Glu Pro His Arg Cys Gln Met Phe Cys
380                 385                 390

AAC CAG ACT GCC TGT CCA GCC GAC TGC GAC CCC        1295
Asn Gln Thr Ala Cys Pro Ala Asp Cys Asp Pro
                    395                 400

AAC ACC CAG GCT AGC TGT GAG TGC CCT GAA GGC        1328
Asn Thr Gln Ala Ser Cys Glu Cys Pro Glu Gly
        405                 410
```

FIG. 3(h)

```
TAC ATC CTG GAC GAC GGT TTC ATC TGC ACG GAC    1361
Tyr Ile Leu Asp Asp Gly Phe Ile Cys Thr Asp
        415                 420

ATC GAC GAG TGC GAA AAC GGC GGC TTC TGC TCC    1394
Ile Asp Glu Cys Glu Asn Gly Gly Phe Cys Ser
        425                 430

GGG GTG TGC CAC AAC CTC CCC GGT ACC TTC GAG    1427
Gly Val Cys His Asn Leu Pro Gly Thr Phe Glu
435                 440                 445

TGC ATC TGC GGG CCC GAC TCG GCC CTT GCC CGC    1460
Cys Ile Cys Gly Pro Asp Ser Ala Leu Ala Arg
        450                 455

CAC ATT GGC ACC GAC TGT GAC TCC GGC AAG GTG    1493
His Ile Gly Thr Asp Cys Asp Ser Gly Lys Val
        460                 465
```

FIG. 3(i)

```
GAC GGT GGC GAC AGC GGC TCT GGC GAG CCC CCG         1526
Asp Gly Gly Asp Ser Gly Ser Gly Glu Pro Pro
            470                 475

CCC AGC CCG ACG CCC GGC TCC ACC TTG ACT CCT         1559
Pro Ser Pro Thr Pro Gly Ser Thr Leu Thr Pro
        480                 485

CCG GCC GTG GGG CTC GTG CAT TCG GGC TTG CTC         1592
Pro Ala Val Gly Leu Val His Ser Gly Leu Leu
490                 495                 500

ATA GGC ATC TCC ATC GCG AGC CTG TGC CTG GTG         1625
Ile Gly Ile Ser Ile Ala Ser Leu Cys Leu Val
                505                 510

GTG GCG CTT TTG GCG CTC CTC TGC CAC CTG CGC         1658
Val Ala Leu Leu Ala Leu Leu Cys His Leu Arg
            515                 520
```

FIG. 3(j)

```
AAG AAG CAG GGC GCC GCC AGG GCC AAG ATG GAG      1691
Lys Lys Gln Gly Ala Ala Arg Ala Lys Met Glu
        525                 530

TAC AAG TGC GCG GCC CCT TCC AAG GAG GTA GTG      1724
Tyr Lys Cys Ala Ala Pro Ser Lys Glu Val Val
        535                 540

CTG CAG CAC GTG CGG ACC GAG CGG ACG CCG CAG      1757
Leu Gln His Val Arg Thr Glu Arg Thr Pro Gln
545                 550                 555

AGA  CTC  TGA  GCGG  CCTCCGTCCA  GGAGCCTGGC      1790
Arg  Leu  ***

TCCGTCCAGG  AGCCTGTGCC  TCCTCACCCC  CAGCTTTGCT   1830

ACCAAAGCAC  CTTAGCTGGC  ATTACAGCTG  GAGAAGACCC   1870

TCCCCGCACC  CCCCAAGCTG  TTTTCTTCTA  TTCCATGGCT   1910
```

FIG. 3(k)

```
AACTGGCGAG GGGGTGATTA GAGGGAGGAG AATGAGCCTC        1950

GGCCTCTTCC GTGACGTCAC TGGACCACTG GGCAATGATG        1990

GCAATTTTGT AACGAAGACA CAGACTGCGA TTTGTCCCAG        2030

GTCCTCACTA CCGGGCGCAG GAGGGTGAGC GTTATTGGTC        2070

GGCAGCCTTC TGGGCAGACC TTGACCTCGT GGGCTAGGGA        2110

TGACTAAAAT ATTTATTTTT TTTAAGTATT TAGGTTTTTG        2150

TTTGTTTCCT TTGTTCTTAC CTGTATGTCT CCAGTATCCA        2190

CTTTGCACAG CTCTCCGGTC TCTCTCTCTC TACAAACTCC        2230

CACTTGTCAT GTGACAGGTA AACTATCTTG GTGAATTTTT        2270

TTTTCCTAGC CCTCTCACAT TTATGAAGCA AGCCCCACTT        2310

ATTCCCCATT CTTCCTAGTT TTCTCCTCCC AGGAACTGGG        2350
```

FIG. 3(1)

```
CCAACTCACC TGAGTCACCC TACCTGTGCC TGACCCTACT              2390

TCTTTTGCTC TTAGCTGTCT GCTCAGACAG AACCCCTACA              2430

TGAAACAGAA ACAAAAACAC TAAAAATAAA AAT                     2463
```

FIG. 3(m)

pKCR-TM-Ala

Oligonucleotides for pKCR-TM-Ala construction

| | | |
|---|---|---|
| 49 mer | CTTCGAGTGC ATCTGCGGGC CCGACTCGGC | 30 |
| | CCTTGCCCGC TAGGATCCC | 49 |
| 53 mer | GGGATCCTAG CGGGCAAGGG CCGAGTCGGG | 30 |
| | CCCGCAGATG CACTCGAAGG TAC | 53 | pKCR-TM-Val

Oligonucleotides for pKCR-TM-Val construction

| | | |
|---|---|---|
| 49 mer | CTTCGAGTGC ATCTGCGGGC CCGACTCGGC | 30 |
| | CCTTGTCCGC TAGGATCCC | 49 |
| 53 mer | GGGATCCTAG CGGACAAGGG CCGAGTCGGG | 30 |
| | CCCGCAGATG CACTCGAAGG TAC | 53 |

FIG. 5(a)

pM450-TM-Ala     pM450-TM-Val:
Oligonucleotides for pM450-TM-Ala and pM450-TM-Val constructions

| | | | |
|---|---|---|---|
| 69 mer | TATGGGACCA GCAGAACCAC AACCAGGTGG | 30 |
| | AAGTCAATGT GTAGAACATG ATTGTTTTGC | 60 |
| | ACTATATCC | 69 |
| 67 mer | GGATATAGTG CAAAACAATC ATGTTCTACA | 30 |
| | CATTGACTTC CACCTGGTTG TGGTTCTGCT | 60 |
| | GGTGCCA | 67 |

FIG. 5(b)

| | | |
|---|---|---|
| S1 | TT<u>GTCGAC</u>AT GCTTGGGGTC CTGGTCCTT<br>Sal I | 29 |
| S2 | AT<u>AAGCTT</u>CC GCTGCTGAGG CCACTGTGC<br>Hind III | 29 |
| S3 | TT<u>CTGCAG</u>CT <u>CGAG</u>CCCGTG GACCCGTGCT TC<br>Pst I  Xho I | 32 |
| A1 | TT<u>GGATCC</u>CA CAGTGGCCTC AGCAGCGGA<br>BamH I | 29 |
| A2 | AT<u>GTCGAC</u>AC ACTCGCCGTC CACCAGGTC<br>Sal I | 29 |
| A3 | GC<u>GAATTC</u>GG <u>ATCC</u>TCAGC GGGCAAGGCC GAGTCGGG<br>EcoR I  BamH I | 38 |

FIG. 7

| | | | | |
|---|---|---|---|---|
| ATGCTTGGGG | TCCTGGTCCT | TGGCGCGCTG | GCCCTGGCCG | 40 |
| GCCTGGGGTT | CCCCGCTCCC | GCAGAGCCGC | AGCCGGGTGG | 80 |
| CAGCCAGTGC | GTCGAGCACG | ACTGCTTCGC | GCTCTACCCG | 120 |
| GGCCCCGCGA | CCTTCCTCAA | TGCCAGTCAG | ATCTGCGACG | 160 |
| GACTGCGGGG | CCACCTAATG | ACAGTGCGCT | CCTCGGTGGC | 200 |
| TGCCGATGTC | ATTTCCTTGC | TACTGAACGG | CGACGGCGGC | 240 |
| GTTGGCCGCC | GGCGCCTCTG | GATCGGCCTG | CAGCTGCCAC | 280 |
| CCGGCTGCGG | CGACCCCAAG | CGCCTCGGGC | CCCTGCGCGG | 320 |
| CTTCCAGTGG | GTTACGGGAG | ACAACAACAC | CAGCTATAGC | 360 |
| AGGTGGGCAC | GGCTCGACCT | CAATGGGGCT | CCCCTCTGCG | 400 |
| GCCCGTTGTG | CGTCGCTGTC | TCCGCTGCTG | AGGCCACTGT | 440 |
| GCCCAGCGAG | CCGATCTGGG | AGGAGCAGCA | GTGCGAAGTG | 480 |
| AAGGCCGATG | GCTTCCTCTG | CGAGTTCCAC | TTCCCAGCCA | 520 |
| CCTGCAGGCC | ACTGGCTGTG | GAGCCCGGCG | CCGCGGCTGC | 560 |
| CGCCGTCTCG | ATCACCTACG | GCACCCCGTT | CGCGGCCCGC | 600 |
| GGAGCGGACT | TCCAGGCGCT | GCCGGTGGGC | AGCTCCGCCG | 640 |
| CGGTGGCTCC | CCTCGGCTTA | CAGCTAATGT | GCACCGCGCC | 680 |
| GCCCGGAGCG | GTCCAGGGGC | ACTGGGCCAG | GGAGGCGCCG | 720 |
| GGCGCTTGGG | ACTGCAGCGT | GGAGAACGGC | GGCTGCGAGC | 760 |
| ACGCGTGCAA | TGCGATCCCT | GGGGCTCCCC | GCTGCCAGTG | 800 |
| CCCAGCCGGC | GCCGCCCTGC | AGGCAGACGG | GCGCTCCTGC | 840 |

FIG. 9(a)

| | | | | |
|---|---|---|---|---|
| ACCGCATCCG | CGACGCAGTC | CTGCAACGAC | CTCTGCGAGC | 880 |
| ACTTCTGCGT | TCCCAACCCC | GACCAGCCGG | GCTCCTACTC | 920 |
| GTGCATGTGC | GAGACCGGCT | ACCGGCTGGC | GGCCGACCAA | 960 |
| CACCGGTGCG | AGGACGTGGA | TGACTGCATA | CTGGAGCCCA | 1000 |
| GTCCGTGTCC | GCAGCGCTGT | GTCAACACAC | AGGGTGGCTT | 1040 |
| CGAGTGCCAC | TGCTACCCTA | ACTACGACCT | GGTGGACGGC | 1080 |
| GAGTGTGTCG | AGCCCGTGGA | CCCGTGCTTC | AGAGCCAACT | 1120 |
| GCGAGTACCA | GTGCCAGCCC | CTGAACCAAA | CTAGCTACCT | 1160 |
| CTGCGTCTGC | GCCGAGGGCT | TCGCGCCCAT | TCCCCACGAG | 1200 |
| CCGCACAGGT | GCCAGATGTT | TTGCAACCAG | ACTGCCTGTC | 1240 |
| CAGCCGACTG | CGACCCCAAC | ACCCAGGCTA | GCTGTGAGTG | 1280 |
| CCCTGAAGGC | TACATCCTGG | ACGACGGTTT | CATCTGCACG | 1320 |
| GACATCGACG | AGTGCGAAAA | CGGCGGCTTC | TGCTCCGGGG | 1360 |
| TGTGCCACAA | CCTCCCCGGT | ACCTTCGAGT | GCATCTGCGG | 1400 |
| GCCCGACTCG | GCCCTTGCCC | GCTCA | | 1425 |

FIG. 9(b)

(A) DEL10
    oligonucleotides for DEL10 construction

D5-16U    CTTCGAGTGC TGATAG    16

D5-24L    AATTCTATCA GCACTCGAAG GTAC    24

(B) DEL49
    oligonucleotides for DEL49 construction

D10-14U    CTAGCTGTTG ATAG    14

D10-14L    AATTCTATCA ACAG    14

FIG. 12

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
   ( A ) LENGTH: 475 amino acids
   ( B ) TYPE: amino acid
   ( C ) STRANDEDNESS: single
   ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:1:

```
Met Leu Gly Val Leu Val Leu Gly Ala Leu Ala Leu Ala Gly Leu Gly
 1               5                  10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350
```

```
Pro  Asn  Tyr  Asp  Leu  Val  Asp  Gly  Glu  Cys  Val  Glu  Pro  Val  Asp  Pro
          355                      360                     365

Cys  Phe  Arg  Ala  Asn  Cys  Glu  Tyr  Gln  Cys  Gln  Pro  Leu  Asn  Gln  Thr
          370                      375                     380

Ser  Tyr  Leu  Cys  Val  Cys  Ala  Glu  Gly  Phe  Ala  Pro  Ile  Pro  His  Glu
385                           390                     395                     400

Pro  His  Arg  Cys  Gln  Met  Phe  Cys  Asn  Gln  Thr  Ala  Cys  Pro  Ala  Asp
                    405                     410                     415

Cys  Asp  Pro  Asn  Thr  Gln  Ala  Ser  Cys  Glu  Cys  Pro  Glu  Gly  Tyr  Ile
               420                      425                     430

Leu  Asp  Asp  Gly  Phe  Ile  Cys  Thr  Asp  Ile  Asp  Glu  Cys  Glu  Asn  Gly
          435                      440                     445

Gly  Phe  Cys  Ser  Gly  Val  Cys  His  Asn  Leu  Pro  Gly  Thr  Phe  Glu  Cys
     450                      455                     460

Ile  Cys  Gly  Pro  Asp  Ser  Ala  Leu  Val  Arg  His
465                 470                     475
```

( 2 ) INFORMATION FOR SEQ ID NO:2:

( i ) SEQUENCE CHARACTERISTICS:
        ( A ) LENGTH: 475 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:2:

```
Met  Leu  Gly  Val  Leu  Val  Leu  Gly  Ala  Leu  Ala  Leu  Ala  Gly  Leu  Gly
1                   5                        10                      15

Phe  Pro  Ala  Pro  Ala  Glu  Pro  Gln  Pro  Gly  Gly  Ser  Gln  Cys  Val  Glu
               20                       25                      30

His  Asp  Cys  Phe  Ala  Leu  Tyr  Pro  Gly  Pro  Ala  Thr  Phe  Leu  Asn  Ala
          35                       40                      45

Ser  Gln  Ile  Cys  Asp  Gly  Leu  Arg  Gly  His  Leu  Met  Thr  Val  Arg  Ser
     50                       55                      60

Ser  Val  Ala  Ala  Asp  Val  Ile  Ser  Leu  Leu  Leu  Asn  Gly  Asp  Gly  Gly
65                       70                      75                      80

Val  Gly  Arg  Arg  Arg  Leu  Trp  Ile  Gly  Leu  Gln  Leu  Pro  Pro  Gly  Cys
                    85                       90                      95

Gly  Asp  Pro  Lys  Arg  Leu  Gly  Pro  Leu  Arg  Gly  Phe  Gln  Trp  Val  Thr
               100                      105                     110

Gly  Asp  Asn  Asn  Thr  Ser  Tyr  Ser  Arg  Trp  Ala  Arg  Leu  Asp  Leu  Asn
          115                      120                     125

Gly  Ala  Pro  Leu  Cys  Gly  Pro  Leu  Cys  Val  Ala  Val  Ser  Ala  Ala  Glu
     130                      135                     140

Ala  Thr  Val  Pro  Ser  Glu  Pro  Ile  Trp  Glu  Glu  Gln  Gln  Cys  Glu  Val
145                      150                     155                     160

Lys  Ala  Asp  Gly  Phe  Leu  Cys  Glu  Phe  His  Phe  Pro  Ala  Thr  Cys  Arg
                    165                     170                     175

Pro  Leu  Ala  Val  Glu  Pro  Gly  Ala  Ala  Ala  Ala  Val  Ser  Ile  Thr
               180                      185                     190

Tyr  Gly  Thr  Pro  Phe  Ala  Ala  Arg  Gly  Ala  Asp  Phe  Gln  Ala  Leu  Pro
          195                      200                     205
```

```
Val  Gly  Ser  Ser  Ala  Ala  Val  Ala  Pro  Leu  Gly  Leu  Gln  Leu  Met  Cys
     210                 215                      220

Thr  Ala  Pro  Pro  Gly  Ala  Val  Gln  Gly  His  Trp  Ala  Arg  Glu  Ala  Pro
225                      230                      235                      240

Gly  Ala  Trp  Asp  Cys  Ser  Val  Glu  Asn  Gly  Gly  Cys  Glu  His  Ala  Cys
                    245                      250                      255

Asn  Ala  Ile  Pro  Gly  Ala  Pro  Arg  Cys  Gln  Cys  Pro  Ala  Gly  Ala  Ala
                    260                 265                      270

Leu  Gln  Ala  Asp  Gly  Arg  Ser  Cys  Thr  Ala  Ser  Ala  Thr  Gln  Ser  Cys
          275                      280                      285

Asn  Asp  Leu  Cys  Glu  His  Phe  Cys  Val  Pro  Asn  Pro  Asp  Gln  Pro  Gly
          290                 295                      300

Ser  Tyr  Ser  Cys  Met  Cys  Glu  Thr  Gly  Tyr  Arg  Leu  Ala  Ala  Asp  Gln
305                      310                      315                      320

His  Arg  Cys  Glu  Asp  Val  Asp  Asp  Cys  Ile  Leu  Glu  Pro  Ser  Pro  Cys
                    325                      330                      335

Pro  Gln  Arg  Cys  Val  Asn  Thr  Gln  Gly  Gly  Phe  Glu  Cys  His  Cys  Tyr
                    340                      345                      350

Pro  Asn  Tyr  Asp  Leu  Val  Asp  Gly  Glu  Cys  Val  Glu  Pro  Val  Asp  Pro
               355                      360                      365

Cys  Phe  Arg  Ala  Asn  Cys  Glu  Tyr  Gln  Cys  Gln  Pro  Leu  Asn  Gln  Thr
     370                      375                      380

Ser  Tyr  Leu  Cys  Val  Cys  Ala  Glu  Gly  Phe  Ala  Pro  Ile  Pro  His  Glu
385                      390                      395                      400

Pro  His  Arg  Cys  Gln  Met  Phe  Cys  Asn  Gln  Thr  Ala  Cys  Pro  Ala  Asp
                    405                      410                      415

Cys  Asp  Pro  Asn  Thr  Gln  Ala  Ser  Cys  Glu  Cys  Pro  Glu  Gly  Tyr  Ile
               420                      425                      430

Leu  Asp  Asp  Gly  Phe  Ile  Cys  Thr  Asp  Ile  Asp  Glu  Cys  Glu  Asn  Gly
          435                      440                      445

Gly  Phe  Cys  Ser  Gly  Val  Cys  His  Asn  Leu  Pro  Gly  Thr  Phe  Glu  Cys
     450                      455                      460

Ile  Cys  Gly  Pro  Asp  Ser  Ala  Leu  Ala  Arg  His
465                      470                 475
```

(2) INFORMATION FOR SEQ ID NO:3:

(i) SEQUENCE CHARACTERISTICS:
        (A) LENGTH: 456 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:3:

```
Ala  Pro  Ala  Glu  Pro  Gln  Pro  Gly  Gly  Ser  Gln  Cys  Val  Glu  His  Asp
1               5                    10                       15

Cys  Phe  Ala  Leu  Tyr  Pro  Gly  Pro  Ala  Thr  Phe  Leu  Asn  Ala  Ser  Gln
               20                    25                       30

Ile  Cys  Asp  Gly  Leu  Arg  Gly  His  Leu  Met  Thr  Val  Arg  Ser  Ser  Val
          35                    40                       45

Ala  Ala  Asp  Val  Ile  Ser  Leu  Leu  Leu  Asn  Gly  Asp  Gly  Gly  Val  Gly
          50                    55                       60
```

```
Arg  Arg  Arg  Leu  Trp  Ile  Gly  Leu  Gln  Leu  Pro  Pro  Gly  Cys  Gly  Asp
 65            70                      75                           80

Pro  Lys  Arg  Leu  Gly  Pro  Leu  Arg  Gly  Phe  Gln  Trp  Val  Thr  Gly  Asp
                85                      90                      95

Asn  Asn  Thr  Ser  Tyr  Ser  Arg  Trp  Ala  Arg  Leu  Asp  Leu  Asn  Gly  Ala
               100                     105                     110

Pro  Leu  Cys  Gly  Pro  Leu  Cys  Val  Ala  Val  Ser  Ala  Ala  Glu  Ala  Thr
          115                     120                     125

Val  Pro  Ser  Glu  Pro  Ile  Trp  Glu  Glu  Gln  Cys  Glu  Val  Lys  Ala
     130                     135                     140

Asp  Gly  Phe  Leu  Cys  Glu  Phe  His  Phe  Pro  Ala  Thr  Cys  Arg  Pro  Leu
145                     150                     155                           160

Ala  Val  Glu  Pro  Gly  Ala  Ala  Ala  Ala  Val  Ser  Ile  Thr  Tyr  Gly
               165                     170                     175

Thr  Pro  Phe  Ala  Ala  Arg  Gly  Ala  Asp  Phe  Gln  Ala  Leu  Pro  Val  Gly
               180                     185                     190

Ser  Ser  Ala  Ala  Val  Ala  Pro  Leu  Gly  Leu  Gln  Leu  Met  Cys  Thr  Ala
               195                     200                     205

Pro  Pro  Gly  Ala  Val  Gln  Gly  His  Trp  Ala  Arg  Glu  Ala  Pro  Gly  Ala
     210                     215                     220

Trp  Asp  Cys  Ser  Val  Glu  Asn  Gly  Gly  Cys  Glu  His  Ala  Cys  Asn  Ala
225                     230                     235                           240

Ile  Pro  Gly  Ala  Pro  Arg  Cys  Gln  Cys  Pro  Ala  Gly  Ala  Ala  Leu  Gln
               245                     250                     255

Ala  Asp  Gly  Arg  Ser  Cys  Thr  Ala  Ser  Ala  Thr  Gln  Ser  Cys  Asn  Asp
               260                     265                     270

Leu  Cys  Glu  His  Phe  Cys  Val  Pro  Asn  Pro  Asp  Gln  Pro  Gly  Ser  Tyr
          275                     280                     285

Ser  Cys  Met  Cys  Glu  Thr  Gly  Tyr  Arg  Leu  Ala  Ala  Asp  Gln  His  Arg
     290                     295                     300

Cys  Glu  Asp  Val  Asp  Asp  Cys  Ile  Leu  Glu  Pro  Ser  Pro  Cys  Pro  Gln
305                     310                     315                           320

Arg  Cys  Val  Asn  Thr  Gln  Gly  Gly  Phe  Glu  Cys  His  Cys  Tyr  Pro  Asn
               325                     330                     335

Tyr  Asp  Leu  Val  Asp  Gly  Glu  Cys  Val  Glu  Pro  Val  Asp  Pro  Cys  Phe
               340                     345                     350

Arg  Ala  Asn  Cys  Glu  Tyr  Gln  Cys  Gln  Pro  Leu  Asn  Gln  Thr  Ser  Tyr
               355                     360                     365

Leu  Cys  Val  Cys  Ala  Glu  Gly  Phe  Ala  Pro  Ile  Pro  His  Glu  Pro  His
     370                     375                     380

Arg  Cys  Gln  Met  Phe  Cys  Asn  Gln  Thr  Ala  Cys  Pro  Ala  Asp  Cys  Asp
385                     390                     395                           400

Pro  Asn  Thr  Gln  Ala  Ser  Cys  Glu  Cys  Pro  Glu  Gly  Tyr  Ile  Leu  Asp
               405                     410                     415

Asp  Gly  Phe  Ile  Cys  Thr  Asp  Ile  Asp  Glu  Cys  Glu  Asn  Gly  Gly  Phe
               420                     425                     430

Cys  Ser  Gly  Val  Cys  His  Asn  Leu  Pro  Gly  Thr  Phe  Glu  Cys  Ile  Cys
               435                     440                     445

Gly  Pro  Asp  Ser  Ala  Leu  Val  Arg
     450                     455
```

( 2 ) INFORMATION FOR SEQ ID NO:4:

( i ) SEQUENCE CHARACTERISTICS:

( A ) LENGTH: 456 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

```
Ala Pro Ala Glu Pro Gln Pro Gly Gly Ser Gln Cys Val Glu His Asp
 1               5                   10                  15

Cys Phe Ala Leu Tyr Pro Gly Pro Ala Thr Phe Leu Asn Ala Ser Gln
            20                  25                  30

Ile Cys Asp Gly Leu Arg Gly His Leu Met Thr Val Arg Ser Ser Val
        35                  40                  45

Ala Ala Asp Val Ile Ser Leu Leu Leu Asn Gly Asp Gly Gly Val Gly
 50                  55                  60

Arg Arg Arg Leu Trp Ile Gly Leu Gln Leu Pro Pro Gly Cys Gly Asp
 65              70                  75                  80

Pro Lys Arg Leu Gly Pro Leu Arg Gly Phe Gln Trp Val Thr Gly Asp
                85                  90                  95

Asn Asn Thr Ser Tyr Ser Arg Trp Ala Arg Leu Asp Leu Asn Gly Ala
            100                 105                 110

Pro Leu Cys Gly Pro Leu Cys Val Ala Val Ser Ala Ala Glu Ala Thr
        115                 120                 125

Val Pro Ser Glu Pro Ile Trp Glu Glu Gln Gln Cys Glu Val Lys Ala
130                 135                 140

Asp Gly Phe Leu Cys Glu Phe His Phe Pro Ala Thr Cys Arg Pro Leu
145                 150                 155                 160

Ala Val Glu Pro Gly Ala Ala Ala Ala Ala Val Ser Ile Thr Tyr Gly
                165                 170                 175

Thr Pro Phe Ala Ala Arg Gly Ala Asp Phe Gln Ala Leu Pro Val Gly
            180                 185                 190

Ser Ser Ala Ala Val Ala Pro Leu Gly Leu Gln Leu Met Cys Thr Ala
        195                 200                 205

Pro Pro Gly Ala Val Gln Gly His Trp Ala Arg Glu Ala Pro Gly Ala
210                 215                 220

Trp Asp Cys Ser Val Glu Asn Gly Gly Cys Glu His Ala Cys Asn Ala
225                 230                 235                 240

Ile Pro Gly Ala Pro Arg Cys Gln Cys Pro Ala Gly Ala Ala Leu Gln
                245                 250                 255

Ala Asp Gly Arg Ser Cys Thr Ala Ser Ala Thr Gln Ser Cys Asn Asp
            260                 265                 270

Leu Cys Glu His Phe Cys Val Pro Asn Pro Asp Gln Pro Gly Ser Tyr
        275                 280                 285

Ser Cys Met Cys Glu Thr Gly Tyr Arg Leu Ala Ala Asp Gln His Arg
290                 295                 300

Cys Glu Asp Val Asp Asp Cys Ile Leu Glu Pro Ser Pro Cys Pro Gln
305                 310                 315                 320

Arg Cys Val Asn Thr Gln Gly Gly Phe Glu Cys His Cys Tyr Pro Asn
                325                 330                 335

Tyr Asp Leu Val Asp Gly Glu Cys Val Glu Pro Val Asp Pro Cys Phe
            340                 345                 350

Arg Ala Asn Cys Glu Tyr Gln Cys Gln Pro Leu Asn Gln Thr Ser Tyr
        355                 360                 365
```

```
Leu  Cys  Val  Cys  Ala  Glu  Gly  Phe  Ala  Pro  Ile  Pro  His  Glu  Pro  His
     370                 375                 380

Arg  Cys  Gln  Met  Phe  Cys  Asn  Gln  Thr  Ala  Cys  Pro  Ala  Asp  Cys  Asp
385                      390                 395                           400

Pro  Asn  Thr  Gln  Ala  Ser  Cys  Glu  Cys  Pro  Glu  Gly  Tyr  Ile  Leu  Asp
               405                      410                      415

Asp  Gly  Phe  Ile  Cys  Thr  Asp  Ile  Asp  Glu  Cys  Glu  Asn  Gly  Gly  Phe
               420                      425                 430

Cys  Ser  Gly  Val  Cys  His  Asn  Leu  Pro  Gly  Thr  Phe  Glu  Cys  Ile  Cys
          435                      440                      445

Gly  Pro  Asp  Ser  Ala  Leu  Ala  Arg
     450                      455
```

( 2 ) INFORMATION FOR SEQ ID NO:5:

( i ) SEQUENCE CHARACTERISTICS:
        ( A ) LENGTH: 446 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

```
Ala  Pro  Ala  Glu  Pro  Gln  Pro  Gly  Gly  Ser  Gln  Cys  Val  Glu  His  Asp
1                   5                    10                      15

Cys  Phe  Ala  Leu  Tyr  Pro  Gly  Pro  Ala  Thr  Phe  Leu  Asn  Ala  Ser  Gln
               20                   25                           30

Ile  Cys  Asp  Gly  Leu  Arg  Gly  His  Leu  Met  Thr  Val  Arg  Ser  Ser  Val
          35                   40                      45

Ala  Ala  Asp  Val  Ile  Ser  Leu  Leu  Leu  Asn  Gly  Asp  Gly  Gly  Val  Gly
     50                       55                      60

Arg  Arg  Arg  Leu  Trp  Ile  Gly  Leu  Gln  Leu  Pro  Pro  Gly  Cys  Gly  Asp
65                       70                   75                           80

Pro  Lys  Arg  Leu  Gly  Pro  Leu  Arg  Gly  Phe  Gln  Trp  Val  Thr  Gly  Asp
                    85                   90                           95

Asn  Asn  Thr  Ser  Tyr  Ser  Arg  Trp  Ala  Arg  Leu  Asp  Leu  Asn  Gly  Ala
               100                      105                     110

Pro  Leu  Cys  Gly  Pro  Leu  Cys  Val  Ala  Val  Ser  Ala  Ala  Glu  Ala  Thr
          115                      120                     125

Val  Pro  Ser  Glu  Pro  Ile  Trp  Glu  Glu  Gln  Gln  Cys  Glu  Val  Lys  Ala
     130                      135                     140

Asp  Gly  Phe  Leu  Cys  Glu  Phe  His  Phe  Pro  Ala  Thr  Cys  Arg  Pro  Leu
145                      150                     155                      160

Ala  Val  Glu  Pro  Gly  Ala  Ala  Ala  Ala  Val  Ser  Ile  Thr  Tyr  Gly
                    165                     170                     175

Thr  Pro  Phe  Ala  Ala  Arg  Gly  Ala  Asp  Phe  Gln  Ala  Leu  Pro  Val  Gly
               180                      185                     190

Ser  Ser  Ala  Ala  Val  Ala  Pro  Leu  Gly  Leu  Gln  Leu  Met  Cys  Thr  Ala
          195                      200                     205

Pro  Pro  Gly  Ala  Val  Gln  Gly  His  Trp  Ala  Arg  Glu  Ala  Pro  Gly  Ala
     210                      215                     220

Trp  Asp  Cys  Ser  Val  Glu  Asn  Gly  Gly  Cys  Glu  His  Ala  Cys  Asn  Ala
225                      230                     235                      240
```

```
Ile  Pro  Gly  Ala  Pro  Arg  Cys  Gln  Cys  Pro  Ala  Gly  Ala  Ala  Leu  Gln
               245                      250                      255

Ala  Asp  Gly  Arg  Ser  Cys  Thr  Ala  Ser  Ala  Thr  Gln  Ser  Cys  Asn  Asp
               260                      265                      270

Leu  Cys  Glu  His  Phe  Cys  Val  Pro  Asn  Pro  Asp  Gln  Pro  Gly  Ser  Tyr
               275                      280                      285

Ser  Cys  Met  Cys  Glu  Thr  Gly  Tyr  Arg  Leu  Ala  Ala  Asp  Gln  His  Arg
               290                      295                      300

Cys  Glu  Asp  Val  Asp  Cys  Ile  Leu  Glu  Pro  Ser  Pro  Cys  Pro  Gln
305                      310                      315                      320

Arg  Cys  Val  Asn  Thr  Gln  Gly  Gly  Phe  Glu  Cys  His  Cys  Tyr  Pro  Asn
               325                      330                      335

Tyr  Asp  Leu  Val  Asp  Gly  Glu  Cys  Val  Glu  Pro  Val  Asp  Pro  Cys  Phe
               340                      345                      350

Arg  Ala  Asn  Cys  Glu  Tyr  Gln  Cys  Gln  Pro  Leu  Asn  Gln  Thr  Ser  Tyr
               355                      360                      365

Leu  Cys  Val  Cys  Ala  Glu  Gly  Phe  Ala  Pro  Ile  Pro  His  Glu  Pro  His
               370                      375                      380

Arg  Cys  Gln  Met  Phe  Cys  Asn  Gln  Thr  Ala  Cys  Pro  Ala  Asp  Cys  Asp
385                      390                      395                      400

Pro  Asn  Thr  Gln  Ala  Ser  Cys  Glu  Cys  Pro  Glu  Gly  Tyr  Ile  Leu  Asp
               405                      410                      415

Asp  Gly  Phe  Ile  Cys  Thr  Asp  Ile  Asp  Glu  Cys  Glu  Asn  Gly  Gly  Phe
               420                      425                      430

Cys  Ser  Gly  Val  Cys  His  Asn  Leu  Pro  Gly  Thr  Phe  Glu  Cys
               435                      440                      445
```

( 2 ) INFORMATION FOR SEQ ID NO:6:

( i ) SEQUENCE CHARACTERISTICS:
        ( A ) LENGTH: 1425 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

```
ATGCTTGGGG  TCCTGGTCCT  TGGCGCGCTG  GCCCTGGCCG  GCCTGGGGTT  CCCCGCWCCC   60

GCAGAGCCGC  AGCCGGGTGG  CAGCCAGTGC  GTCGAGCACG  ACTGCTTCGC  GCTCTACCCG  120

GGCCCCGCGA  CCTTCCTCAA  TGCCAGTCAG  ATCTGCGACG  GACTGCGGGG  CCACCTAATG  180

ACAGTGCGCT  CCTCGGTGGC  TGCCGATGTC  ATTTCCTTGC  TACTGAACGG  CGACGGCGGC  240

GTTGGCCGCC  GGCGCCTCTG  GATCGGCCTG  CAGCTGCCAC  CCGGCTGCGG  CGACCCCAAG  300

CGCCTCGGGC  CCTGCGCGG  CTTCCAGTGG  GTTACGGGAG  ACAACAACAC  CAGCTATAGC  360

AGGTGGGCAC  GGCTCGACCT  CAATGGGGCT  CCCCTCTGCG  GCCCGTTGTG  CGTCGCTGTC  420

TCCGCTGCTG  AGGCCACTGT  GCCCAGCGAG  CCGATCTGGG  AGGAGCAGCA  GTGCGAAGTG  480

AAGGCCGATG  GCTTCCTCTG  CGAGTTCCAC  TTCCCAGCCA  CCTGCAGGCC  ACTGGCTGTG  540

GAGCCCGGCG  CCGCGGCTGC  CGCCGTCTCG  ATCACCTACG  GCACCCCGTT  CGCGGCCCGC  600

GGAGCGGACT  TCCAGGCGCT  GCCGGTGGGC  AGCTCCGCCG  GGTGGCTCC  CCTCGGCTTA  660

CAGCTAATGT  GCACCGCGCC  GCCCGGAGCG  GTCCAGGGGC  ACTGGGCCAG  GGAGGCGCCG  720
```

```
GGCGCTTGGG ACTGCAGCGT GGAGAACGGC GGCTGCGAGC ACGCGTGCAA TGCGATCCCT      780
GGGGCTCCCC GCTGCCAGTG CCCAGCCGGC GCCGCCCTGC AGGCAGACGG GCGCTCCTGC      840
ACCGCATCCG CGACGCAGTC CTGCAACGAC CTCTGCGAGC ACTTCTGCGT TCCCAACCCC      900
GACCAGCCGG GCTCCTACTC GTGCATGTGC GAGACCGGCT ACCGGCTGGC GGCCGACCAA      960
CACCGGTGCG AGGACGTGGA TGACTGCATA CTGGAGCCCA GTCCGTGTCC GCAGCGCTGT     1020
GTCAACACAC AGGGTGGCTT CGAGTGCCAC TGCTACCCTA ACTACGACCT GGTGGACGGC     1080
GAGTGTGTSG AGCCCGTGGA CCCGTGCTTC AGAGCCAACT GCGAGTACCA GTGCCAGCCC     1140
CTGAACCAAA CTAGCTACCT CTGCGTCTGC GCCGAGGGCT TCGCGCCCAT TCCCCACGAG     1200
CCGCACAGGT GCCAGATGTT TTGCAACCAG ACTGCCTGTC CAGCCGACTG CGACCCCAAG     1260
ACCCAGGCTA GCTGTGAGTG CCCTGAAGGC TACATCCTGG ACGACGGTTT CATCTGCACG     1320
GACATCGACG AGTGCGAAAA CGGCGGCTTC TGCTCCGGGG TGTGCCACAA CCTCCCCGGT     1380
ACCTTCGAGT GCATCTGCGG GCCCGACTCG GCCCTTGYCC GCCAC                    1425
```

(2) INFORMATION FOR SEQ ID NO:7:

(i) SEQUENCE CHARACTERISTICS:
        (A) LENGTH: 1368 baseS
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
GCWCCCGCAG AGCCGCAGCC GGGTGGCAGC CAGTGCGTCG AGCACGACTG CTTCGCGCTC       60
TACCCGGGCC CCGCGACCTT CCTCAATGCC AGTCAGATCT GCGACGGACT GCGGGCCAC       120
CTAATGACAG TGCGCTCCTC GGTGGCTGCC GATGTCATTT CCTTGCTACT GAACGGCGAC      180
GGCGGCGTTG GCCGCCGGCG CCTCTGGATC GGCCTGCAGC TGCCACCCGG CTGCGGCGAC      240
CCCAAGCGCC TCGGGCCCCT GCGCGGCTTC CAGTGGGTTA CGGGAGACAA CAACACCAGC      300
TATAGCAGGT GGGCACGGCT CGACCTCAAT GGGGCTCCCC TCTGCGGCCC GTTGTGCGTC      360
GCTGTCTCCG CTGCTGAGGC CACTGTGCCC AGCGAGCCGA TCTGGGAGGA GCAGCAGTGC      420
GAAGTGAAGG CCGATGGCTT CCTCTGCGAG TTCCACTTCC AGCCACCTG CAGGCCACTG       480
GCTGTGGAGC CCGGCGCCGC GGCTGCCGCC GTCTCGATCA CCTACGGCAC CCCGTTCGCG      540
GCCCGCGGAG CGGACTTCCA GGCGCTGCCG GTGGGCAGCT CCGCCGCGGT GGCTCCCCTC      600
GGCTTACAGC TAATGTGCAC CGCGCCGCCC GGAGCGGTCC AGGGGCACTG GGCCAGGGAG      660
GCGCCGGGCG CTTGGGACTG CAGCGTGGAG AACGGCGGCT GCGAGCACGC GTGCAATGCG      720
ATCCCTGGGG CTCCCCGCTG CCAGTGCCCA GCCGGCGCCG CCCTGCAGGC AGACGGGCGC      780
TCCTGCACCG CATCCGCGAC GCAGTCCTGC AACGACCTCT GCGAGCACTT CTGCGTTCCC      840
AACCCCGACC AGCCGGGCTC CTACTCGTGC ATGTGCGAGA CCGGCTACCG GCTGGCGGCC      900
GACCAACACC GGTGCGAGGA CGTGGATGAC TGCATACTGG AGCCCAGTCC GTGTCCGCAG      960
CGCTGTGTCA ACACACAGGG TGGCTTCGAG TGCCACTGCT ACCCTAACTA CGACCTGGTG     1020
GACGGCGAGT GTGTSGAGCC CGTGGACCCG TGCTTCAGAG CCAACTGCGA GTACCAGTGC     1080
CAGCCCCTGA ACCAAACTAG CTACCTCTGC GTCTGCGCCG AGGGCTTCGC GCCCATTCCC     1140
```

| | | | | | |
|---|---|---|---|---|---|
| CACGAGCCGC | ACAGGTGCCA | GATGTTTTGC | AACCAGACTG | CCTGTCCAGC | CGACTGCGAC | 1200 |
| CCCAACACCC | AGGCTAGCTG | TGAGTGCCCT | GAAGGCTACA | TCCTGGACGA | CGGTTTCATC | 1260 |
| TGCACGGACA | TCGACGAGTG | CGAAAACGGC | GGCTTCTGCT | CCGGGGTGTG | CCACAACCTC | 1320 |
| CCCGGTACCT | TCGAGTGCAT | CTGCGGGCCC | GACTCGGCCC | TTG Y CCGC | | 1368 |

( 2 ) INFORMATION FOR SEQ ID NO:8:

( i ) SEQUENCE CHARACTERISTICS:
        ( A ) LENGTH: 1338 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

| | | | | | |
|---|---|---|---|---|---|
| GCWCCCGCAG | AGCCGCAGCC | GGGTGGCAGC | CAGTGCGTCG | AGCACGACTG | CTTCGCGCTC | 60 |
| TACCCGGGCC | CCGCGACCTT | CCTCAATGCC | AGTCAGATCT | GCGACGGACT | GCGGGGCCAC | 120 |
| CTAATGACAG | TGCGCTCCTC | GGTGGCTGCC | GATGTCATTT | CCTTGCTACT | GAACGGCGAC | 180 |
| GGCGGCGTTG | GCCGCCGGCG | CCTCTGGATC | GGCCTGCAGC | TGCCACCCGG | CTGCGGCGAC | 240 |
| CCCAAGCGCC | TCGGGCCCCT | GCGCGGCTTC | CAGTGGGTTA | CGGGAGACAA | CAACACCAGC | 300 |
| TATAGCAGGT | GGGCACGGCT | CGACCTCAAT | GGGGCTCCCC | TCTGCGGCCC | GTTGTGCGTC | 360 |
| GCTGTCTCCG | CTGCTGAGGC | CACTGTGCCC | AGCGAGCCGA | TCTGGGAGGA | GCAGCAGTGC | 420 |
| GAAGTGAAGG | CCGATGGCTT | CCTCTGCGAG | TTCCACTTCC | CAGCCACCTG | CAGGCCACTG | 480 |
| GCTGTGGAGC | CCGGCGCCGC | GGCTGCCGCC | GTCTCGATCA | CCTACGGCAC | CCCGTTCGCG | 540 |
| GCCCGCGGAG | CGGACTTCCA | GGCGCTGCCG | GTGGGCAGCT | CCGCCGCGGT | GGCTCCCCTC | 600 |
| GGCTTACAGC | TAATGTGCAC | CGCGCCGCCC | GGAGCGGTCC | AGGGGCACTG | GGCCAGGGAG | 660 |
| GCGCCGGGCG | CTTGGGACTG | CAGCGTGGAG | AACGGCGGCT | GCGAGCACGC | GTGCAATGCG | 720 |
| ATCCCTGGGG | CTCCCCGCTG | CCAGTGCCCA | GCCGGCGCCG | CCCTGCAGGC | AGACGGGCGC | 780 |
| TCCTGCACCG | CATCCGCGAC | GCAGTCCTGC | AACGACCTCT | GCGAGCACTT | CTGCGTTCCC | 840 |
| AACCCCGACC | AGCCGGGCTC | CTACTCGTGC | ATGTGCGAGA | CCGGCTACCG | GCTGGCGGCC | 900 |
| GACCAACACC | GGTGCGAGGA | CGTGGATGAC | TGCATACTGG | AGCCCAGTCC | GTGTCCGCAG | 960 |
| CGCTGTGTCA | ACACACAGGG | TGGCTTCGAG | TGCCACTGCT | ACCCTAACTA | CGACCTGGTG | 1020 |
| GACGGCGAGT | GTGTSGAGCC | CGTGGACCCG | TGCTTCAGAG | CCAACTGCGA | GTACCAGTGC | 1080 |
| CAGCCCCTGA | ACCAAACTAG | CTACCTCTGC | GTCTGCGCCG | AGGGCTTCGC | GCCCATTCCC | 1140 |
| CACGAGCCGC | ACAGGTGCCA | GATGTTTTGC | AACCAGACTG | CCTGTCCAGC | CGACTGCGAC | 1200 |
| CCCAACACCC | AGGCTAGCTG | TGAGTGCCCT | GAAGGCTACA | TCCTGGACGA | CGGTTTCATC | 1260 |
| TGCACGGACA | TCGACGAGTG | CGAAAACGGC | GGCTTCTGCT | CCGGGGTGTG | CCACAACCTC | 1320 |
| CCCGGTACCT | TCGAGTGC | | | | | 1338 |

( 2 ) INFORMATION FOR SEQ ID NO:9:

( i ) SEQUENCE CHARACTERISTICS:
        ( A ) LENGTH: 34 bases
        ( B ) TYPE: nucleic acid
        ( C ) STRANDEDNESS: single
        ( D ) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

```
GCAAAACAAT CATGTTCGCG AAGCACTCGT GCTC                                    34
```

(2) INFORMATION FOR SEQ ID NO:10:

(i) SEQUENCE CHARACTERISTICS:
   (A) LENGTH: 2463 bases
   (B) TYPE: nucleic acid
   (C) STRANDEDNESS: single
   (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
GCTTTCCCCG GCGCCTGCAC GCGGCGCGCC TGGGTAAC ATG CTT GGG GTC CTG GTC        56
                                          Met Leu Gly Val Leu Val
                                                       -15

CTT GGC GCG CTG GCC CTG GCC GGC CTG GGG TTC CCC GCA CCC GCA GAG CCG     107
Leu Gly Ala Leu Ala Leu Ala Gly Leu Gly Phe Pro Ala Pro Ala Glu Pro
        -10             -5              -1   1                   5

CAG CCG GGT GGC AGC CAG TGC GTC GAG CAC GAC TGC TTC GCG CTC TAC CCG     158
Gln Pro Gly Gly Ser Gln Cys Val Glu His Asp Cys Phe Ala Leu Tyr Pro
                10              15                  20

GGC CCC GCG ACC TTC CTC AAT GCC AGT CAG ATC TGC GAC GGA CTG CGG GGC     209
Gly Pro Ala Thr Phe Leu Asn Ala Ser Gln Ile Cys Asp Gly Leu Arg Gly
        25              30              35

CAC CTA ATG ACA GTG CGC TCC TCG GTG GCT GCC GAT GTC ATT TCC TTG CTA     260
His Leu Met Thr Val Arg Ser Ser Val Ala Ala Asp Val Ile Ser Leu Leu
40              45              50              55

CTG AAC GGC GAC GGC GGC GTT GGC CGC CGG CGC CTC TGG ATC GGC CTG CAG     311
Leu Asn Gly Asp Gly Gly Val Gly Arg Arg Arg Leu Trp Ile Gly Leu Gln
            60              65              70

CTG CCA CCC GGC TGC GGC GAC CCC AAG CGC CTC GGG CCC CTG CGC GGC TTC     362
Leu Pro Pro Gly Cys Gly Asp Pro Lys Arg Leu Gly Pro Leu Arg Gly Phe
        75              80              85              90

CAG TGG GTT ACG GGA GAC AAC AAC ACC AGC TAT AGC AGG TGG GCA CGG CTC     413
Gln Trp Val Thr Gly Asp Asn Asn Thr Ser Tyr Ser Arg Trp Ala Arg Leu
                95              100             105

GAC CTC AAT GGG GCT CCC CTC TGC GGC CCG TTG TGC GTC GCT GTC TCC GCT     464
Asp Leu Asn Gly Ala Pro Leu Cys Gly Pro Leu Cys Val Ala Val Ser Ala
        110             115             120

GCT GAG GCC ACT GTG CCC AGC GAG CCG ATC TGG GAG GAG CAG CAG TGC GAA     515
Ala Glu Ala Thr Val Pro Ser Glu Pro Ile Trp Glu Glu Gln Gln Cys Glu
125             130             135             140

GTG AAG GCC GAT GGC TTC CTC TGC GAG TTC CAC TTC CCA GCC ACC TGC AGG     566
Val Lys Ala Asp Gly Phe Leu Cys Glu Phe His Phe Pro Ala Thr Cys Arg
            145             150             155

CCA CTG GCT GTG GAG CCC GGC GCC GCG GCT GCC GCC GTC TCG ATC ACC TAC     617
Pro Leu Ala Val Glu Pro Gly Ala Ala Ala Ala Ala Val Ser Ile Thr Tyr
160             165             170             175

GGC ACC CCG TTC CGC GCC CGC GGA GCG GAC TTC CAG GCG CTG CCG GTG GGC     668
Gly Thr Pro Phe Ala Ala Arg Gly Ala Asp Phe Gln Ala Leu Pro Val Gly
        180             185             190

AGC TCC GCC GCG GTG GCT CCC CTC GGC TTA CAG CTA ATG TGC ACC GCG CCG     719
```

```
            Ser  Ser  Ala  Ala  Val  Ala  Pro  Leu  Gly  Leu  Gln  Leu  Met  Cys  Thr  Ala  Pro
                 195                      200                      205

CCC  GGA  GCG  GTC  CAG  GGG  CAC  TGG  GCC  AGG  GAG  GCG  CCG  GGC  GCT  TGG  GAC   770
            Pro  Gly  Ala  Val  Gln  Gly  His  Trp  Ala  Arg  Glu  Ala  Pro  Gly  Ala  Trp  Asp
            210                      215                      220                      225

TGC  AGC  GTG  GAG  AAC  GGC  GGC  TGC  GAG  CAC  GCG  TGC  AAT  GCG  ATC  CCT  GGG   821
            Cys  Ser  Val  Glu  Asn  Gly  Gly  Cys  Glu  His  Ala  Cys  Asn  Ala  Ile  Pro  Gly
                      230                      235                      240

GCT  CCC  CGC  TGC  CAG  TGC  CCA  GCC  GGC  GCC  GCC  CTG  CAG  GCA  GAC  GGG  CGC   872
            Ala  Pro  Arg  Cys  Gln  Cys  Pro  Ala  Gly  Ala  Ala  Leu  Gln  Ala  Asp  Gly  Arg
                 245                      250                      255                      260

TCC  TGC  ACC  GCA  TCC  GCG  ACG  CAG  TCC  TGC  AAC  GAC  CTC  TGC  GAG  CAC  TTC   923
            Ser  Cys  Thr  Ala  Ser  Ala  Thr  Gln  Ser  Cys  Asn  Asp  Leu  Cys  Glu  His  Phe
                           265                      270                      275

TGC  GTT  CCC  AAC  CCC  GAC  CAG  CCG  GGC  TCC  TAC  TCG  TGC  ATG  TGC  GAG  ACC   974
            Cys  Val  Pro  Asn  Pro  Asp  Gln  Pro  Gly  Ser  Tyr  Ser  Cys  Met  Cys  Glu  Thr
                           280                      285                      290

GGC  TAC  CGG  CTG  GCG  GCC  GAC  CAA  CAC  CGG  TGC  GAG  GAC  GTG  GAT  GAC  TGC  1025
            Gly  Tyr  Arg  Leu  Ala  Ala  Asp  Gln  His  Arg  Cys  Glu  Asp  Val  Asp  Asp  Cys
            295                      300                      305                      310

ATA  CTG  GAG  CCC  AGT  CCG  TGT  CCG  CAG  CGC  TGT  GTC  AAC  ACA  CAG  GGT  GGC  1076
            Ile  Leu  Glu  Pro  Ser  Pro  Cys  Pro  Gln  Arg  Cys  Val  Asn  Thr  Gln  Gly  Gly
                           315                      320                      325

TTC  GAG  TGC  CAC  TGC  TAC  CCT  AAC  TAC  GAC  CTG  GTG  GAC  GGC  GAG  TGT  GTG  1127
            Phe  Glu  Cys  His  Cys  Tyr  Pro  Asn  Tyr  Asp  Leu  Val  Asp  Gly  Glu  Cys  Val
                      330                      335                      340                      345

GAG  CCC  GTG  GAC  CCG  TGC  TTC  AGA  GCC  AAC  TGC  GAG  TAC  CAG  TGC  CAG  CCC  1178
            Glu  Pro  Val  Asp  Pro  Cys  Phe  Arg  Ala  Asn  Cys  Glu  Tyr  Gln  Cys  Gln  Pro
                                350                      355                      360

CTG  AAC  CAA  ACT  AGC  TAC  CTC  TGC  GTC  TGC  GCC  GAG  GGC  TTC  GCG  CCC  ATT  1229
            Leu  Asn  Gln  Thr  Ser  Tyr  Leu  Cys  Val  Cys  Ala  Glu  Gly  Phe  Ala  Pro  Ile
                 365                      370                      375

CCC  CAC  GAG  CCG  CAC  AGG  TGC  CAG  ATG  TTT  TGC  AAC  CAG  ACT  GCC  TGT  CCA  1280
            Pro  His  Glu  Pro  His  Arg  Cys  Gln  Met  Phe  Cys  Asn  Gln  Thr  Ala  Cys  Pro
            380                      385                      390                      395

GCC  GAC  TGC  GAC  CCC  AAC  ACC  CAG  GCT  AGC  TGT  GAG  TGC  CCT  GAA  GGC  TAC  1331
            Ala  Asp  Cys  Asp  Pro  Asn  Thr  Gln  Ala  Ser  Cys  Glu  Cys  Pro  Glu  Gly  Tyr
                           400                      405                      410

ATC  CTG  GAC  GAC  GGT  TTC  ATC  TGC  ACG  GAC  ATC  GAC  GAG  TGC  GAA  AAC  GGC  1382
            Ile  Leu  Asp  Asp  Gly  Phe  Ile  Cys  Thr  Asp  Ile  Asp  Glu  Cys  Glu  Asn  Gly
                 415                      420                      425                      430

GGC  TTC  TGC  TCC  GGG  GTG  TGC  CAC  AAC  CTC  CCC  GGT  ACC  TTC  GAG  TGC  ATC  1433
            Gly  Phe  Cys  Ser  Gly  Val  Cys  His  Asn  Leu  Pro  Gly  Thr  Phe  Glu  Cys  Ile
                           435                      440                      445

TGC  GGG  CCC  GAC  TCG  GCC  CTT  GCC  CGC  CAC  ATT  GGC  ACC  GAC  TGT  GAC  TCC  1484
            Cys  Gly  Pro  Asp  Ser  Ala  Leu  Ala  Arg  His  Ile  Gly  Thr  Asp  Cys  Asp  Ser
                      450                      455                      460

GGC  AAG  GTG  GAC  GGT  GGC  GAC  AGC  GGC  TCT  GGC  GAG  CCC  CCG  CCC  AGC  CCG  1535
            Gly  Lys  Val  Asp  Gly  Gly  Asp  Ser  Gly  Ser  Gly  Glu  Pro  Pro  Pro  Ser  Pro
            465                      470                      475                      480

ACG  CCC  GGC  TCC  ACC  TTG  ACT  CCT  CCG  GCC  GTG  GGG  CTC  GTG  CAT  TCG  GGC  1586
            Thr  Pro  Gly  Ser  Thr  Leu  Thr  Pro  Pro  Ala  Val  Gly  Leu  Val  His  Ser  Gly
                           485                      490                      495

TTG  CTC  ATA  GGC  ATC  TCC  ATC  GCG  AGC  CTG  TGC  CTG  GTG  GTG  GCG  CTT  TTG  1637
            Leu  Leu  Ile  Gly  Ile  Ser  Ile  Ala  Ser  Leu  Cys  Leu  Val  Val  Ala  Leu  Leu
                      500                      505                      510                      515

GCG  CTC  CTC  TGC  CAC  CTG  CGC  AAG  AAG  CAG  GGC  GCC  GCC  AGG  GCC  AAG  ATG  1688
            Ala  Leu  Leu  Cys  His  Leu  Arg  Lys  Lys  Gln  Gly  Ala  Ala  Arg  Ala  Lys  Met
                                520                      525                      530

GAG  TAC  AAG  TGC  GCG  GCC  CCT  TCC  AAG  GAG  GTA  GTG  CTG  CAG  CAC  GTG  CGG  1739
```

| Glu | Tyr | Lys | Cys | Ala | Ala | Pro | Ser | Lys | Glu | Val | Val | Leu | Gln | His | Val | Arg |
|---|---|---|---|---|---|---|---|---|---|---|---|---|---|---|---|---|
| | | 535 | | | | | 540 | | | | | 545 | | | | |

```
ACC GAG CGG ACG CCG CAG AGA CTC TGA GCGG CCTCCGTCCA GGAGCCTGGC      1790
Thr Glu Arg Thr Pro Gln Arg Leu
550                 555

TCCGTCCAGG AGCCTGTGCC TCCTCACCCC CAGCTTTGCT ACCAAAGCAC CTTAGCTGGC   1850

ATTACAGCTG GAGAAGACCC TCCCCGCACC CCCCAAGCTG TTTTCTTCTA TTCCATGGCT   1910

AACTGGCGAG GGGGTGATTA GAGGGAGGAG AATGAGCCTC GGCCTCTTCC GTGACGTCAC   1970

TGGACCACTG GGCAATGATG GCAATTTTGT AACGAAGACA CAGACTGCGA TTTGTCCAG    2030

GTCCTCACTA CCGGGCGCAG GAGGGTGAGC GTTATTGGTC GGCAGCCTTC TGGGCAGACC   2090

TTGACCTCGT GGGCTAGGGA TGACTAAAAT ATTTATTTTT TTAAGTATT TAGGTTTTG     2150

TTTGTTTCCT TTGTTCTTAC CTGTATGTCT CCAGTATCCA CTTTGCACAG CTCTCCGGTC   2210

TCTCTCTCTC TACAAACTCC CACTTGTCAT GTGACAGGTA AACTATCTTG GTGAATTTTT   2270

TTTTCCTAGC CCTCTCACAT TTATGAAGCA AGCCCCACTT ATTCCCCATT CTTCCTAGTT   2330

TTCTCCTCCC AGGAACTGGG CCAACTCACC TGAGTCACCC TACCTGTGCC TGACCCTACT   2390

TCTTTTGCTC TTAGCTGTCT GCTCAGACAG AACCCCTACA TGAAACAGAA ACAAAAACAC   2450

TAAAAATAAA AAT                                                      2463
```

( 2 ) INFORMATION FOR SEQ ID NO:11:

( i ) SEQUENCE CHARACTERISTICS:
        ( A ) LENGTH: 49 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

```
CTTCGAGTGC ATCTGCGGGC CCGACTCGGC CCTTGCCCGC TAGGATCCC               49
```

( 2 ) INFORMATION FOR SEQ ID NO:12:

( i ) SEQUENCE CHARACTERISTICS:
        ( A ) LENGTH: 53 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:12:

```
GGGATCCTAG CGGGCAAGGG CCGAGTCGGG CCCGCAGATG CACTCGAACC TAC          53
```

( 2 ) INFORMATION FOR SEQ ID NO:13:

( i ) SEQUENCE CHARACTERISTICS:
        ( A ) LENGTH: 49 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

CTTCGAGTGC ATCTGCGGGC CCGACTCGGC CCTTGTCCGC TAGGATCCC       49

( 2 ) INFORMATION FOR SEQ ID NO:14:

( i ) SEQUENCE CHARACTERISTICS:
        ( A ) LENGTH: 53 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

GGGATCCTAG CGGACAAGGG CCGAGTCGGG CCCGCAGATG CACTCGAACC TAC       53

( 2 ) INFORMATION FOR SEQ ID NO:15:

( i ) SEQUENCE CHARACTERISTICS:
        ( A ) LENGTH: 69 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

TATGGCACCA GCAGAACCAC AACCAGGTGG AAGTCAATGT GTAGAACATG ATTGTTTTGC       60

ACTATATCC       69

( 2 ) INFORMATION FOR SEQ ID NO:16:

( i ) SEQUENCE CHARACTERISTICS:
        ( A ) LENGTH: 67 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

GGATATAGTG CAAAACAATC ATGTTCTACA CATTGACTTC CACCTGGTTG TGGTTCTGCT       60

GGTGCCA       67

( 2 ) INFORMATION FOR SEQ ID NO:17:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (genomic)

(i i i) HYPOTHETICAL: NO (i v) ANTI-SENSE: NO (x i) SEQUENCE DESCRIPTION: SEQ ID NO:17:

TTGTCGACAT GCTTGGGGTC CTGGTCCTT  29

(2) INFORMATION FOR SEQ ID NO:18:

(i) SEQUENCE CHARACTERISTICS:
        (A) LENGTH: 29 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:18:

ATAAGCTTCC GCTGCTGAGG CCACTGTGC  29

(2) INFORMATION FOR SEQ ID NO:19:

(i) SEQUENCE CHARACTERISTICS:
        (A) LENGTH: 32 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:19:

TTCTGCAGCT CGAGCCCGTG GACCCGTGCT TC  32

(2) INFORMATION FOR SEQ ID NO:20:

(i) SEQUENCE CHARACTERISTICS:
        (A) LENGTH: 29 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:20:

TTGGATCCCA CAGTGGCCTC AGCAGCGGA  29

(2) INFORMATION FOR SEQ ID NO:21:

(i) SEQUENCE CHARACTERISTICS:
        (A) LENGTH: 29 bases
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO ( x i ) SEQUENCE DESCRIPTION: SEQ ID NO:21:

| | | | |
|---|---|---|---|
| ATGTCGACAC ACTCGCCGTC CACCAGGTC | | | 29 |

( 2 ) INFORMATION FOR SEQ ID NO:22:

( i ) SEQUENCE CHARACTERISTICS:
        ( A ) LENGTH: 38 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:22:

GCGAATTCGG ATCCTCAGC GGGCAAGGGCC GAGTCGGG      38

( 2 ) INFORMATION FOR SEQ ID NO:23:

( i ) SEQUENCE CHARACTERISTICS:
        ( A ) LENGTH: 1425 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:23:

| | | | | | |
|---|---|---|---|---|---|
| ATGCTTGGGG | TCCTGGTCCT | TGGCGCGCTG | GCCCTGGCCG | GCCTGGGGTT | CCCCGCTCCC  60 |
| GCAGAGCCGC | AGCCGGGTGG | CAGCCAGTGC | GTCGAGCACG | ACTGCTTCGC | GCTCTACCCG  120 |
| GGCCCCGCGA | CCTTCCTCAA | TGCCAGTCAG | ATCTGCGACG | GACTGCGGGG | CCACCTAATG  180 |
| ACAGTGCGCT | CCTCGGTGGC | TGCCGATGTC | ATTTCCTTGC | TACTGAACGG | CGACGGCGGC  240 |
| GTTGGCCGCC | GGCGCCTCTG | GATCGGCCTG | CAGCTGCCAC | CCGGCTGCGG | CGACCCCAAG  300 |
| CGCCTCGGGC | CCTGCGCGG | CTTCCAGTGG | GTTACGGGAG | ACAACAACAC | CAGCTATAGC  360 |
| AGGTGGGCAC | GGCTCGACCT | CAATGGGGCT | CCCCTCTGCG | GCCCGTTGTG | CGTCGCTGTC  420 |
| TCCGCTGCTG | AGGCCACTGT | GCCCAGCGAG | CCGATCTGGG | AGGAGCAGCA | GTGCGAAGTG  480 |
| AAGGCCGATG | GCTTCCTCTG | CGAGTTCCAC | TTCCCAGCCA | CCTGCAGGCC | ACTGGCTGTG  540 |
| GAGCCCGGCG | CCGCGGCTGC | CGCCGTCTCG | ATCACCTACG | GCACCCCGTT | CGCGGCCCGC  600 |
| GGAGCGGACT | TCCAGGCGCT | GCCGGTGGGC | AGCTCCGCCG | CGGTGGCTCC | CCTCGGCTTA  660 |
| CAGCTAATGT | GCACCGCGCC | GCCCGGAGCG | GTCCAGGGGC | ACTGGGCCAG | GGAGGCGCCG  720 |
| GGCGCTTGGG | ACTGCAGCGT | GGAGAACGGC | GGCTGCGAGC | ACGCGTGCAA | TGCGATCCCT  780 |
| GGGGCTCCCC | GCTGCCAGTG | CCCAGCCGGC | GCCGCCCTGC | AGGCAGACGG | CGCGCTCCTGC  840 |
| ACCGCATCCG | CGACGCAGTC | CTGCAACGAC | CTCTGCGAGC | ACTTCTGCGT | TCCCAACCCC  900 |
| GACCAGCCGG | CTCCTACTC | GTGCATGTGC | GAGACCGGCT | ACCGGCTGGC | GGCCGACCAA  960 |
| CACCGGTGCG | AGGACGTGGA | TGACTGCATA | CTGGAGCCCA | GTCCGTGTCC | GCAGCGCTGT  1020 |
| GTCAACACAC | AGGGTGGCTT | CGAGTGCCAC | TGCTACCCTA | ACTACGACCT | GGTGGACGGC  1080 |
| GAGTGTGTNG | AGCCCGTGGA | CCCGTGCTTC | AGAGCCAACT | GCGAGTACCA | GTGCCAGCCC  1140 |
| CTGAACCAAA | CTAGCTACCT | CTGCGTCTGC | GCCGAGGGCT | TCGCGCCCAT | TCCCCACGAG  1200 |

| | | | | | | |
|---|---|---|---|---|---|---|
| CCGCACAGGT | GCCAGATGTT | TTGCAACCAG | ACTGCCTGTC | CAGCCGACTG | CGACCCCAAG | 1260 |
| ACCCAGGCTA | GCTGTGAGTG | CCCTGAAGGC | TACATCCTGG | ACGACGGTTT | CATCTGCACG | 1320 |
| GACATCGACG | AGTGCGAAAA | CGGCGGCTTC | TGCTCCGGGG | TGTGCCACAA | CCTCCCCGGT | 1380 |
| ACCTTCGAGT | GCATCTGCGG | GCCCGACTCG | GCCCTTGCCC | GCTGA | | 1425 |

( 2 ) INFORMATION FOR SEQ ID NO:24:

( i ) SEQUENCE CHARACTERISTICS:
        ( A ) LENGTH: 16 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:24:

| | | |
|---|---|---|
| CTTCGAGTGC | TGATAG | 16 |

( 2 ) INFORMATION FOR SEQ ID NO:25:

( i ) SEQUENCE CHARACTERISTICS:
        ( A ) LENGTH: 24 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

| | | | |
|---|---|---|---|
| AATTCTATCA | GCACTCGAAG | GTAC | 24 |

( 2 ) INFORMATION FOR SEQ ID NO:26:

( i ) SEQUENCE CHARACTERISTICS:
        ( A ) LENGTH: 14 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

| | | |
|---|---|---|
| CTAGCTGTTG | ATAG | 14 |

( 2 ) INFORMATION FOR SEQ ID NO:27:

( i ) SEQUENCE CHARACTERISTICS:
        ( A ) LENGTH: 14 bases
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

AATTCTATCA ACAG                                                                 14

RECOMBINANT DNA VECTORS, INCLUDING PLASMIDS, AND HOST CELLS FOR PRODUCTION OF TRUNCATED THROMBOMODULIN

This is a Division of application Ser. No. 08/307,444 filed Sep. 19, 1994, now issued as U.S. Pat. No. 5,516,659, which in turn is a Continuation of application Ser. No. 07/835,436 filed Mar. 27, 1992, now abandoned.

FIELD OF THE INVENTION

This invention relates to a novel polypeptide obtained by genetic recombination techniques, having activities similar to human thrombomodulin such as anticoagulant activity and thrombolytic activity, to a deoxyribonucleic acid (to be referred to as "DNA" hereinafter) fragment which encodes said polypeptide and to a process for the production of said polypeptide by means of genetic recombination techniques. This invention also relates to an agent for use in the prevention and/or treatment of hypercoagulability related diseases which comprises said polypeptide as an active ingredient.

BACKGROUND OF THE INVENTION

Heparin, antithrombin III and the like are currently used as anticoagulants. With regard to thrombolytic agents, urokinase isolated from urine or cultured kidney cells, streptokinase isolated from β-hemolytic streptococcus and the like have been put into practical use, as well as a recently developed tissue plasminogen activator.

These substances, however, have side effects such as bleeding tendency and show only one activity, anticoagulant activity or thrombolytic activity.

Recently, in the field of fundamental studies, a substance having an effect to inhibit blood coagulation and an effect to enhance formation of activated protein C which enhances fibrinolysis has been found in a rabbit lung tissue extract by N. L. Esmon et al. and named thrombomodulin (*J. Biol. Chem.*, Vol.257, p.859, 1982). It has been reported by Maruyama et al. that thrombomodulin is a thrombin receptor localized on blood vessel endothelial cells and that thrombin is deprived of its blood coagulation activity when bonded to thrombomodulin and the thrombin-thrombomodulin complex activates protein C to impart its anticoagulation effect (*J. Clin. Invest.*, Vol.75, p.987, 1985). In other words, it is possible that thrombomodulin imparts effects of both inhibiting blood coagulation and enhancing fibrinolysis and therefore can be applied to clinical means.

The following summarizes examples on the isolation of human thrombomodulin so far reported. In this instance, unless otherwise noted; data on the molecular weight cited below are those measured under non-reducing conditions by means of sodium dodecyl sulfate-polyacrylamide gel electrophoresis (SDS-PAGE).

P. W. Majerus et al. have purified thrombomodulin from human placenta and reported its a molecular weight as 75K (*J. Biol. Chem.*, Vol.259, p.12246, 1984), while Aoki et al. have purified thrombomodulin from human placenta and reported its molecular weight as 71K (*Thrombosis Res.*, Vol.37, p.353, 1985; and Japanese Patent Application Kokai No. 60-199819). Maruyama et al. have purified thrombomodulin from human lung and reported that its properties were the same as those of placenta origin (*J. Clin. Invest.*, Vol.75, p.987, 1985). In addition, Suzuki et al. have partially purified thrombomodulin from human platelet and determined its molecular weight as 78K and reported that the thrombomodulin preparations obtained from platelet, placenta and lung blood vessel endothelial cells had the same properties in terms of their electrophoretic behavior and affinities for thrombin and protein C (*J. Biochem.*, Vol.104, p.628, 1988).

In addition to these thrombomodulin molecules purified from human organs (to be referred to as "human thrombomodulin" hereinafter), the following substances having similar properties (to be referred to as "human thrombomodulin-like substance" hereinafter) have been reported.

P. W. Majerus et al. have partially purified two human thrombomodulin-like substances from a human plasma having molecular weights of 63K and 54K, respectively, and reported that similar substances existed also in urine (*J. Clin. Invest.*, Vol.75, p.2178, 1985). In addition, Ishii et al. have reported that similar substances having molecular weights of 105K, 63K, 60K, 33K, 31K and 28K (no description about reducing or non-reducing measuring condition) were excreted into urine (Abstracts of Papers, the 108th Meeting of Pharmaceutical Society of Japan, 6F05, 11-1, 1988). Other examples of human thrombomodulin-like substances obtained from urine include a mixture of substances having molecular weight of 200K, 48K and 40K (Japanese Patent Application Kokai No. 63-30423) and those having molecular weight of 39K and 31K (Japanese Patent Application Kokai No. 63-146898).

C. T. Esmon et al. have prepared a chemically synthesized peptide which corresponds to a portion of the thrombomodulin molecule (Japanese Patent Application Kokai No. 2-19399).

On the other hand, Suzuki et al. have cloned a gene of human thrombomodulin precursor containing a signal peptide from a human lung cDNA library making use of genetic engineering techniques, determined entire structure of the gene and revealed an amino acid sequence of 557 amino acid residues with a signal peptide of 18 amino acids adjacent to the sequence, with a conclusion that the N terminal amino acid sequence of human thrombomodulin was Ala Pro Ala Glu Pro (*EMBO Journal*, Vol.6, p.1891, 1987). In addition, Suzuki et al. have reported that activity of the human thrombomodulin prepared by genetic engineering techniques was the same as that of neutral human thrombomodulin purified from biological tissues (*J. Biol. Chem.*, Vol.264, p.4872, 1989) and that the human thrombomodulin-like activity was restricted to a portion of the amino acid sequence, from 345 position to 462 position amino acid residues numbered from its amino terminus, and the activity disappeared when any amino acid in the active portion was deleted (*J. Biol. Chem.*, Vol.264, p.10351, 1989; and Abstracts of Papers, the 12th Meeting of International Society of Thrombosis and Hemostasis, p.334, Title No. 1039, 1989). Also, R. W. Jackman et al. have determined complete structure of a gene of human thrombomodulin precursor and revealed an amino acid sequence of 559 amino acid residues with a signal peptide of 16 amino acids adjacent to the sequence, with a conclusion that the N terminal amino acid sequence of human thrombomodulin was Phe Pro Ala Pro Ala Glu Pro (*Proc. Natl. Acad. Sci. USA*, Vol.84, p.6425, 1987). Also, D. Wen et al. have cloned a gene of thrombomodulin precursor from a human umbilical cord vein cDNA library, determined complete structure of the gene and revealed an amino acid sequence of 554 amino acid residues with a signal peptide of 21 amino acids adjacent to the sequence, with a conclusion that the N terminal amino acid sequence of human thrombomodulin was Glu Pro (*Biochemistry*, Vol.26, p.4350, 1987).

Also, Andersen et al. have attempted to produce a human thrombomodulin-like substance which corresponds to a moiety of the human thrombomodulin molecule, by means of genetic engineering techniques (International Patent Application WO 88/09811).

In addition, P. W. Majerus et al. have developed a cDNA clone of human thrombomodulin by means of genetic engineering techniques and succeeded in expressing a protein molecule having complete amino acid sequence of human thrombomodulin (Japanese Patent Application Kokai No. 63-301791).

DISCLOSURE OF THE INVENTION

The inventors of the present invention have isolated a gene of human thrombomodulin precursor from a human cDNA library, prepared various DNA fragments from its partial structures and incorporated these fragments into microorganisms and cells in order to examine biological activities of polypeptides encoded by the DNA fragments. As a result of other series of studies, the present inventors have isolated a thrombomodulin-like substance having a molecular weight of 72K from human urine (European Patent Publication EP 376251) and have revealed that its structure and activity are different from those of already reported human thrombomodulin molecules. This new substance is hereinafter referred to as "human urine thrombomodulin". The present inventors have prepared DNA fragments, one encoding a polypeptide having the same amino acid sequence of this human urine thrombomodulin and the other fragments encoding derivatives of the polypeptide in which some amino acids of the amino acid sequence were modified by substitution, deletion, addition and the like, incorporated the thus prepared DNA fragments into microorganisms and cells, recovered polypeptides expressed in the host and checked for their biological activities and, as the results, have succeeded in obtaining novel polypeptides each of which having a thrombin binding ability, anticoagulant activity and thrombolytic activity, thereby accomplishing the present invention. These new polypeptides are hereinafter referred to as "recombinant human urine thrombomodulin (ruTM)".

The following describes the present invention in detail.

This invention relates to a novel polypeptide obtained by genetic recombination techniques, having activities similar to human thrombomodulin such as anticoagulant activity and thrombolytic activity, to a DNA fragment which encodes said polypeptide and to a process for the production of said polypeptide by means of recombinant DNA techniques, as well as to an agent for use in the prevention and treatment of hypercoagulability related diseases which comprises said polypeptide as an active ingredient. According to the present invention, there is provided a polypeptide having a thrombin binding ability, anticoagulant activity and thrombolytic activity, which comprises an amino acid sequence represented by the following formula. In the present invention, each amino acid sequence was described using the three letter code started from the N terminus. Amino acid numbers used herein are based on those of the human thrombomodulin reported by Suzuki et al. (*EMBO Journal*, Vol.6, p.1891, 987).

A polypeptide which comprises an amino acid sequence represented by the following formula:

$X_1$ Glu Pro Gln Pro Gly Gly Ser Gln Cys Val Glu
  5                                10

-continued

His Asp Cys Phe Ala Leu Tyr Pro Gly Pro Ala Thr
15                  20                      26

Phe Leu Asn Ala Ser Gln Ile Cys Asp Gly Leu Arg
            30                  35

Gly His Leu Met Thr Val Arg Ser Ser Val Ala Ala
40                      45                  50

Asp Val Ile Ser Leu Leu Leu Asn Gly Asp Gly Gly
                55                  60

Val Gly Arg Arg Arg Leu Trp Ile Gly Leu Gln Leu
            65                  70

Pro Pro Gly Cys Gly Asp Pro Lys Arg Leu Gly Pro
75                  80                      85

Leu Arg Gly Phe Gln Trp Val Thr Gly Asp Asn Asn
            90                      95

Thr Ser Tyr Ser Arg Trp Ala Arg Leu Asp Leu Asn
        100                 105                 110

Gly Ala Pro Leu Cys Gly Pro Leu Cys Val Ala Val
                115                 120

Ser Ala Ala Glu Ala Thr Val Pro Ser Glu Pro Ile
        125                 130

Trp Glu Glu Gln Gln Cys Glu Val Lys Ala Asp Gly
135                 140                     145

Phe Leu Cys Glu Phe His Phe Pro Ala Thr Cys Arg
            150                 155

Pro Leu Ala Val Glu Pro Gly Ala Ala Ala Ala Ala
160                 165                     170

Val Ser Ile Thr Tyr Gly Thr Pro Phe Ala Ala Arg
                175                 180

Gly Ala Asp Phe Gln Ala Leu Pro Val Gly Ser Ser
        185                 190

Ala Ala Val Ala Pro Leu Gly Leu Gln Leu Met Cys
195                 200                     205

Thr Ala Pro Pro Gly Ala Val Gln Gly His Trp Ala
                210                 215

Arg Glu Ala Pro Gly Ala Trp Asp Cys Ser Val Glu
220                 225                     230

Asn Gly Gly Cys Glu His Ala Cys Asn Ala Ile Pro
                235                 240

Gly Ala Pro Arg Cys Gln Cys Pro Ala Gly Ala Ala
            245                 250

Leu Gln Ala Asp Gly Arg Ser Cys Thr Ala Ser Ala
255                 260                     265

Thr Gln Ser Cys Asn Asp Leu Cys Glu His Phe Cys
                270                 275

Val Pro Asn Pro Asp Gln Pro Gly Ser Tyr Ser Cys
280                 285                     290

Met Cys Glu Thr Gly Tyr Arg Leu Ala Ala Asp Gln
                295                 300

His Arg Cys Glu Asp Val Asp Asp Cys Ile Leu Glu
        305                 310

Pro Ser Pro Cys Pro Gln Arg Cys Val Asn Thr Gln
315                 320                     325

Gly Gly Phe Glu Cys His Cys Tyr Pro Asn Tyr Asp
                330                 335

Leu Val Asp Gly Glu Cys Val Glu Pro Val Asp Pro
        340                 345                 350

-continued

Cys Phe Arg Ala Asn Cys Glu Tyr Gln Cys Gln Pro
                355                    360

Leu Asn Gln Thr Ser Tyr Leu Cys Val Cys Ala Glu
                365              370

Gly Phe Ala Pro Ile Pro His Glu Pro His Arg Cys
375              380                385

Gln Met Phe Cys Asn Gln Thr Ala Cys Pro Ala Asp
                390              395

Cys Asp Pro Asn Thr Gln Ala Ser Cys Glu Cys Pro
400              405                    410

Glu Gly Tyr Ile Leu Asp Asp Gly Phe Ile Cys Thr
                415              420

Asp Ile Asp Glu Cys Glu Asn Gly Gly Phe Cys Ser
            425                  430

Gly Val Cys His Asn Leu Pro Gly Thr Phe Glu Cys
435              440                445

$Y_1$

[in this formula, $X_1$ is a sequence represented by the following formula:

Met Leu Gly Val Leu Val Leu Gly Ala Leu Ala Leu
            −15                  −10

Ala Gly Leu Gly Phe Pro Ala Pro Ala
−5                  −1    1 or its variation in which optional number or entire amino acids are deleted starting from its N-terminus, and $Y_1$ is a sequence represented by the following formula:

Ile Cys Gly Pro Asp Ser Ala Leu $\underline{Z}$ Arg His
            450                  455

[in this instance, Z is Val (SEQ ID NO:1) or Ala (SEQ ID NO:2) ] or its variation in which optional number or entire amino acids are deleted starting from its C-terminus], preferably a polypeptide which comprises the above amino acid sequence in which $X_1$ is a sequence represented by the following formula:

Ala Pro Ala
1 and $Y_1$ is a sequence represented by the following formula:

Ile Cys Gly Pro Asp Ser Ala Leu $\underline{Z}$ Arg
            450                  455

[in this instance, Z is Val (SEQ ID NO:3) or Ala (SEQ ID NO:4)] or its variation in which optional number or entire amino acids are deleted starting from its C-terminus.

More preferably, a polypeptide which comprises the above amino acid sequence in which $X_1$ is a sequence represented by the following formula:

Ala Pro Ala
1 and $Y_1$ is a sequence represented by the following formula:

Ile Cys Gly Pro Asp Ser Ala Leu $\underline{Z}$ Arg
            450                  455

[in this instance, Z is Val (SEQ ID NO:3) or Ala (SEQ ID NO:4)] or a polypeptide which comprises the above amino acid sequence in which $X_1$ is a sequence represented by the following formula:

Ala Pro Ala
1 and entire amino acids of $Y_1$ are deleted (SEQ ID NO:5).

In addition, according to the polypeptide of the present invention, at least one amino acid of the above amino acid sequence may or may not have a sugar chain. The term "sugar chain" as used herein refers to a single sugar or a straight or branched chain of a plurality of sugars which may be in the form of so-called N-glycosidic linkage type or O-glycosidic linkage type. It is known that the activity of thrombomodulin changes depending on the linkage type of sugar chains. For example, in the case of O-glycosidic linkage type sugar chain, Parkinson, J. F. et al. have reported recently that human thrombomodulin prepared by means of genetic engineering techniques had a chondroitin sulfate-like sugar chain (J. Biol. Chem., Vol.265, p.12602, 1990). Such a sugar chain-containing polypeptide is also included in the scope of the present invention.

Because of the high technical levels attained in recent years, a part of chemical structure of a polypeptide can be changed easily without altering its activity. Consequently, any polypeptide having an amino acid sequence which has been obtained by partially modifying the aforementioned amino acid sequence by substitution, deletion, addition or the like is also included in the scope of the present invention.

According to the present invention, there is provided a DNA fragment which encodes the aforementioned inventive polypeptide. The DNA fragment of the present invention also includes any fragment having a nucleotide sequence which encodes the aforementioned modified polypeptide of the inventive polypeptide derived by means of substitution, deletion, addition or the like.

The DNA fragment of the present invention may be any fragment, provided that it contains a nucleotide sequence which encodes the inventive polypeptide, but may preferably contain a nucleotide sequence represented by the following formula. In this instance, nucleotide sequence of the DNA fragment is shown starting from its 5'-end. Also in this instance, A, G, C and T indicate deoxyadenylic acid, deoxyguanylic acid, deoxycytidylic acid and thymidylic acid, respectively.

| $X_2$ | GAGCCGC | AGCCGGGTGG | CAGCCAGTGC | GTCGAGCACG | 100 |
|---|---|---|---|---|---|
| | ACTGCTTCGC | GCTCTACCCG | GGCCCCGCGA | CCTTCCTCAA | 140 |
| | TGCCAGTCAG | ATCTGCGACG | GACTGCGGGG | CCACCTAATG | 180 |
| | AGAGTGCGCT | CCTCGGTGGC | TGCCGATGTC | ATTTCCTTGC | 220 |
| | TACTGAACGG | CGACGGCGGC | GTTGGCCGCC | GGCGCCTCTG | 260 |
| | GATCGGCCTG | CAGCTGCCAC | CCGGCTGCGG | CGACCCCAAG | 300 |
| | CGCCTCGGGC | CCCTGCGCGG | CTTCCAGTGG | GTTACGGGAG | 340 |
| | ACAACAACAC | CAGCTATAGC | AGGTGGGCAC | GGCTCGACCT | 380 |
| | CAATGGGGCT | CCCCTCTGCG | GCCCGTTGTG | CGTCGCTGTC | 420 |

```
TCCGCTGCTG  AGGCCACTGT  GCCCAGCGAG  CCGATCTGGG   460
AGGAGCAGCA  GTGCGAAGTG  AAGGCCGATG  GCTTCCTCTG   500
CGAGTTCCAC  TTCCCAGCCA  CCTGCAGGCC  ACTGGCTGTG   540
GAGCCCGGCG  CCGCGGCTGC  CGCCGTCTCG  ATCACCTACG   580
GCACCCCGTT  CGCGGCCCGC  GGAGCGGACT  TCCAGGCGCT   620
GCCGGTGGGC  AGCTCCGCCG  CGGTGGCTCC  CCTCGGCTTA   660
CAGCTAATGT  GCACCGCGCC  GCCCGGAGCG  GTCCAGGGGC   700
ACTGGGCCAG  GGAGGCGCCG  GGCGCTTGGG  ACTGCAGCGT   740
GGAGAACGGC  GGCTGCGAGC  ACGCGTGCAA  TGCGATCCCT   780
GGGGCTCCCC  GCTGCCAGTG  CCCAGCCGGC  GCCGCCCTGC   820
AGGCAGACGG  GCGCTCCTGC  ACCGCATCCG  CGACGCAGTC   860
CTGCAACGAC  CTCTGCGAGC  ACTTCTGCGT  TCCCAACCCC   900
GACCAGCCGG  GCTCCTACTC  GTGCATGTGC  GAGACCGGCT   940
ACCGGCTGGC  GGCCGACCAA  CACCGGTGCG  AGGACGTGGA   980
TGACTGCATA  CTGGAGCCCA  GTCCGTGTCC  GCAGCGCTGT  1020
GTCAACACAC  AGGGTGGCTT  CGAGTGCCAC  TGCTACCCTA  1060
ACTACGACCT  GGTGGACGGC  GAGTGTGTSG  AGCCCGTGGA  1100
CCCGTGCTTC  AGAGCCAACT  GCGAGTACCA  GTGCCAGCCC  1140
CTGAACCAAA  CTAGCTACCT  CTGCGTCTGC  GCCGAGGGCT  1180
TCGCGCCCAT  TCCCCACGAG  CCGCACAGGT  GCCAGATGTT  1220
TTGCAACCAG  ACTGCCTGTC  CAGCCGACTG  CGACCCCAAC  1260
ACCCAGGCTA  GCTGTGAGTG  CCCTGAAGGC  TACATCCTGG  1300
ACGACGGTTT  CATCTGCACG  GACATCGACG  AGTGCGAAAA  1340
CGGCGGCTTC  TGCTCCGGGG  TGTGCCACAA  CCTCCCCGGT  1380
ACCTTCGAGT  GC          Y₂                      1392
```

[in this formula, S is G or C; $X_2$ is a sequence represented by the following formula:

ATGCTTGGGG TCCTGGTCCT TGGCGCGCTG GCCCTGGCCG 40
GCCTGGGGTT CCCCGCWCCC GCA 63 [provided that W is T or A] or its variation in which optional number or entire nucleotides are deleted in triplets starting from its 5'-end; and $Y_2$ is a sequence represented by the following formula:
ATCTGCGGGC CCGACTCGGC CCTTGYCCGC CAC (SEQ ID NO:6) 1425 [provided that Y is T or C] or its variation in which optional number or entire nucleotides are deleted in triplets starting from its 3'-end].

In addition to the above nucleotide sequence, the DNA fragment of the present invention may have an appropriate promoter and an SD sequence (or a suitable ribosome binding site) bonded to its 5'-end, and if necessary a nucleotide sequence containing a translation initiation codon bonded to the 5'-end and a nucleotide sequence containing a termination codon bonded to the 3'-end.

More preferably, in the nucleotide sequence of the DNA fragment, $X_2$ is a sequence represented by the following formula:

GCWCCCGCA 63 [in this formula, W is T or A] and $Y_2$ is a sequence represented by the following formula:
ATCTGCGGGC CCGACTCGGC CCTTGYCCGC (SEQ ID NO:7) 1422 [in this instance, Y is T or C]; or $X_2$ is a sequence represented by the following formula:
GCWCCCGCA 63 [in this formula, W is T or A] and entire nucleotides of $Y_2$ are deleted (SEQ ID NO:8).

As it is well known, at least one nucleotide in a gene can be replaced by other nucleotide in accordance with the degeneracy of codon, without changing amino acid sequence of a polypeptide encoded by the gene. In consequence, the DNA fragment of the present invention may have a nucleotide sequence derived from the above inventive nucleotide sequence in which at least one nucleotide has been replaced by other nucleotide in accordance with the degeneracy of codon, especially a nucleotide sequence in which at least one nucleotide has been replaced by other nucleotide in such a way that the resulting codon shows high utilization frequency in a specific host cell when the polypeptide of the present invention is produced making use of genetic engineering techniques.

The DNA fragment of the present invention may be prepared from a natural source or synthesized chemically. The following describes examples of such processes.

In the case of the use of natural source, the DNA fragment of the present invention may be obtained by preparation of a DNA fragment encoding the inventive nucleotide sequence by using natural source such as a cDNA library prepared from cells or tissues containing thrombomodulin mRNA, a commercially available cDNA library or a chromosomal gene and then converting the thus prepared fragment into the inventive fragment.

For the purpose of preparing a cDNA library, mRNA is extracted from human tissues or human cells containing human thrombomodulin mRNA in accordance with a known method (for example, Molecular Cloning, a laboratory manual, T. Maniatis et al., Cold Spring Harbor Laboratory, 1982). Next, single-stranded cDNA is prepared using the obtained mRNA as a template followed by the synthesis of double-stranded cDNA from the single stranded cDNA (cf. Molecular Cloning, a laboratory manual, cited above; Land's method disclosed in Nucleic Acid Research, Vol.9, pp.2251–2266, 1981; Okayama-Berg's method in Mol. Cell. Biol., vol.2, pp.161–170, 1982; and Gubler-Hoffman's method in Gene, Vol.25, p.263, 1983). The thus obtained double-stranded cDNA fragments are cloned into a plasmid vector such as pBR322, pUC18 or the like or a phage vector such as λ gt10, λ gt11 or the like, and then transformed into E. coli or the like to obtain a DNA library.

When a chromosomal gene is used as a source of DNA, chromosomal DNA is extracted from human tissues or human cells, the extracted DNA is digested with appropriate restriction enzymes or by physical means, the digested fragments are cloned into a plasmid or phage vector and then the resulting vector is transformed into E. coli or the like to obtain a DNA library.

A DNA fragment encoding the inventive nucleotide sequence is then detected and isolated from the thus obtained DNA library. That is, a plasmid or a phage DNA encoding of the present invention is detected by a usually used means such as hybridization method (Wallace et al., Nucleic Acid Res., Vol.9, p.879, 1981) and then said DNA is isolated from the thus detected plasmid or phage. A DNA or an RNA fragment which has been synthesized in such a manner that it encodes entire or a part of the amino acid sequence of the polypeptide of the present invention, as disclosed herein, may be subjected to radiation labeling to obtain a convenient probe. The radiation labeling may be effected generally by labeling DNA fragment or RNA fragment with $^{32}$P, making use of kination, nick translation, random priming or the like method.

The thus isolated DNA fragment from a DNA library by the aforementioned process may be converted into the DNA fragment of the present invention in the following manner. For instance, as a preferred example, the thus isolated DNA fragment from a DNA library is digested by restriction enzymes to obtain desired DNA fragments. Separately from this, a nucleotide sequence which encodes N-terminal or C-terminal region of the polypeptide of the present invention, as well as a termination codon, a restriction enzyme recognition site, a translation initiation codon and the like, are synthesized chemically by a method which will be described later. After ligating an appropriate synthetic linker to the thus synthesized sequences and codons, they are linked to the DNA fragments obtained above and then inserted into a plasmid or a phage vector as a DNA fragment of interest. When oligonucleotides are synthesized chemically, it is possible to make an appropriate replacement of the nucleotide sequence.

Polymerase chain reaction (to be referred to as "PCR" hereinafter) may also be used as another preferable method. That is, oligonucleotide having nucleotide sequences which encodes N-terminal region, C-terminal region and an intermediate region of the polypeptide of the present invention or, if necessary, these oligonucleotides containing a termination codon, convenient restriction sites, a translation initiation codon and the like are synthesized chemically. Using the thus synthesized oligonucleotide as primers, a DNA fragment isolated from a DNA library by the aforementioned method is subjected to PCR and the DNA fragment of the present invention is obtained. An appropriate replacement of nucleotide also may be introduced to the primers. Alternatively, the aforementioned DNA library may be subjected directly to PCR making use of these primers to amplify and isolate the DNA fragment of the present invention, which are then cloned into an appropriate plasmid or phage vector. The PCR method can be carried out in the light of references or a book (*PCR Protocols, A Guide to methods and applications*, Michael A. I. et al., Academic Press, 1990).

In addition to the aforementioned methods, other commonly used methods may be available, such as the method of Kramer W. et al. (*Nucleic Acid Res.*, Vol.12, pp-9441–9465, 1984) and site-directed mutagenesis (*Methods in Enzymology*, Vol.154, pp.350–367, 1988).

On the other hand, when the inventive fragment is prepared by chemical synthesis, a nucleotide sequence of interest is designed and, if necessary, divided into fragments having proper lengths and then corresponding oligomers are synthesized chemically using a full automatic DNA synthesizer (for example, Model 381A manufactured by Applied Biosystems, Inc). If necessary, the thus obtained DNA oligomer may be subjected to phosphorylation of its DNA 5'-end using T4 polynucleotide kinase, followed by annealing. In addition, if necessary, it is possible to clone the resulting DNA fragment into an appropriate vector using T4 DNA ligase.

According to the present invention, there is provided a process for the production of the polypeptide of the present invention which comprises performing at least one step selected from the following steps of:

a) preparing a DNA fragment containing a nucleotide sequence which encodes said polypeptide, b) inserting said DNA fragment into an expression vector to obtain a recombinant DNA fragment which contains said DNA fragment and is capable of undergoing replication, c) transforming a host cell with said recombinant DNA fragment to isolate a transformant which can express said polypeptide, and d) culturing said transformant to allow the transformant to produce said polypeptide and recovering said polypeptide from resulting cultured mixture.

A DNA fragment containing a nucleotide sequence which encodes the polypeptide of the present invention may be obtained by the aforementioned means.

Any vector systems may be used as the expression vector of this process, provided that it is capable of undergoing replication in a host to be used, but preferably a vector which contains a promoter necessary for the expression of the polypeptide in a host and, if required, an SD sequence (or a suitable ribosome binding region) and/or a DNA sequence coding for a signal peptide may be employed. All promoters, SD sequences (or suitable ribosome binding regions) and nucleotide sequences encoding signal peptide which work in host can be used which may be obtained by chemical synthesis or derived from hosts to be used, virus, plasmids, phage and the like.

With regard to the host cells to be used for the introduction of the thus obtained recombinant DNA fragment, suitable cells for the expression of the polypeptide of the present invention may be selected from either eukaryotic cells such as COS cells, CHO cells, yeasts and the like or prokaryotic cells such as *E. coli*, *Bacillus subtilis* and the like, of which COS cells and CHO cells are particularly preferred. It is effective to use a host and an expression vector in such a combination that they can exhibit effective expression of the DNA fragment which encodes the inventive polypeptide. Preferred examples of the combination of host cells with expression vectors include: COS-7 cells or CHO cells with an expression vector containing the simian virus 40 (SV40) early promoter, with pH β APr-neo containing the human β-actin promoter or with a mammal expression vector derived from pCDL-SR α 296 containing the SR α promoter; and *E. coli* HB101 with an expression vector containing a DNA fragment which encoded a tryptophan promoter and a tryptophan SD sequence.

A host thus transformed with an expression vector may be cultured by generally used means for the culturing of microorganisms or animal cells, in accordance with the procedure disclosed for instance in *Seibutsu Kagaku Kogaku* (or Biochemical Engineering; S. Aiba et al., 1976, Tokyo University Press) or in *Soshiki Baiyo* (or Tissue Culture; J. Nakai et al., 1976, Asakura Shoten). The thus produced polypeptide by the transformed host cells is recovered by isolating and purifying it from the cultured mixture. Purification of the polypeptide may be carried out in the light of various generally used means which have been disclosed in many reports and books such as *Seikagaku Jikken Koza* (or Biochemical Experiments; vol.I, Protein Chemistry, 1976, edited by The Japanese Biochemical Society, Tokyo Kagaku Dojin), for instance by using an appropriate combination of purification means selected from dialysis, salting-out, gel filtration, acid precipitation, ion exchange chromatography, affinity chromatography, high performance chromatography, electrophoresis and the like. Preferably, the polypeptide of the present invention may be recovered from the cultured mixture making use of at least one means selected from ion exchange chromatography, affinity chromatography in which thrombin is used as a ligand and gel chromatography.

For example, a cultured mixture containing the polypeptide of the present invention is firstly subjected to desaltation and concentration, for instance making use of an ultrafiltration membrane with a cutoff molecular weight of 30,000. Next, the thus concentrated cultured mixture is adjusted to pH 5 to 10, preferably pH 7.3±0.2, treated at 50° to 70° C. for 5 to 45 minutes, preferably at 60°±5° C. for 15±5 minutes, in order to inactivate proteases, and then applied to a column packed with an anion exchange resin which has been equilibrated to pH 5.5 to 7.5, preferably pH 6.5±0.2. The thus adsorbed active fraction is eluted with an eluent having a pH value of 2 to 4.5, preferably pH 4.0±0.05. The resulting eluate is subjected to desaltation and concentration using an ultrafiltration membrane with a cutoff molecular weight of 30,000. After adjusting to pH 7.5, the thus concentrated eluate is subjected to affinity column chromatography in which thrombin is used as a ligand, the resulting column is washed with a buffer solution containing 0.05 to 0.3M NaCl, preferably 0.1±0.05M NaCl, active fraction is eluted with an eluent containing 0.9 to 2.0M NaCl, preferably 1.0±0.05M NaCl. After subjecting to desaltation and concentration, the thus concentrated eluate is again subjected to affinity column chromatography in which thrombin is used as a ligand, the resulting column is washed with buffer solution containing 0.3 to 0.8M NaCl, preferably 0.7±0.1M NaCl, and then active fraction is eluted with an eluent containing 0.9 to 2.0M NaCl, preferably 1.0±0.05M NaCl. Thereafter, the thus eluted polypeptide is subjected to desaltation and concentration and then to gel filtration column chromatography, to obtain an active fraction corresponding to the polypeptide of the present invention from which the inventive polypeptide can be obtained in a purified form. Alternatively, the polypeptide of the present invention may be obtained in a purified form, by subjecting the eluted fraction from the aforementioned affinity column to desaltation and concentration and then applying the concentrated fraction to SDS-PAGE under non-reducing condition. The thus obtained polypeptide of the present invention can be made into a pharmacologically acceptable form by inactivating viruses through heat treatment at 60°±2° C. for 10 hours.

Examples of the anion exchange resin eligible for use in the aforementioned purification process include DEAE cellulose, DEAE Sepharose, DEAE Cellulofine and the like, while the aforementioned affinity column in which thrombin is used as a ligand may be prepared by binding thrombin to a carrier such as cellulose, agarose, dextran or the like using cyanogen bromide and then treating the resulting resin with diisopropyl fluorophosphate (DIP), phenylmethanesulfonyl fluoride or the like. As a resin for use in gel filtration, Sephacryl S-200, Sephacryl S-300, Sephadex G150 or the like may be effective.

By applying the procedure described above, the polypeptide of the present invention can be obtained in a purified form. By the use of the same procedure, a different substance having similar properties can also be obtained.

The following describes actions and properties of the polypeptide of the present invention.
(Experimental Example 1) Affinity for thrombin (antithrombin action)
  a) When treated chromatographically using DIP-thrombin agarose, a pKCR-TM-Val-originated recombinant human urine thrombomodulin (to be referred to as "ruTM-Val" hereinafter) prepared in Example 3 and another recombinant human urine thrombomodulin (to be referred to as "ruTM-Ala" hereinafter) prepared in Example 6-(2) are adsorbed by thrombin with almost 100% accuracy.
  b) A 100 μl portion of bovine thrombin solution (1 U/ml, manufactured by Mochida Pharmaceutical Co., Ltd.) is mixed with 100 μl of a solution containing ruTM-Val or ruTM-Ala, the thus mixed solution is incubated at 37° C. for 30 minutes and then the resulting solution is mixed with 100 μl of human fibrinogen solution (2 mg/ml, manufactured by Sigma Chemical Co.) to measure coagulation time using a coagulometer (manufactured by Amelung Co. Ltd.).
  The results are shown in Table 1.

TABLE 1

| Drugs | Concentration ($OD_{280}$) | Coagulation time (seconds) |
|---|---|---|
| Control | — | 37.8 |
| ruTM-Val | 0.01 | >500 |
| ruTM-Ala | 0.01 | >500 |

As is evident from these results, ruTM-Val and ruTM-Ala have functions to bind to thrombin and strongly inhibit its coagulation activity.

Table 2 shows data adduced from Japanese Patent Application Kokai No. 62-169728 on the coagulation time measured using a thrombomodulin-like substance purified from human placenta.

TABLE 2

| Drug | Concentration ($OD_{280}$) | Coagulation time (seconds) |
|---|---|---|
| Control | — | 35.8 |
| Human placenta thrombomodulin-like substance | 0.42 | 62.3 |
|  | 0.84 | 109.9 |

In addition, according to the just cited publication, there is a description that this human placenta thrombomodulin-like substance has two times or more higher activity than the existing human thrombomodulin, thus leading to a conclusion that, from the comparison of the results shown in Tables 1 and 2, ruTM-Val and ruTM-Ala have stronger antithrombin activity than the existing human thrombomodulin.
(Experimental Example 2) Protein C activating ability Protein C activating ability is measured in the presence of thrombin, using a synthetic substrate Boc-Leu-Ser-Thr-Arg-MCA (manufactured by Peptide Research Institute, Protein Research Foundation). That is, 60 μl of 0.1M Tris-HCl buffer (ph 7.5) is mixed with 20 μl of a 10 U/ml solution of bovine thrombin (manufactured by Mochida Pharmaceutical Co., Ltd.), 10 μl of a solution containing ruTM-Ala obtained in Example 6-(2) and a mutation type recombinant human urine thrombomodulin (to be referred to as "DEL 10" hereinafter) in which 10 amino acid residues are deleted from the C-terminus of the human urine thrombomodulin (0.1 to 10 μg/ml in total), and 10 μl of 500 μg/ml solution of human protein C (American Diagnostica, Inc.), in that order. After incubation at 37° C. for 30 minutes, the resulting reaction mixture is mixed with 150 μl of a mixture solution consisting of the same volume of 1 U/ml human antithrombin (manufactured by The Green Cross Corporation) and 10 U/ml heparin (manufactured by Mochida Pharmaceutical Co., Ltd.), followed by additional incubation at 37° C. for 15 minutes. Next, the resulting reaction mixture is mixed with 250 μl of 0.1 mM solution of the aforementioned synthetic substrate and incubated at 37° C. for 10 minutes to complete the reaction which is then stopped by the addition of 500 μl of 20% acetic acid solution. Thereafter, the reaction solution is subjected to the measurement of fluorescence strength using an fluorophotometer (Hitachi, Ltd.) at an excitation wave length of 380 nm and an emission wave length of 460 nm. In this instance, human placenta thrombomodulin purified from human placenta in accordance with the procedure shown in Reference Example was used as a positive control. As shown in Table 3, protein C activating abilities of ruTM-Ala and DEL 10 calculated from the fluorescence strength are markedly high in the presence of thrombin in comparison with that of human placenta thrombomodulin.

TABLE 3

|  | Activity *1 |
| --- | --- |
| ruTM-Ala | 3.8 |
| DEL 10 | 4.1 |
| Human placenta thrombomodulin | 1.0 |

*1: Relative activity when the activity of human placenta thrombomodulin is defined as 1.

(Experimental Example 3) Anticoagulant activity

A 100 μl portion of a citric acid-added platelet poor plasma sample obtained from a healthy person is mixed with 10 μl of a solution containing ruTM-Val or ruTM-Ala (10–100 μg/ml), the thus prepared mixture is incubated at 37° C. for 2 minutes and then the reaction solution is mixed with 100 μl of human thrombin (manufactured by the Green Cross Corporation, 2 U/ml) to measure coagulation time and to find strong function of ruTM-Val and ruTM-Ala to prolong blood coagulation time.

(Experimental Example 4) Acute toxicity in mouse

When ruTM-Val or ruTM-Ala was administered by intravenous injection to 5 individuals of ddY male mouse and observed for 7 days, no case of significant toxicity or death was found within the effective dose.

(Experimental Example 5) Solubility

At room temperature, ruTM-Val and ruTM-Ala dissolved in distilled water to a concentration of at least 30 mg/ml.

In addition, when intravenously administered in vivo, the water soluble ruTM shows excellent disseminated intravascular coagulation (DIC) improving function in comparison with the slightly soluble placenta thrombomodulin which has a phospholipid binding ability.

Thus, since the polypeptide of the present invention has strong thrombin binding ability, anticoagulant activity and thrombolytic activity and has low toxicity as clear from the foregoing description and experiments, the inventive polypeptide may be used efficiently for the prevention and treatment of hypercoagulability-related diseases such as DIC, various types of thrombosis, peripheral vessel obstruction, myocardial infarction, cerebral infarction, transient cerebral ischemic attack, gestational toxicosis, hepatic insufficiency, renal insufficiency and the like.

The polypeptide of the present invention can be made into pharmaceutical preparations, preferably injections, suitable for use in efficient administration to patients, by mixing it with proper carrier or medium such as sterile water, physiological saline, a plant oil, a non-toxic organic solvent or the like generally used as drugs and, if necessary, further with a filler, a coloring agent, an emulsifying agent, a suspending agent, a stabilizer, a preservative or the like. When the polypeptide of the present invention is used as an injection, it may be administered to each patient at a time or continuously by dividing its daily dose into 1 to 6 times. Daily dose of the polypeptide of the present invention may be in the range of from 0.05 to 500 mg potency, preferably from 0.1 to 10 mg potency, as a calculated value in terms of the potency of rabbit lung thrombomodulin, though the dose may be changed suitably depending on each patient's age, weight, symptoms and the like.

In addition, the polypeptide of the present invention can be used by binding or adsorbing it to the surface of medical devices such as artificial blood vessels, artificial organs, catheters and the like, making use of a cross-linking agent or the like. By such a treatment, blood coagulation on the surface of medical devices can be prevented.

Best Mode for the Practice of the Invention

Examples of the present invention are given below by way of illustration and not by way of limitation. Abbreviations used herein are based on idiomatical expressions used in this field of science.

Experiments related to genetic recombination DNA techniques were carried out, unless otherwise noted, in the light of books including "Maniatis T. et al, Molecular Cloning, Cold Spring Harbor Laboratory, 1982" and "S. Kobayashi, Handbook for Gene Manipulation Experiments, JATEC Publishers, 1985" and instructions attached to purchased reagents and devices. Also, unless otherwise noted, restriction enzymes used in the following experiments were purchased from Takara Shuzo Co., Ltd. or from New England Biolabs, Inc.

A high ruTM-Ala expressing strain, TMM-B1C, used in the following examples has been deposited on Jun. 25, 1991, in Fermentation Research Institute, Agency of Industrial Science and Technology 1-3 Higoshi 1-chrome, Taskubashi, Ibaraki-Ken 305, Japan, and has been assigned the designation as FERM BP-3463.

EXAMPLE 1

Cloning of thrombomodulin cDNA and construction of expression plasmid (1) Cloning of thrombomodulin cDNA The oligonucleotide probe shown in FIG. 1 was prepared using a DNA synthesizer (already mentioned) based on an amino acid sequence, Glu His Asp Cys Phe Ala,

15 which is a part of the N-terminal amino acid sequence of human urine thrombomodulin (SEQ ID NO:3) isolated and purified from human urine. The thus synthesized oligonucleotide was purified using OPC column (Applied Biosystems, Inc.) and its 5'-end was labeled using T4 polynucleotide kinase (Takara Shuzo Co., Ltd.) and [$\gamma$–$^{32}$P] ATP (Amersham). Next, the resulting reaction solution was applied to Sephadex G-25 column (Pharmacia) to separate the labeled oligonucleotide probe from [$\gamma$–$^{32}$P] ATP for use in the following procedure as a probe.

Total RNA was prepared from about 20 g portion of human placenta by means of guanidinium isothiocyanate extraction. A 10 mg of the thus extracted total RNA was subjected twice to oligo (dT)-cellulose chromatography (type 7, Pharmacia) to obtain about 90 μg of purified poly A$^+$ RNA, followed by cDNA construction using the thus obtained poly A$^+$ RNA. That is, double-stranded cDNA was prepared (using a cDNA synthesizing system, Amersham) from 20 μg of the poly A$^+$ RNA using oligo dT as a primer by the method of Gubler and Hoffman (Gubler, U. and Hoffman, B. J., Gene, Vol.25, p.263, 1983). The thus prepared cDNA was subjected to methylation using EcoRI methylase and then EcoRI linkers were linked. After digestion with EcoRI, the free linker and DNA fragments less than 500 bp were removed by gel filtration (BioGel A50 m, Bio-Rad Laboratories). The resulting DNA fragment was cloned into a phage vector γ gt11 (Amersham) to prepare a cDNA library, with an efficiency of about 90% and containing about 2×10⁶ independent clones. Phage particles in the thus prepared γ gt11 library were plated on E. coli strain Y1090 as the host in the usual way with such an inoculum size that plaques were formed about 5×10³ per plate having a diameter of 9 cm. The thus formed plaques were transferred on nylon filters (Hybond-N, Amersham), and the resulting filters were put on filter paper soaked with 1.5M NaCl/0.5M NaOH solution for 5 minutes and then with 1.5M NaCl/0.5M Tris-HCl buffer (pH 8.0) for 5 minutes to denature DNA. Next, the thus treated nylon filters were washed with 0.36M NaCl/20 mM sodium phosphate (ph 7.4)/2 mM EDTA (pH 7.4) solution and then air-dried. After fixing the DNA on the filters by ultraviolet ray irradiation, the resulting filters were washed with a 0.1% SDS/×0.1 SSC solution (SSC: ×1 concentration; 150 mM NaCl/15 mM sodium citrate, pH 7.0) at 65° C. for 1 hour. The thus DNA-fixed filters were subjected to pre-hybridization at 65° C. for 6 to 24 hours in a solution of ×6 SSC/50 mM sodium phosphate buffer (pH 6.8)/×1 Denhardt solution/100 µg/ml denatured salmon sperm DNA, followed by overnight hybridization at 37° C. in the same solution supplemented with about 10⁶ cpm/ml of the aforementioned 540 -end labeled oligonucleotide. The filters were washed with ×6 SSC for 5 to 30 minutes at 4° C., 37° C. and 42° C. in that order, air-dried and then subjected to autoradiography.

By checking about 3×10⁶ plaques through the above procedure, a total of 23 clones showing positive reaction with the probe were isolated. After subjecting each of the thus isolated phage clones to plaque formation, the above hybridization procedure was repeated to obtain 9 clones which showed the positive signal again and from which phage DNA samples were collected. When digested with a restriction enzyme, EcoRI, about 0.7 to 2.5 kb inserted DNA were found in the γ gt11. A restriction map of the largest 2.5 kb inserted DNA is shown in FIG. 2. Two DNA fragments obtained by cleavage with EcoRI and PstI of the 2.5 Kb inserted DNA were isolated and subcloned into an M13 phage, mp18 or mp19, between EcoRI and PstI cloning site in the usual way to prepare single-stranded phage DNA and were sequenced by a DNA sequencer (370A, Applied Biosystems, Inc.). As the results, a sequence corresponding to the N-terminal sequence of human thrombomodulin was found in an amino acid sequence deduced from the nucleotide sequence of an EcoRI/PstI DNA fragment of about 0.4 kb, which confirmed that the cloned cDNA is of human urine thrombomodulin. FIGS. 3(a) to 3(m) show results of the nucleotide sequence of the 2.5 kb DNA fragment.

(2) Construction of Recombinant Human Urine Thrombomodulin Expression Vector

Construction of expression plasmid for use in mammalian cells (FIG. 4(a)-FIG. 4(b))

The 2.5 kb thrombomodulin cDNA was digested with EcoRI and subjected to agarose gel electrophoresis, and DNA fragments isolated from the gel were subcloned into plasmid pUC118. Plasmid DNA thus prepared was digested with EcoRI and then the 3' recessed termini were filled using T4 DNA polymerase (Takara Shuzo Co., Ltd.). The BamHI linkers (Takara Shuzo Co., Ltd.) were connected to the blunt-ended termini using a ligation kit (Takara Shuzo Co., Ltd.), and the resulting DNA fragment was double-digested with BamHI and KpnI, followed by electrophoresis to isolate a DNA fragment of about 1.5 kb from the gel.

Two synthetic oligonucleotide linkers (each linker was prepared from a set of a 49 mer and a 53 mer complementary oligonucleotide) as shown in FIG. 5(a) were obtained using the aforementioned DNA synthesizer, each linker starting from the KpnI site of the human urine thrombomodulin cDNA, encoding a C-terminal amino acid sequence (Leu Ala Arg) of human urine thrombomodulin and ending just after the terminal sequence with a terminal codon and BamHI site. In this case, purification of each single-stranded oligonucleotide was carried out using reverse phase HPLC (C8 column, AQUAPORE RP-30, Applied Biosystems, Inc.). The 49 mer oligonucleotide was subjected to 540 -end phosphorylation using T4 polynucleotide kinase (already mentioned) and then annealed with the 53 mer oligonucleotide.

Next, the linker was ligated with previously prepared BamHI/KpnI fragment of about 1.5 kb thrombomodulin cDNA (already mentioned), and digested with BamHI and then, the digested DNA fragments were subjected to agarose gel electrophoresis to isolate a 1.6 Kb DNA fragment. On the other hand, an expression vector in mammalian cells, pKCR (O'Hara, K. et al., Proc. Natl. Acad. Sci., USA, Vol.78, p.1527, 1981), was digested with BamHI and then treated with a phosphatase (Takara Shuzo Co., Ltd.) to obtain a linear DNA fragment which was subsequently subjected to ligation (already described) with the 1.6 kb DNA fragment to prepare human urine thrombomodulin expression plasmids, pKCR-TM-Ala and pKCR-TH-Val, in mammalian cells.

Construction of expression plasmid in E. coli (FIG. 6(a) –FIG. 6(b))

Each of the aforementioned plasmids, pKCR-TM-Ala and pKCR-TM-Val, was double-digested with BamHI and SmaI, and the resulting 1.3 kb DNA fragment was isolated by agarose gel electrophoresis. Next, an oligonucleotide linker consisting of 69 mer and 67 mer synthetic oligonucleotides as shown in FIG. 5(b) was prepared in the same manner as described in the foregoing. The 67 mer oligonucleotide was subjected to phosphorylation using a nucleotide kinase and then annealed with the 69 mer oligonucleotide, the resulting linker was ligated with the aforementioned 1.3 kb DNA fragment, and was double-digested with SmaI and BamHI. On the other hand, plasmid pM450 (Kanamori, T. et al., Gene, Vol.66, pp.295–300, 1988) was double-digested with BamHI and NdeI, and were subjected to agarose gel electrophoresis to isolate a DNA fragment of about 3.2 kb. The thus prepared 3.2 kb DNA fragment was ligated with each of the two linker-connected thrombomodulin cDNA fragments obtained above to prepare plasmids pM450-TM-Ala and p M450-TM-Val for the expression of recombinant human urine thrombomodulin in E. coli.

EXAMPLE 2

Cloning of thrombomodulin cDNA and construction of expression plasmid (1) Cloning of thrombomodulin cDNA A single-stranded cDNA was prepared from 10 µg of the poly A⁺ RNA derived from human placenta obtained in Example 1-(1) using an oligo dT primer and a reverse transcriptase (Takara Shuzo Co., Ltd.) as usual.

Separately from this, a total of 6 oligonucleotides (FIG. 7) were prepared using a DNA synthesizer (already mentioned), each of which corresponding to the nucleotide sequence encoded a part of the human urine thrombomodulin cDNA fragment obtained in Example 1-(1), with its 540-end having a recognition site of a restriction enzyme selected from SalI, BamHI, EcoRI, HindIII or PstI. In this instance, each of the S1, S2 and S3 oligonucleotides corresponds to a part of "+" strand of the human urine thrombomodulin, while each of the A1, A2 and A3 oligonucleotides corresponds to a part of "−" strand. Also in this instance, XhoI site was introduced in the S3 oligonucleotide by means of silent mutation. Also the A3 oligonucleotide contains a DNA sequence which corresponds to a termination codon. The thus synthesized thrombomodulin specific oligonucleotide primers were purified using OPC column (already mentioned).

Next, PCR was carried out using the single-stranded cDNA as a template and the chemically synthesized oligonucleotides as primers to obtain human urine thrombomodulin cDNA by dividing it into three parts. That is, 100 µl of a reaction solution consisting of a 10 mM Tris-HCl (pH 8.3)/50 mM KCl mM MgCl$_{/0.01}$% gelatin solution containing about 50 ng of the single-stranded cDNA, 0.8 µg of each primer (S1 and A1) and 2.5 units of a thermostable DNA polymerase (Perkin-Elmer Cetus) was applied to Thermal Cycler (Perkin-Elmer Cetus) and PCR was carried out under conditions of: annealing, 55° C. for 2 minutes; synthesis of complementary chain, 72° C. for 3 minutes; thermal denaturation, 94° C. for 1 minute; and cycle numbers, 30. After purification by phenol.chloroform extraction and ethanol precipitation, amplified DNA fragment I having a size of about 450 bp was obtained. The PCR procedure was repeated in the same manner except that S2 and A2 or S3 and A3 were used as primers to obtain DNA fragment II of about 650 bp and DNA fragment III of about 350 bp. The thus prepared fragments I, II and III were digested with SalI/BamHI, HindIII/ScaI and PstI/BamHI respectively and subcloned into pUC118 in the usual way to obtain pUC118-FI, pUC118-FII and pUC118-FIII.

The three DNA fragments of the human urine thrombomodulin cDNA thus obtained by PCR were connected one another in the following manner to construct a cDNA fragment which encodes a signal peptide and the whole mature protein supplemented with termination codon to its 340 -end.

First, pUC118-FI was digested with HindIII and BamHI, and the digested products were subjected to agarose gel electrophoresis in the usual way to isolate a DNA fragment having a size of about 450 bp. The thus isolated DNA fragment was further digested with DdeI and the digests were subjected to purification to isolate a DNA fragment, FI, with cohesive end of HindIII and DdeI in its 540 -end and 340 -end in the same manner, another DNA fragment, FII, which has a size of about 650 bp with cohesive end of DdeI and SalI in its 540 -end and 340 -end, was obtained by subjecting the pUC118-FII to digestion with HindIII and SalI, separation of the resulting digests, digestion with DdeI and purification of the fragment of interest. As well as still another DNA fragment, FIII, which has a size of about 350 bp with cohesive end of XhoI and EcoRI in its 5'-end and 340 -end, was also obtained by subjecting the pUC118-FIII to digestion with XhoI and EcoRI, separation of the resulting digests and purification of the fragment of interest. Next, the fragments FI, FII and FIII were ligated into HindIII/EcoRI cloning site of pUC118 to obtain a plasmid pUC-TM. (The construction process is shown in FIG. 8.) The cDNA of interest was subcloned in the usual way into M13 phage, mp18 or mp19, single-stranded DNA fragment was prepared in order to determine oligonucleotide sequence by a DNA sequencer (already mentioned), it was confirmed that this cDNA encoded the human urine thrombomodulin. The results of the nucleotide sequence determination were shown in FIG. 9(a)–FIG. 9(b).

(2) Construction of recombinant human urine thrombomodulin expression vector

The plasmid pUC-TM containing human urine thrombomodulin cDNA prepared in Example 2-(1) was digested with SalI and BamHI, and a DNA fragment of about 1.4 Kb was isolated and purified in the usual way making use of agarose gel electrophoresis. The thus prepared fragment was inserted into a SalI-BamHI cloning site of an expression vector for mammalian cells pH β APr-1-neo (P. Gunning et al., *Proc. Natl. Acad. Sci. USA*, Vol.84, p.4831, 1987), to construct a vector LK444-TM for the expression of recombinant thrombomodulin. Next, a plasmid pAdD26SV (A) (R. J. Kaufman et al., *Mol. Cell. Biol.*, vol.2, p.1304, 1982) which contains a gene coding for dihydrofolate reductase (to be referred to as "DHFR" hereinafter) was digested with BgII and the recessed termini were filled using T4 DNA polymerase (already mentioned), and the fragment was digested with EcoRI and then subjected to agarose gel electrophoresis in the usual way to isolate and purify a DNA fragment of about 3 Kb containing the DHFR gene. Next, the expression vector LK444-TM obtained above was digested with a AatII and the recessed termini were filled using T4 DNA polymerase (already mentioned), and the fragment was digested with EcoRI and then subjected to agarose gel electrophoresis in the usual way to isolate and purify a DNA fragment of about 9 kb. Thereafter, the thus prepared DNA fragment was ligated with the previously prepared DHFR gene-containing DNA fragment in the usual way to construct LK444-TM-DHFR. (FIG. 10(a)–FIG. 10(b))

Next, pUC-TM was digested with SalI and EcoRI, and subjected to agarose gel electrophoresis in the usual way to isolate and purify a DNA fragment having a length of about 1.4 kb. Together with a PstI-SalI linker (5'-TCGATGCA-3') which has been prepared by a DNA synthesizer (already mentioned) and purified by OPC column (already mentioned), the thus obtained DNA fragment was ligated into a PstI/EcoRI cloning site of an expression vector for mammalian cells, pCDL-SR α 296 (Y. Takebe et al. *Mol. Cell. Biol.*, Vol.8, p.466, 1988), to construct a human urine thrombomodulin expression vector, pCDSR α-TM. Next, the thus constructed vector was digested with SalI and ClaI, the recessed termini were filled using T4 DNA polymerase (already mentioned) and then subjected to agarose gel electrophoresis in the usual way to isolate and purify a DNA fragment containing the human urine thrombomodulin cDNA. On the other hand, the aforementioned LK444-TM-DHFR was digested with EcoRI and NdeI, the recessed termini were filled using T4 DNA polymerase (already mentioned) and then subjected to agarose gel electrophoresis in the usual way to isolate a purify DNA fragment containing the DHFR gene. Thereafter, the thus prepared DNA fragment was ligated with the previously prepared DNA fragment containing the human urine thrombomodulin cDNA in the usual way to construct pCDSR α-TM-DHFR. (FIG. 11(a)–FIG. 11(b))

EXAMPLE 3

Expression of thrombomodulin

Each of the plasmids pKCR-TM-Ala and pKCR-TM-Val prepared in Example 1 was transfected into COS-7 cells (ATCC No. CRL1651) by means of DEAE dextran method to express recombinant thrombomodulin. That is, semiconfluent COS-7 cells prepared in advance were transfected with the plasmid DNA at a ratio of about 1 μg DNA per about 2×10⁵ cells in accordance with the method of Lauren et al. (Lauren, M., *Proc. Natl. Acad. Sci. USA*, Vol.78, p.7575, 1981). The thus treated cells were cultured for 3 days using Dulbecco's modified Eagle's medium (to be referred to as "D-ME medium" hereinafter) which has been supplemented with 0.01% albumin, followed by recovering of culture supernatant to obtain a crude recombinant human urine thrombomodulin solution. Transfection was carried out in the same manner and a 10 liter portion of the resulting culture filtrate was subjected to desalting and concentration making use of an ultrafiltration membrane of 30,000-molecular-weight cutoff.

After adjusting to pH 7.3, the concentrated culture filtrate was treated at 60° C. for 15 minutes. The resulting sample was applied to a column packed with 300 ml DEAE cellulose (Whatman) which has been equilibrated with phosphate buffer in advance, the column was washed with 750 ml of the same buffer used for the equilibration, and the thus adsorbed active fraction was eluted with acetate buffer (pH 4.0).

The eluate was concentrated using an ultrafiltration membrane of cutoff molecular weight of 30,000, adjusted to pH 7.5 with 2M NaOH and then applied to a 2.5 ml of DIP-thrombin-agarose column which has been equilibrated with 0.02M Tris-HCl buffer (pH 7.5) containing 0.1M NaCl, 1 mM benzamidine hydrochloride and 0.5 mM $CaCl_2$, thereby adsorbing the active fraction. Next, the column was washed with 25 ml of the same buffer used for the equilibration, and the active fraction was then eluted with 0.02M Tris-HCl buffer (ph 7.5) containing 1M NaCl, 1 mM benzamidine hydrochloride and 0.5 mM EDTA. The eluate was dialyzed against the same buffer as used in the equilibration and then subjected to purification by means of DIP-thrombin-agarose column chromatography in the same manner as described above.

The resulting eluate was concentrated using an ultrafiltration membrane of cutoff molecular weight of 30,000 and then subjected to gel filtration using a column packed with 500 ml Sephacryl S-300 (Pharmacia Fine Chemicals) which has been equilibrated in advance with 0.01M phosphate buffer (pH 7.0) containing 0.14M NaCl, thereby recovering the active fraction of interest.

By carrying out the above production process, about 0.5 mg of purified recombinant human urine thrombomodulin was obtained from each of the culture flitrates derived from pKCR-TM-Ala and pKCR-TM-Val. Each of the thus purified recombinant human urine thrombomodulin showed a single band by non-reduced SDS-PAGE. When examined, both showed high activities.

After subjecting 300 μg of each of the polypeptides of the present invention to reductive carboxymethylation in accordance with the method of C. H. Hirs et al. (*Methods in Enzymol.*, Vol. 11, p.199, 1967) and then to desalting, N-terminal amino acid sequences of the thus treated samples were determined using gas phase protein sequencer (Applied Biosystems, Inc., model 470A), and their C-terminal amino acid sequences were analyzed by means of carboxypeptidase method (*Biochem. Biophys. Acta*, Vol.397, p.443, 1975). As the results, the N-terminal and C-terminal amino acid sequences of these two polypeptides coincided with those of the 72K human urine thrombomodulin. In other words, amino acid sequence of the polypeptide obtained from the pKCR-TM-Ala-originated culture filtrate was, N-terminal: Ala Pro Ala Glu Pro Gln
     1        5
C-terminal: Leu Ala Arg   SEQ ID NO: 4
       455 and amino acid sequence of the polypeptide obtained from the pKCR-TM-Val-derived culture filtrate was as follows.

N-terminal: Ala Pro Ala Glu Pro Gln
     1        5
C-terminal: Leu Val Arg   SEQ ID NO: 3
       455

EXAMPLE 4

Expression of human urine thrombomodulin

The plasmid pCDSR α-TM-DHFR constructed in Example 2 was transfected into CHO cells by means of electroporation (the method reported by D. Zerbib et al. in *Biochem. Biophys. Res. Comm.*, Vol.129, p.611, 1985, was slightly modified) in the following manner to express recombinant human urine thrombomodulin.

That is, CHO DXB11 cells (Urlaub, G. and Chasin, L. A., *Proc. Natl. Acad. Sci.* Vol. 77, p.4216, 1980) were cultured at 37° C. for 2 days in 5% $CO_2$-95% air using Ham's F12 (Flow Laboratories, Inc.) containing 10% fetal bovine serum (Nippon Bio-Supply Center Co., Ltd.) (to be referred to as "medium-①" hereinafter), dispersed by trypsin-EDTA treatment and then suspended in 50 ml of fresh medium-①. The thus prepared cell suspension was centrifuged at 1000 r.p.m. for 5 minutes using a refrigerated centrifuge (Kokusan Enshinki Co., Ltd.). After discarding the supernatant, the resulting cells were suspended in 50 ml of a sucrose-containing phosphate buffer (540 mM sucrose/7.0 mM sodium dihydrogenphosphate 12 $H_2O$/4.2 mM magnesium chloride, pH 7.4) and centrifuged at 1,000 r.p.m. for 5 minutes. After repeating the above suspension step in the sucrose-containing phosphate buffer and subsequent centrifugation step, the resulting cells were suspended in the sucrose-containing phosphate buffer to a density of 1×10⁷ cells/ml, and 0.4 ml of the thus prepared cell suspension was transferred in a cuvette for an electroporation apparatus, Gene Pulser TM (BIO-RAD). To the cuvette was further added 0.4 ml of plasmid pCDSR α-TM-DHFR which has been prepared to a concentration of 50 μg/ml of the sucrose-containing phosphate buffer. The resulting mixture in the cuvette was allowed to stand for 15 minutes in an ice bath and then subjected to electropotation using Gene Pulser. Thereafter, the thus treated cells in the cuvette were allowed to stand for 10 minutes in an ice bath and then made into a cell suspension of 1×10⁴ cells/ml using the medium-①. 10 ml of the thus prepared cell suspension was transferred in a culture dish of 10 cm in diameter and cultured at 37° C. in 5% $CO_2$-95% air. Two days after the culture, medium in the culture dish was removed and the culture was continued by supplying the dish with 10 ml of HEM α (−) (contains no ribonucleosides or deoxyribonucleosides, manufactured by GIBCO) containing 10% of heat inactivated and dialyzed fetal bovine serum (already mentioned) (to be referred to as "medium-②" hereinafter). The culture was continued by replacing the medium-② with fresh one every 2 to 4 days, and single colonies consisting of 100 to 200 cells were isolated after 16 or 19 days of the culture by means of penicillin cup method. The collected cells were transferred to a 96 well multi-dish (A/S Nunc) and cultured using the medium-②. Each of the thus obtained clones, when it grew into proper level, was cultured again by changing the culture dish. During the culture process, a portion of the cells were cultured in a serum-free medium and the amount of recombinant thrombomodulin in the resulting culture supernatant was measured in the following manner to evaluate recombinant thrombomodulin productivity of each clone. That is, 3 ml cell suspension adjusted to $4.2 \times 10^4$ cells/ml using the medium-② was poured in a culture dish of 35 ram in diameter and cultured at 37° C. for 3 days in 5% $CO_2$-95% air. Next, after removing the culture medium, the cultured cells were washed with PBS-Tween and cultured again using 3 ml of MEM α (−) containing 5 KIU/ml of aprotinin (Repulson, Mochida Pharmaceutical Co., Ltd.) at 37° C. for 2 days in 5% $CO_2$-95% air to measure biological activity in the resulting culture supernatant. In this way, a clone showing a high activity was selected as a high expression strain of recombinant thrombomodulin. In addition, the thus selected recombinant thrombomodulin high expression strain was adjusted to $1 \times 10^4$ cells/ml using the medium-② which has been supplemented with 20 nM methotrexate (Lederle Japan) (to be referred to as "MTX" hereinafter), and 10 ml of the thus prepared cell suspension was poured in a culture dish of 10 cm in diameter and cultured at 37° C. in 5% $CO_2$-95% air. Thus obtained resistant cells to 20 mM MTX were subjected to cloning making use of penicillin cup method, and recombinant thrombomodulin productivity of each clone was evaluated to select a recombinant thrombomodulin high expression strain. The concentration of expression of the thus selected high expression strain, TMM-B1C, was 1.3 μg/ml. The recombinant thrombomodulin in the culture supernatant was recovered and purified in accordance with the procedure of Example 3, and its N-terminal and C-terminal amino acid sequences were determined also in accordance with the procedure of Example 3. As the results, these sequences were confirmed as follows.

N-terminal: Ala Pro Ala Glu Pro Gln
            1                      5
C-terminal: Leu Ala Arg SEQ ID NO: 4
            455

EXAMPLE 5

Expression in *E. coli*

*E. coli* strain HB101 transformed with the plasmid pM450-TM-Ala or pM450-TM-Val prepared in Example 1 were cultured overnight in 5 ml of L-broth containing 100 μg/ml of ampicillin (to be referred to as "Ap" hereinafter). The resulting culture broth was inoculated into 50 volumes M9CA medium containing 100 μg/ml Ap and 50 μg/ml tryptophan and cultured at 37° C. for about 3 hours until the cell growth reached its late log phase, followed by the addition of 3 β-indoleacrylic acid (Wako Pure Chemical Industries, Ltd.) to a final concentration of 10 μg/ml and subsequent culturing for 3 to 5 hours. The thus cultured cells were recovered using a centrifuge (MR-15, Tomy Seiko Co., Ltd.) and washed with physiological saline, and the resulting precipitate was suspended in a 2% sodium dodecyl sulfate/1 mM EDTA/10 mM Tris-HCl (ph 7.4) solution in an amount equivalent to 1/10 volume of the culture broth to disperse the cells and then lysed by heat treatment at 90° C. for 5 minutes. Thereafter, insoluble materials in the lysate were removed by a centrifuge (already mentioned) at 15,000 r.p.m. for 10 minutes, and the resulting supernatant was dialyzed against PBS to obtain a lysate sample.

Two lysate samples obtained in this manner were checked for their reactivity with anti-human urine thrombomodulin antibody. That is, each well of a flat bottom 96 well microtiter plate (Immulom-600, Greiner, Inc.) was charged with 100 μl of anti-human urine thrombomodulin antibody (obtained by sensitizing a rabbit with 72K human urine thrombomodulin prepared from urine and purifying the resulting serum by ammonium sulfate precipitation and DEAE-Sepharose column) which has been adjusted to a concentration of 10 μg/ml using 0.1M sodium carbonate buffer, pH 9.6. After allowing to stand at 4° C. for 16 hours, the thus treated wells were washed three times with 10 mM phosphate buffer, pH 7.4, containing 0.05% Tween-20 (Bio-Rad Laboratories, Inc.) (to be referred to as "PBS-Tween" hereinafter). Each of the thus treated wells was charged with 300 μl of Block Ace (Dainippon Pharmaceutical Co., Ltd.) solution which has been diluted four times with water, incubated at 37° C. for 1 hour to block un-adsorbed portion and then washed three times with PBS-Tween. After adding 100 μl of the lysate and incubating at 37° C. for 1.5 hours, each well was washed three times with PBS-Tween, charged with 100 μl of 10 μg/ml biotin-treated anti-human urine thrombomodulin antibody solution and then incubated at 37° C. for 1 hour. After washing three times with PBS-Tween, 100 μl of a horseradish peroxidase-labeled streptoavidin (Zymed Laboratories, Inc.) solution was added and then incubated at 37° C. for 1 hour. After washing three times with PBS-Tween, each well was washed once with citrate-phosphate buffer, pH 4.0, and then charged with 200 μl of a color-developing agent (ABTS: (2,2'-azinobis(3-ethylbenzthiazoline sulfonic acid)diammonium salt) which has been dissolved to a concentration of 1 mg/ml in citrate-phosphate buffer, pH 4.0, containing 0.003% hydrogen peroxide. The coloring reaction was continued until sufficient absorbance was obtained and then stopped by adding 50 μl of 21 mg/ml hydrogen fluoride solution to each well. Thereafter, absorbance at a wave length of 405 nm was measured using a microtiter plate reader.

As the results, color development was observed in the lysate of the strain containing pM450-TM-Ala or pM450-TM-Val, while no color development was observed in a lysate of *E. coli* strain HB101 containing plasmid pH450, which has been obtained in the same culture and preparation procedures.

EXAMPLE 6

Construction and expression of deletion mutant (1) Construction of deletion mutant expression vector A vector for use in the expression of DEL 10 was constructed in the following manner. Oligonucleotides (D5-16U and D5-24L) comprising 10 mer and 24 mer as shown in FIG. 12(a) were prepared using a DNA synthesizer (already mentioned), purified by OPC column (already mentioned) and then annealed in the usual way to obtain a DNA fragment having cohesive end of KpnI and EcoRI. This fragment was ligated in the usual way with a DNA fragment of about 4.5 kb prepared from a KpnI/EcoRI digest of the pUC-TM obtained in Example 2-(1) to construct plasmid pUC-DEL10 which encodes human thrombomodulin signal peptide and DEL 10 supplemented with a terminal codon to its 340 -end. The thus constructed plasmid was digested with EcoRI/MluI, the digests were subjected to agarose gel electrophoresis in the usual way to isolate a DNA fragment of about 650 bp and then the thus isolated fragment was ligated in the usual way with a DNA fragment of about 4.5 kb prepared from a EcoRI/MluI digest of the pCDSR α-TM obtained in Example 2-(2) to construct plasmid pCDSR α-DEL10 (FIG. 13(a)–FIG. 13 (b)).

On the other hands a vector for use in the expression of a mutated recombinant human urine thrombomodulin in which C-terminal 49 amino acids are deleted from the human urine thrombomodulin (to be referred to as "DEL 49" hereinafter) was constructed in the following manner.

Oligonucleotides (D10-14U and D10-14L) each comprising 14 mer as shown in FIG. 12(b) were prepared using a DNA synthesizer (already mentioned), purified using OPC column (already mentioned) and then annealed in the usual way to obtain a DNA fragment having cohesive end of NheI and EcoRI. This fragment was ligated in the usual way with a DNA fragment of about 5 kb prepared from a EcoRI/NheI digest of the pCDSR α-TM obtained in Example 1-(2) to construct plasmid pCDSR α-DEL49 which contains the cDNA of interest. (FIG. 13(a)–FIG. 13(b))

(2) Expression in animal cells

The pCDSR α-TM prepared in Example 2-(2) and pCDSR α-DEL10 and pCDSR α-DEL49 prepared in Example 6-(1) were introduced into COS I cells to express ruTM-Ala, DEL 10 and DEL 49respectively. That is, a 0.5 μg of pCDSR α-TM, pCDSR α-DEL10 or pCDSR α-DEL49 was dissolved in 5 μl of TE, and the resulting solution was mixed with 700 μl of D-ME medium containing 0.2 mg/ml of DEAE-dextran and 50 mM Tris-HCl(pH 7.4) to prepare a solution of DNA-DEAE-dextran mixture. The thus prepared DNA-DEAE-dextran mixture solution was added dropwise to COS I cells which have been cultured to a semi-confluent state in a culture dish of 35 mm in diameter, and the thus treated cells were cultured at 37° C. for 4 hours in the presence of 5% $CO_2$-95% air. After removing the DNA-DEAE-dextran mixture solution, D-ME medium containing 1% fetal bovine serum (already mentioned) was added to the culture dish. After culturing at 37° C. for 48 to 96 hours in the presence of 5% $CO_2$-95% air, the resulting culture supernatant was recovered and protein C activating ability of the supernatant was measured in accordance with the procedure of Experimental Example 2. As the results, the biological activity was found in ruTM-Ala and DEL 10, though not sufficiently enough in DEL 49The results are shown in Table 4.

TABLE 4

|  | Activity *1 |
|---|---|
| ruTM-Ala | 3.8 |
| DEL 10 | 4.1 |
| Human placenta thrombomodulin | 1.0 |

*1: Relative activity when the activity of human placenta thrombomodulin is defined as 1.

The following describes examples of pharmaceutical preparations containing the polypeptide of the present invention.

EXAMPLE 7

| ruTM-Ala | 20.0 mg |
|---|---|
| Purified gelatin | 50.0 mg |
| Sodium phosphate | 34.8 mg |
| Sodium chloride | 81.8 mg |
| Mannitol | 25.0 mg |

After dissolving the above components in 10 ml of distilled water for injection use, the resulting solution was sterilized by filtration, dispensed in 1.0 ml aliquots into sterile vials and then freeze-dried to prepare injections.

EXAMPLE 8

| ruTM-Ala | 40.0 mg |
|---|---|
| Albumin | 20.0 mg |
| Sodium phosphate | 34.8 mg |
| Sodium chloride | 81.8 mg |
| Mannitol | 25.0 mg |

After weighing each of the above components, a freeze-dried pharmaceutical preparation was prepared in the same manner as in Example 7.

EXAMPLE 9

| DEL 10 | 20.0 mg |
|---|---|
| Purified gelatin | 50.0 mg |
| Sodium phosphate | 34.8 mg |
| Sodium chloride | 81.8 mg |
| Mannitol | 25.0 mg |

After weighing each of the above components, a freeze-dried pharmaceutical preparation was prepared in the same manner as in Example 7.

(Reference Example)

Example of the preparation of human placenta thrombomodulin

Thrombomodulin was purified from human placenta in accordance with the procedure disclosed in Japanese Patent Application Kokai No. 60-199819. That is, 12 kg of human placental samples (30 placentae) were washed with 0.02M Tris-HCl buffer, ph 7.5, containing 0.25M sucrose and 1 mM benzamidine and then homogenized using a meat grinder. After subjecting the thus homogenized suspension to centrifugation at 3,000 r.p.m. for 40 minutes, the resulting precipitate was suspended in the aforementioned buffer solution, stirred for 10 minutes and then centrifuged to obtain a precipitate. The above step was repeated three times using 20 liters of the buffer solution per one cycle, and the finally obtained precipitate was extracted with 60 liters of 0.02M Tris-HCl buffer, pH 7.5, containing 0.25M sucrose, 1 mM benzamidine hydrochloride and 0.5% (v/v) Triton X-100 (Sigma Chemical Co.). The amount of total protein in the thus extracted solution was found to be 46.7 g (determined by Lowry's method, the same shall apply hereinafter). The 60 liter crude extract was applied to DIP-thrombin-agarose column (4 φ×16 cm) which has been equilibrated in advance with 0.02M Tris-HCl buffer, pH 7.5, containing 0.1M NaCl, 0.5 mM $CaCl_2$, 0.1 mM benzamidine hydrochloride and 0.5% (v/v) Triton X-100, and then the thus protein-adsorbed column was washed with 2 liters of the same buffer solution used for the equilibration. Next, elution was carried out using 0.02M Tris-HCl buffer, pH 7.5, containing 1M NaCl, 0.1 mM EDTA, 1 mM benzamidine hydrochloride and 0.5% (v/v) Triton X-100. In this way, 650 ml of eluate containing 1.7 g of protein was obtained. The eluate was subjected to desaltation and concentration using an ultrafiltration apparatus (Millipore Corp., nominal cutoff molecular weight of 30,000) and then adsorbed to the DIP-thrombin-agarose column which has been conditioned in the same manner as described above. Next, after washing with 150 ml of 0.02M Tris-HCl buffer, pH 7.5, containing 0.4M NaCl, 0.5 mM CaCl2, 0.1 mM benzamidine hydrochloride and 0.5% (v/v) Triton X-100, elution was carried out by means of density gradient using 0.02M Tris-HCl buffer, pH 7.5, containing 0.1 mM EDTA, 1 mM benzamidine hydrochloride, 0.5% (v/v) Triton X-100 and NaCl (0.4–1M). When the eluate was collected in 30 ml fractions, a total of 1290 ml fractions of interest containing 68 mg of protein was obtained. The eluate was subjected to desaltation and concentration using an ultrafiltration apparatus (Millipore Corp., nominal cutoff molecular weight of 30,000) and then to gel filtration to collect a fraction of interest using S-300 (Pharmacia) column (2.6 φ×90 cm) which has been conditioned in advance with 0.01M Tris-HCl buffer, pH 7.0, containing 0.05% Triton X-100 and 0.14M NaCl. The thus obtained human placenta thrombomodulin preparation contained 3.1 mg of protein.

BRIEF DESCRIPTION OF THE DRAWINGS

Figure 1:
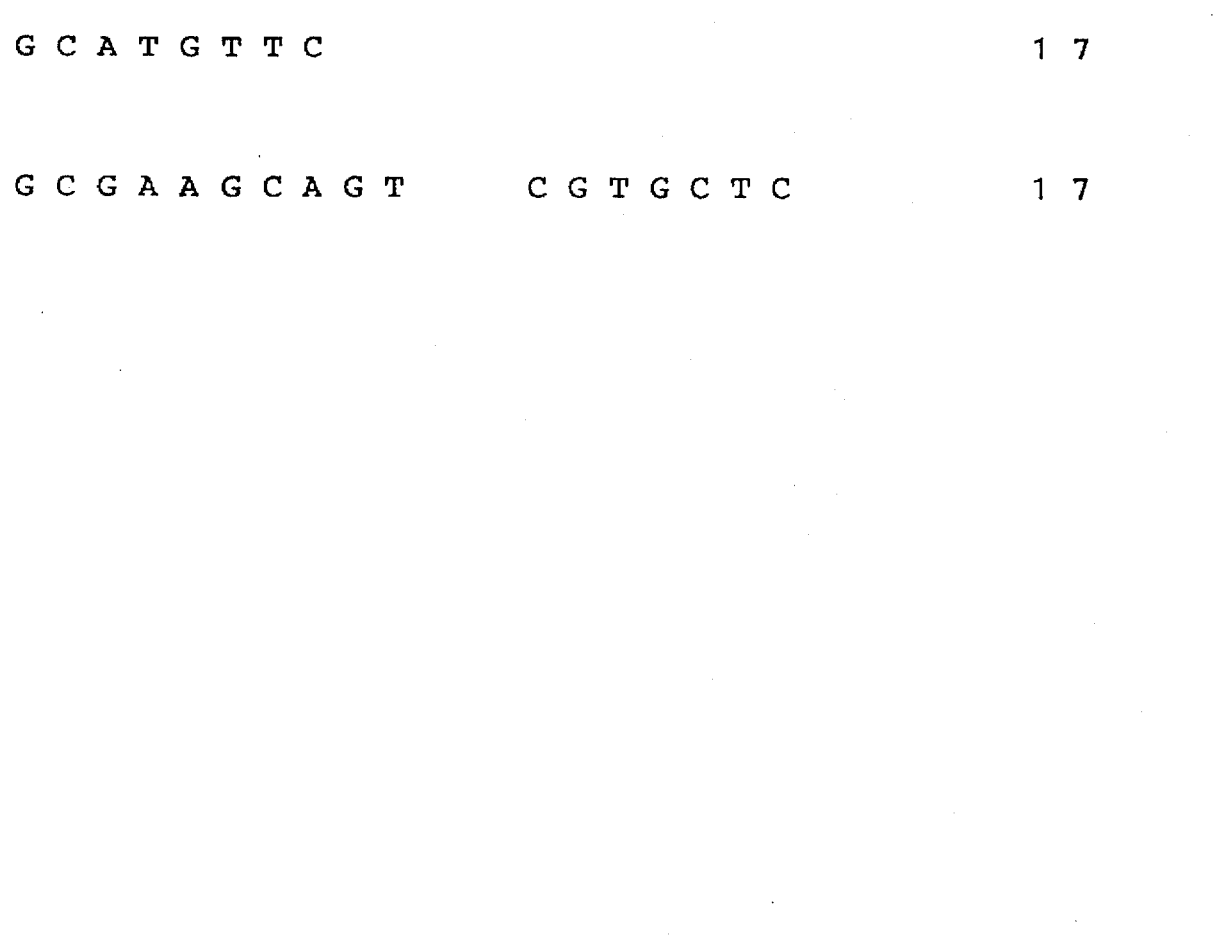

FIG. 1 is a graph showing oligonucleotide sequence (SEQ ID NO:9) of a probe to be used in the present invention.

FIG. 3(a) to FIG. 3(m) include a graph showing oligonucleotide sequence (SEQ ID NO:10) of a 2.5 kb cDNA fragment containing a DNA fragment which encodes the polypeptide of the present invention and deduced amino acid sequence of the polypeptide.

FIG. 5(a) pKCR-TM-Ala 49 mer (SEQ ID NO:11); pKCR-TM-Ala 53 mer (SEQ ID NO:12); pKCR-TM-Val 49 mer (SEQ ID NO:13) and pKCR-TM-Val 53 mer (SEQ ID NO:14) and FIG. 5(b) pM450-TM-Ala 69 mer (SEQ ID NO:15); and pM450-TM-Ala 67 mer (SEQ ID NO:16) are graphs showing oligonucleotides used for the construction of the plasmids of the present invention.

FIG. 7 is a graph showing oligonucleotides S1 (SEQ ID NO:17); S2 (SEQ ID NO:18); S3 (SEQ ID NO:19); A1 (SEQ ID NO:20); A2 (SEQ ID NO:21); A3 (SEQ ID NO:22); used for the construction of the plasmid of the present invention.

FIG. 9(a) and FIG. 9(b) include a graph showing oligonucleotide sequence (SEQ ID NO:23) of a DNA fragment which encodes the polypeptide ruTM-Ala of the present invention.

FIG. 12 is a graph showing oligonucleotides D5-160 (SEQ ID NO:24) D5-24L (SEQ ID NO:25); D10-140 (SEQ ID NO:26) and D10-142 (SEQ ID NO:27) used for the construction of deletion mutant expression plasmids pCDSR α-DEL10 and pCDSR α-DEL49 of the present invention.

INDUSTRIAL APPLICABILITY

Figure 2:
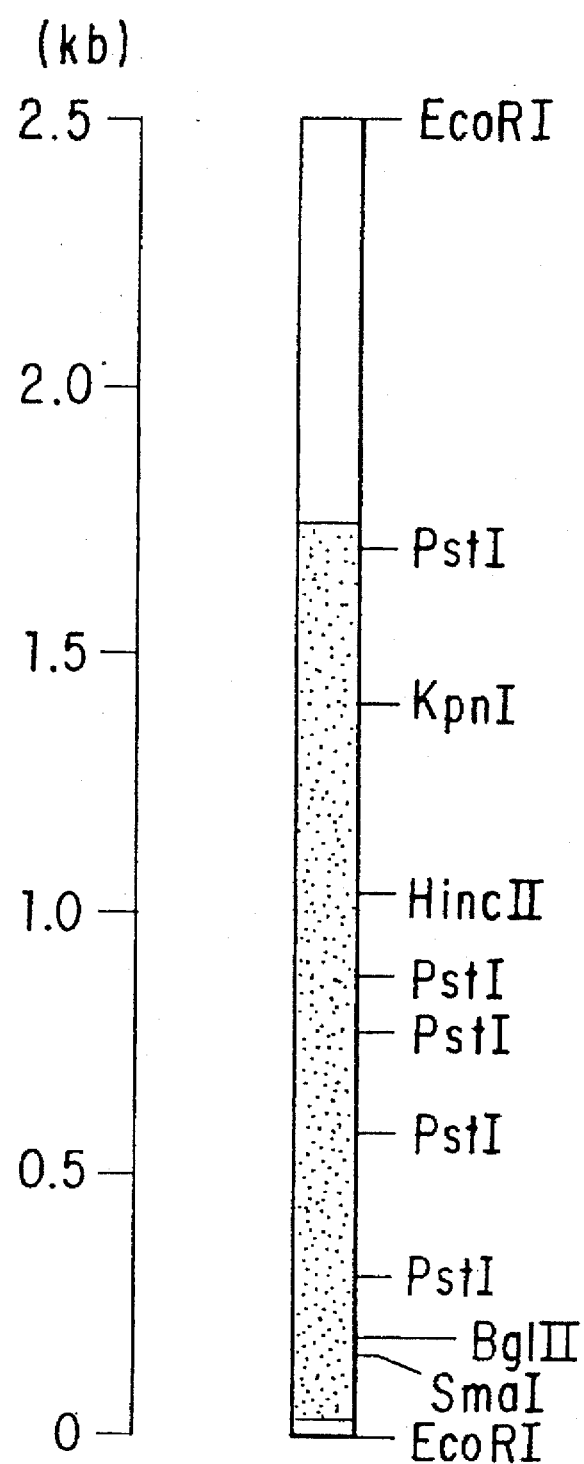
FIG. 2 is a restriction map of a 2.5 kb cDNA fragment containing a DNA fragment which encodes the polypeptide of the present invention.
Figure 4A:
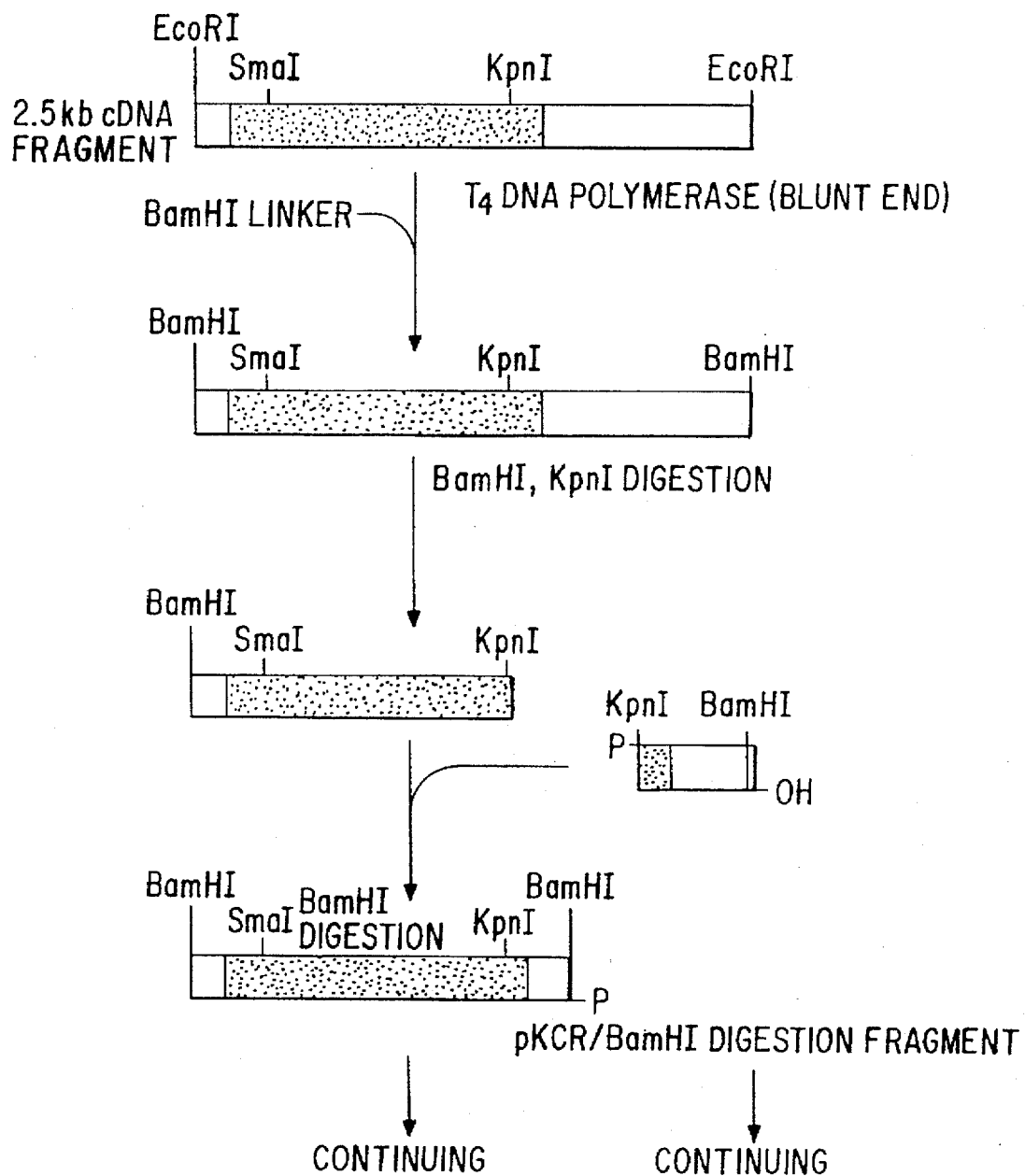
FIG. 4(a) and FIG. 4(b) include a graph showing a procedure for the construction of expression plasmids pKCR-TM-Ala and pKCR-TM-Val of the present invention for use in mammalian cells.
Figure 4B:
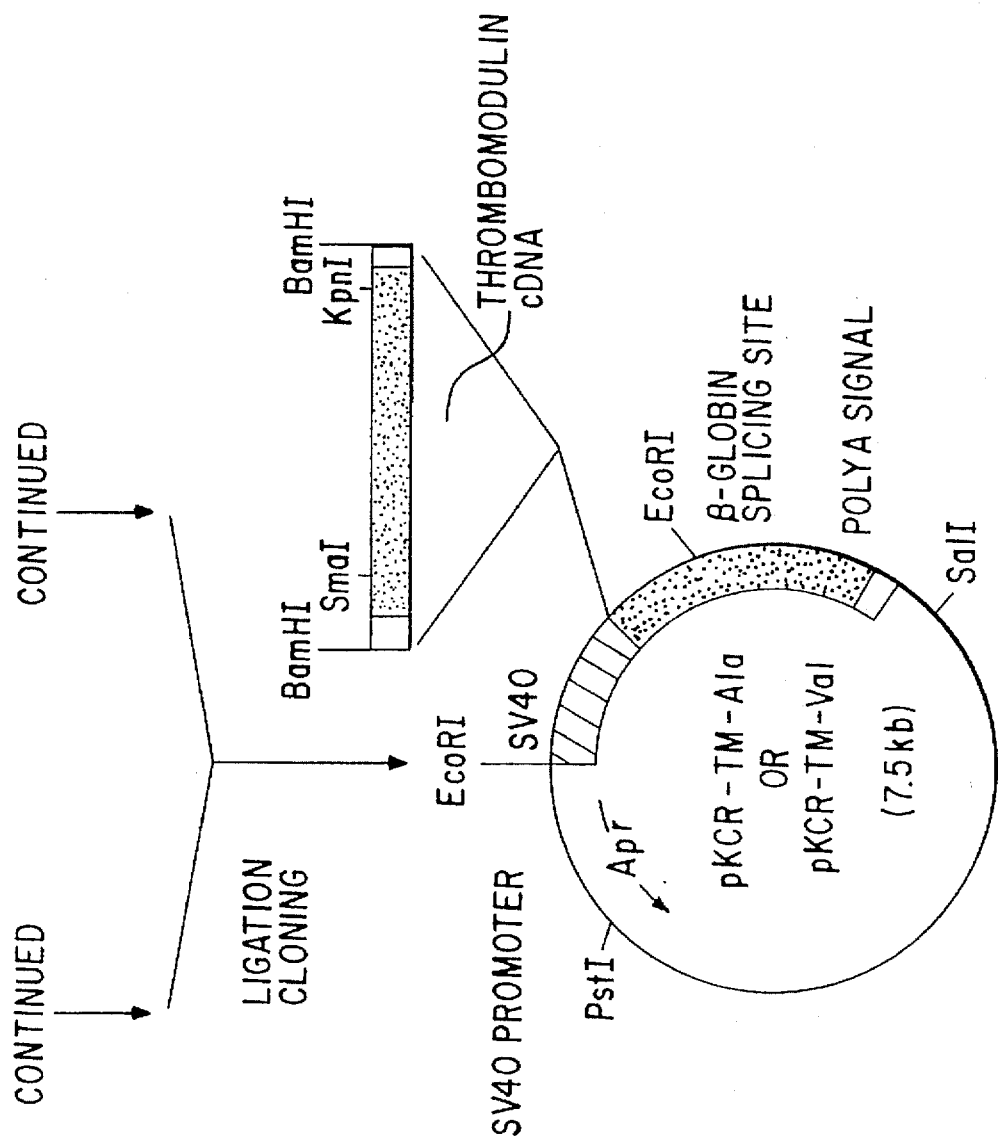
Figure 6A:
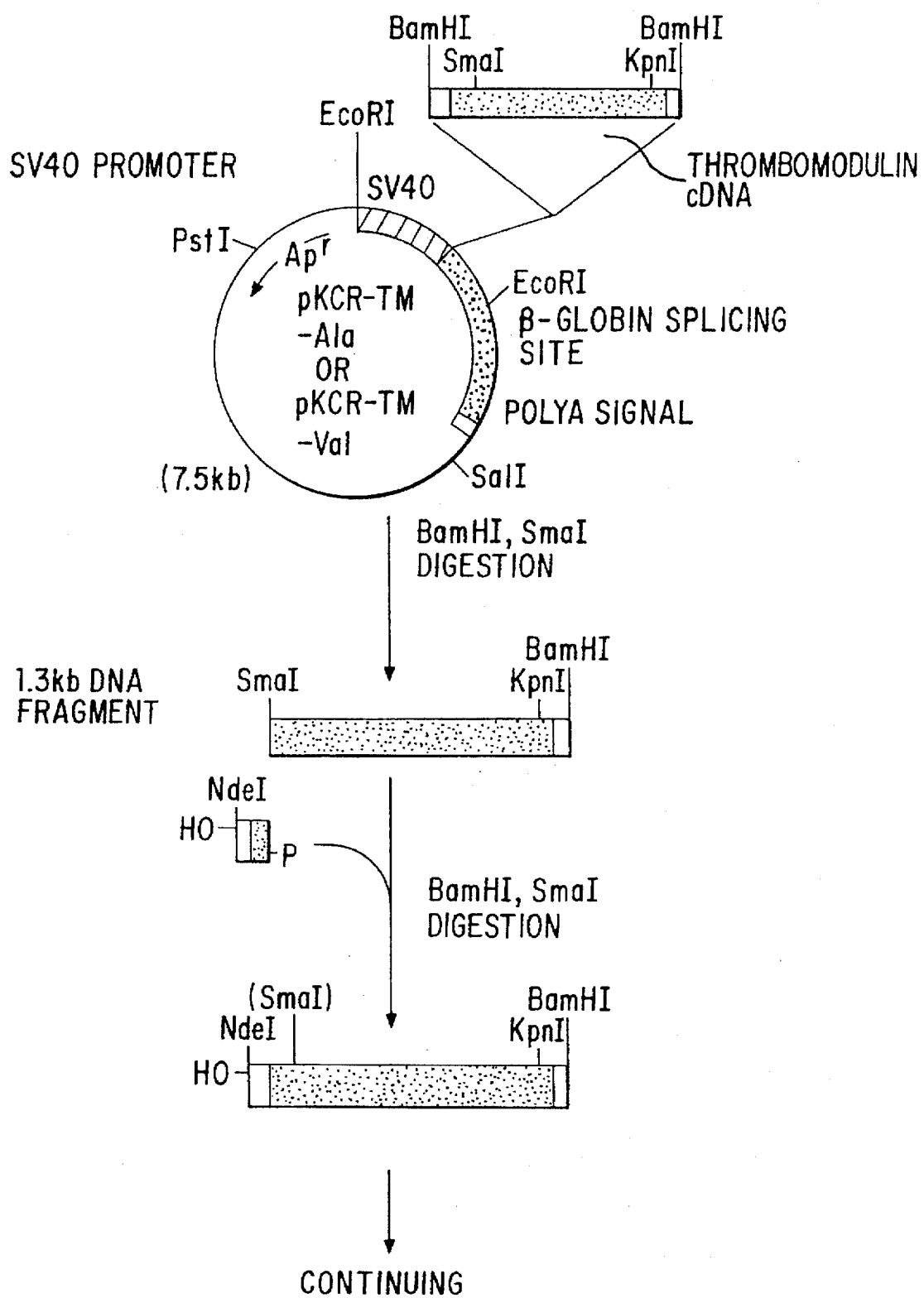
FIG. 6(a) and FIG. 6(b) include a graph showing a procedure for the construction of expression plasmids pM450-TM-Ala and pM450-TM-Val of the present invention for use in E. coli.
Figure 6B:
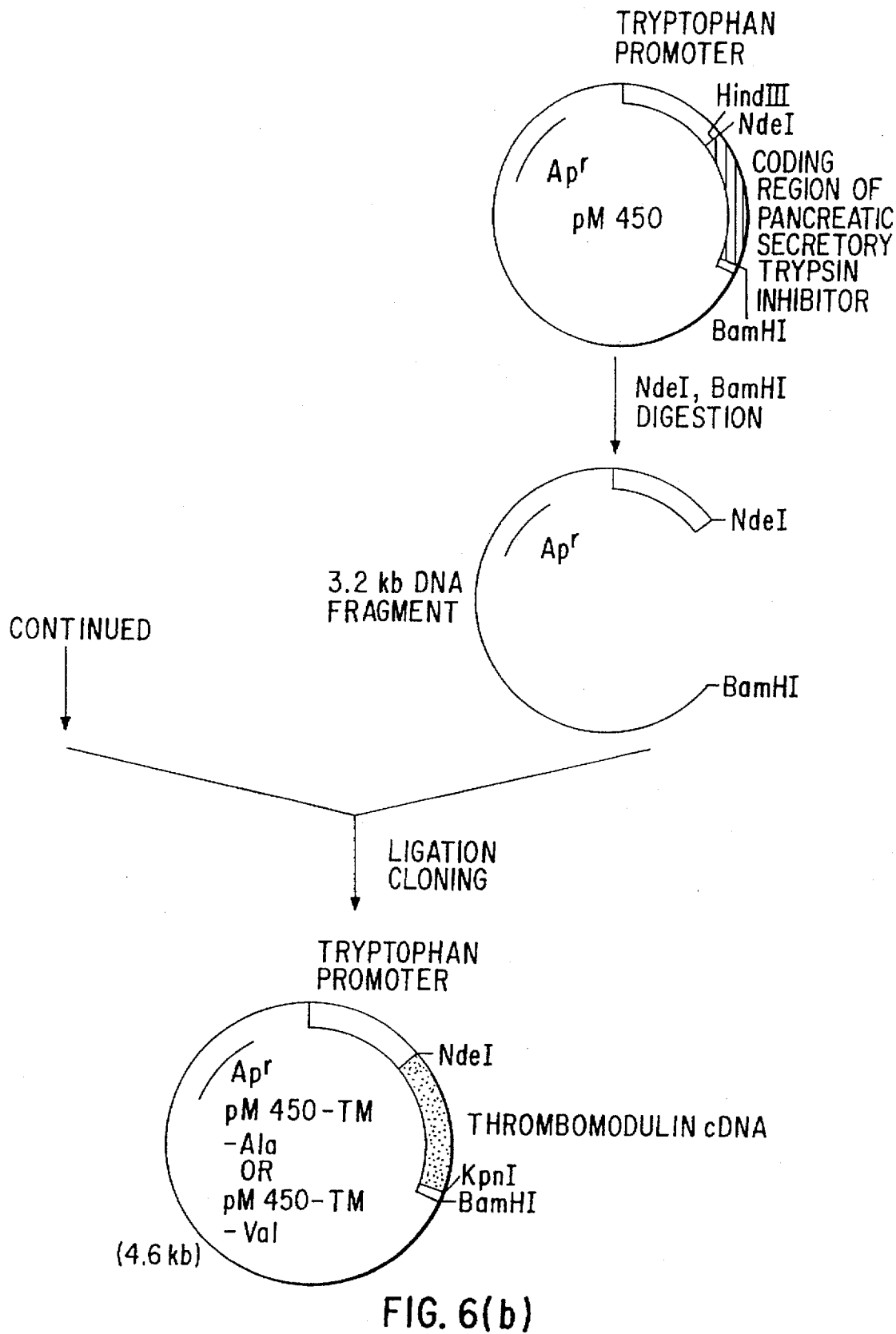
Figure 8:
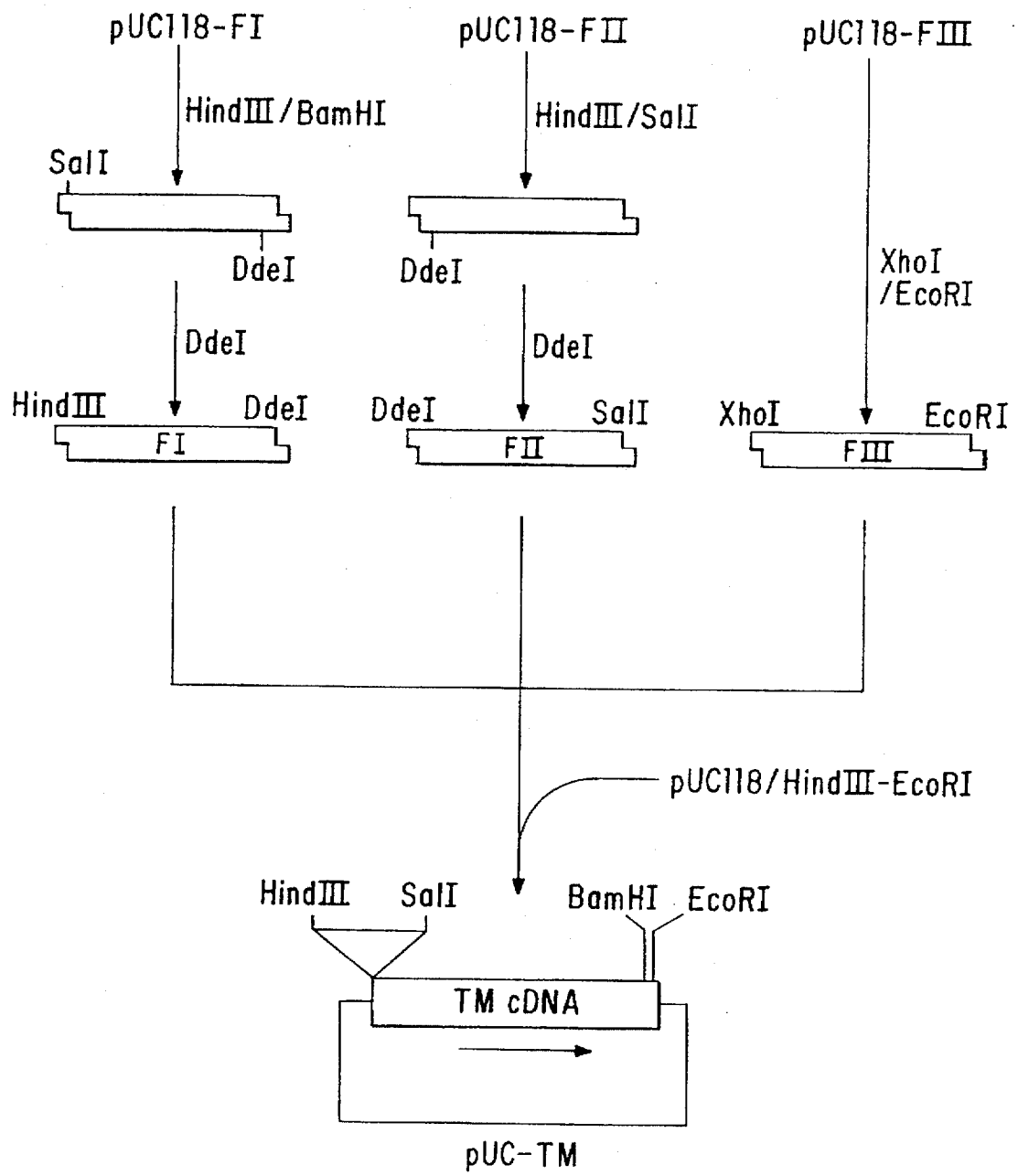
FIG. 8 is a graph showing a procedure for the construction of plasmid pUC-TM containing a DNA fragment which encodes the polypeptide of the present invention.
Figure 10A:
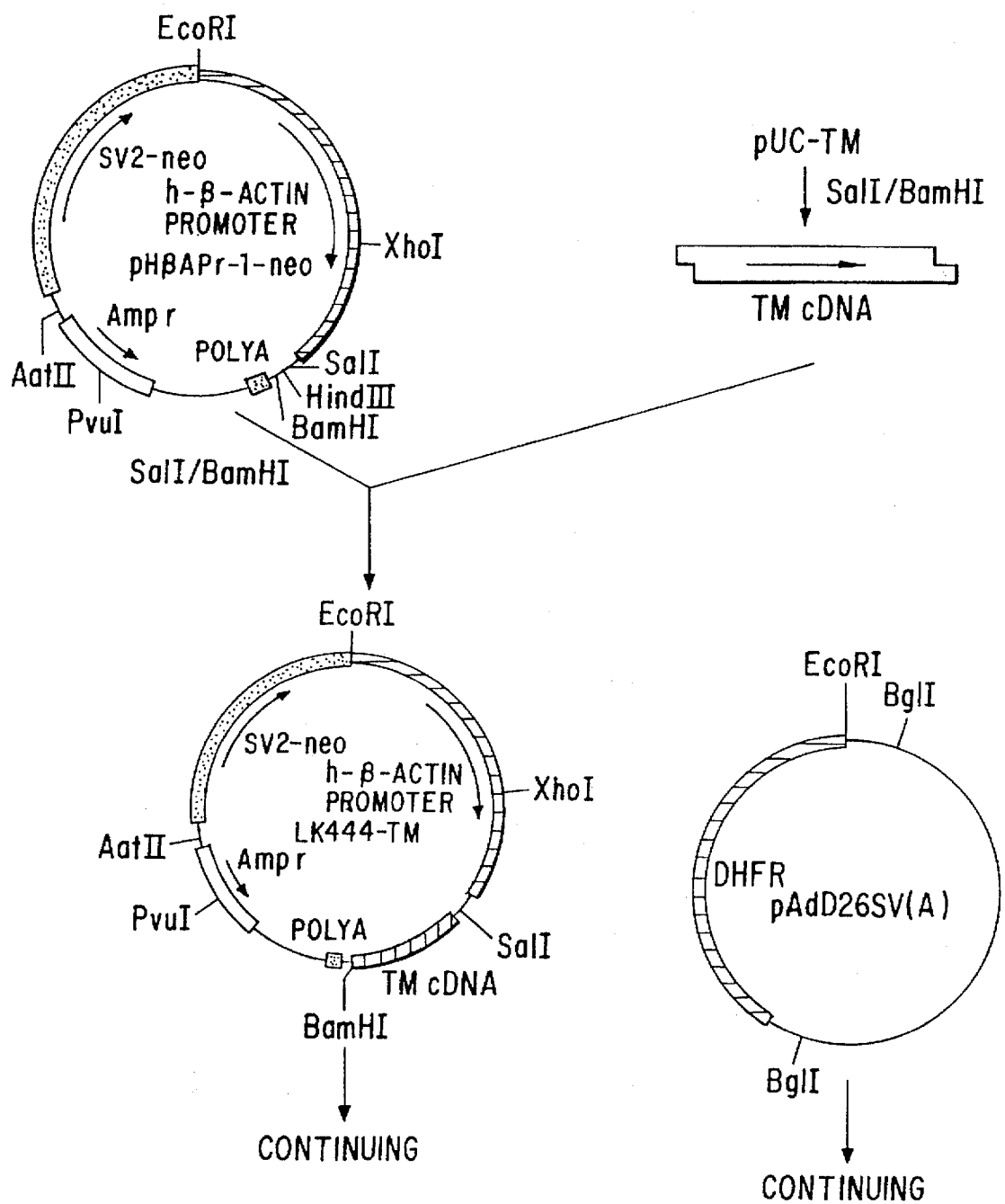
FIG. 10(a) and FIG. 10(b) include a graph showing a procedure for the construction of expression plasmid LK-444-TM-DHFR of the present invention for use in mammalian cells.
Figure 10B:
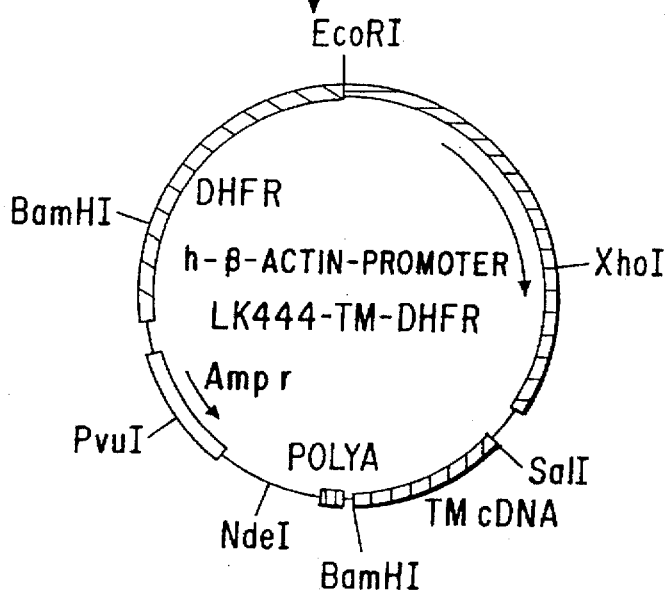
Figure 11A:
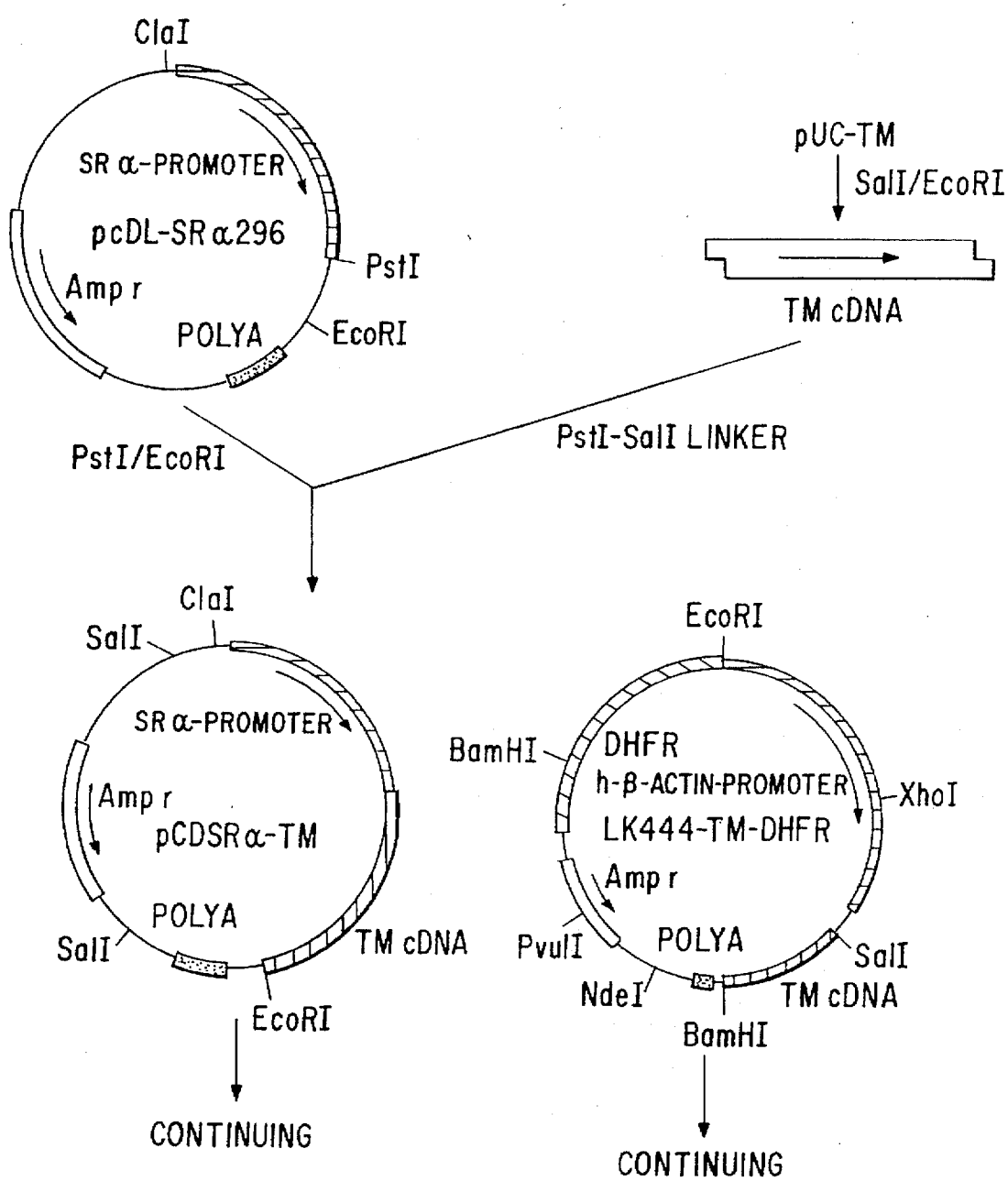
FIG. 11(a) and FIG. 11(b) include a graph showing a procedure for the construction of expression plasmid pCDSR α-TM-DHFR of the present invention for use in mammalian cells.
Figure 11B:
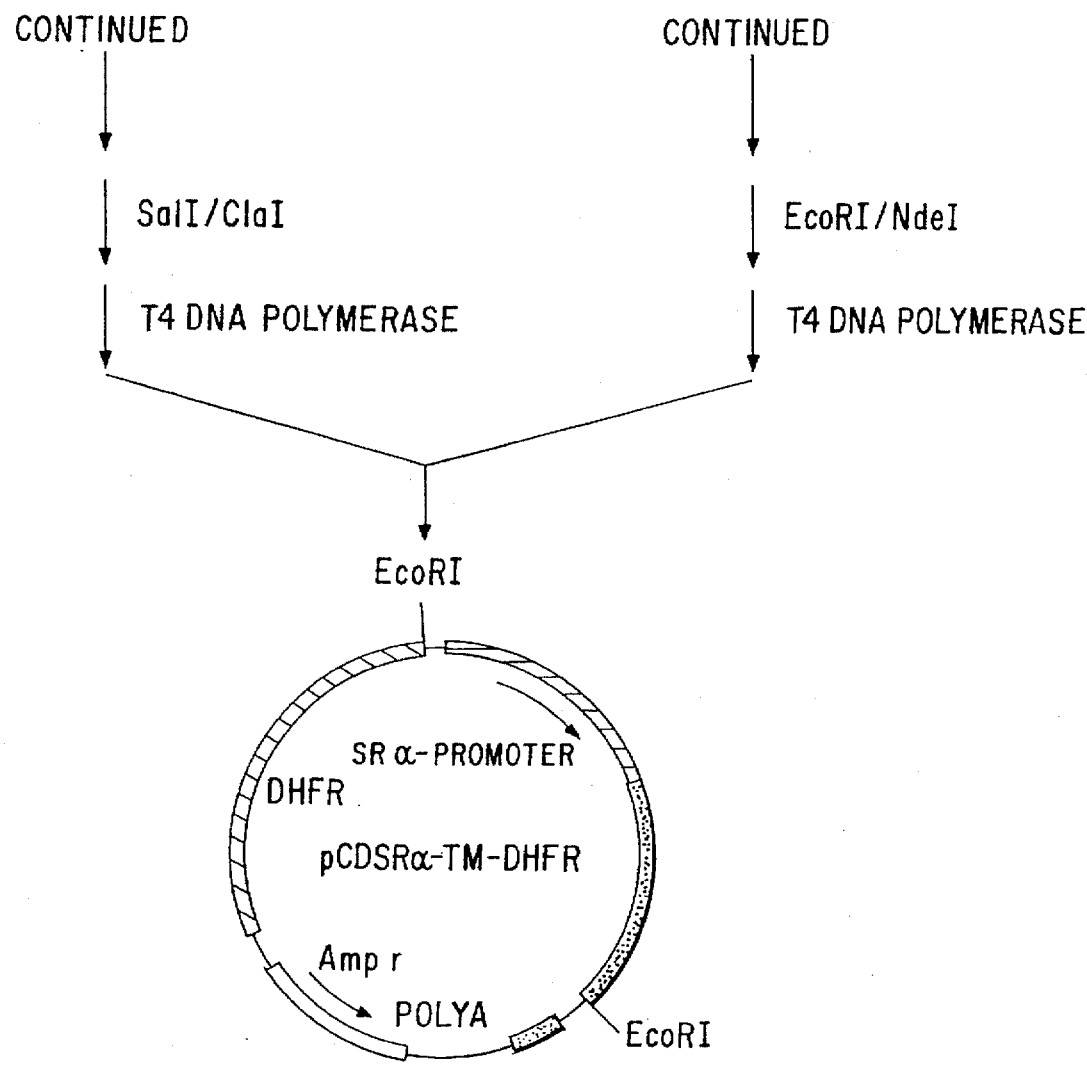
Figure 13A:
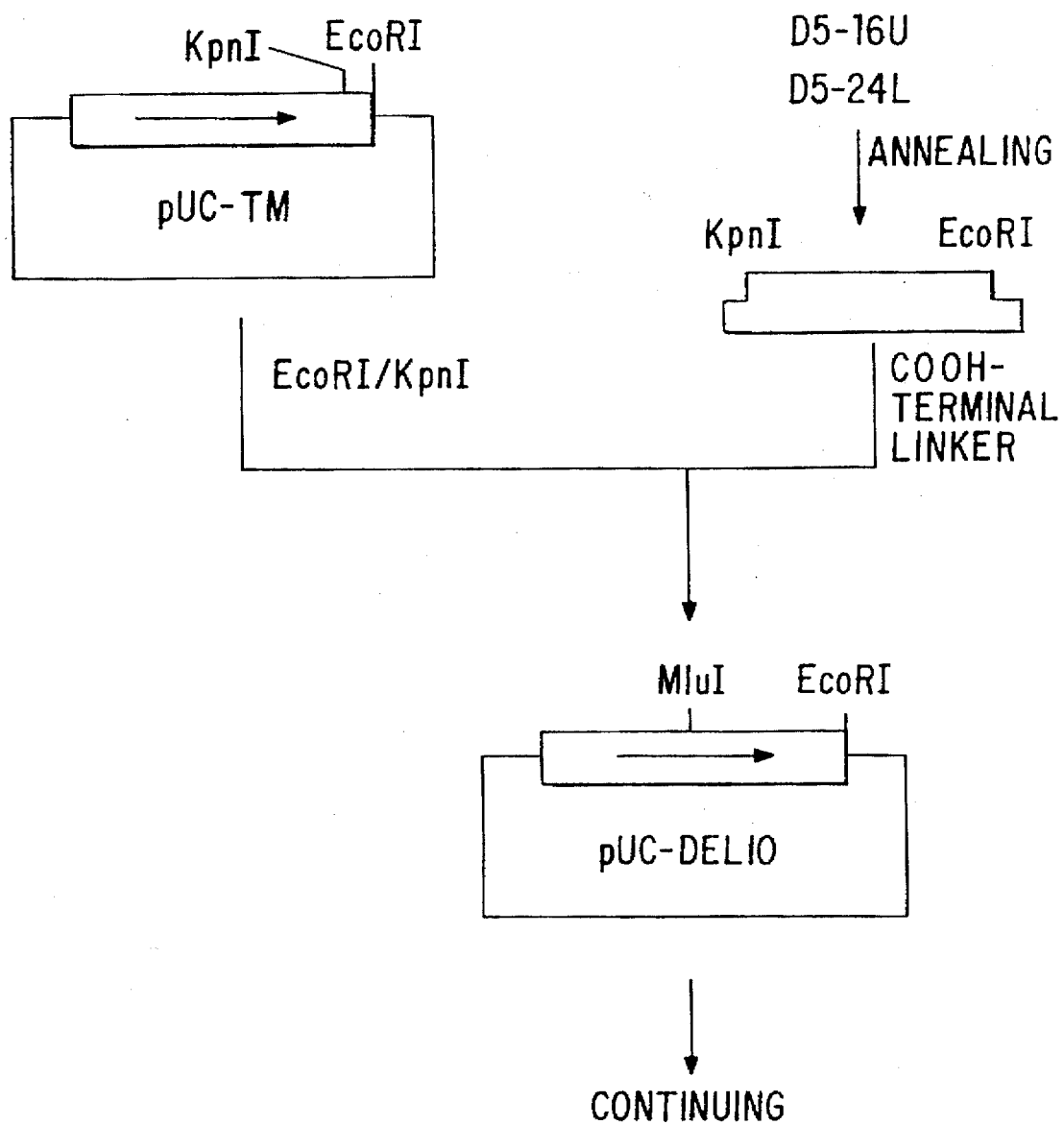
FIG. 13(a) and FIG. 13(b) include a graph showing a procedure for the construction of expression plasmids pCDSR α-DEL10 and pCDSR α-DEL49 of the present invention for use in mammalian cells.
Figure 13B:
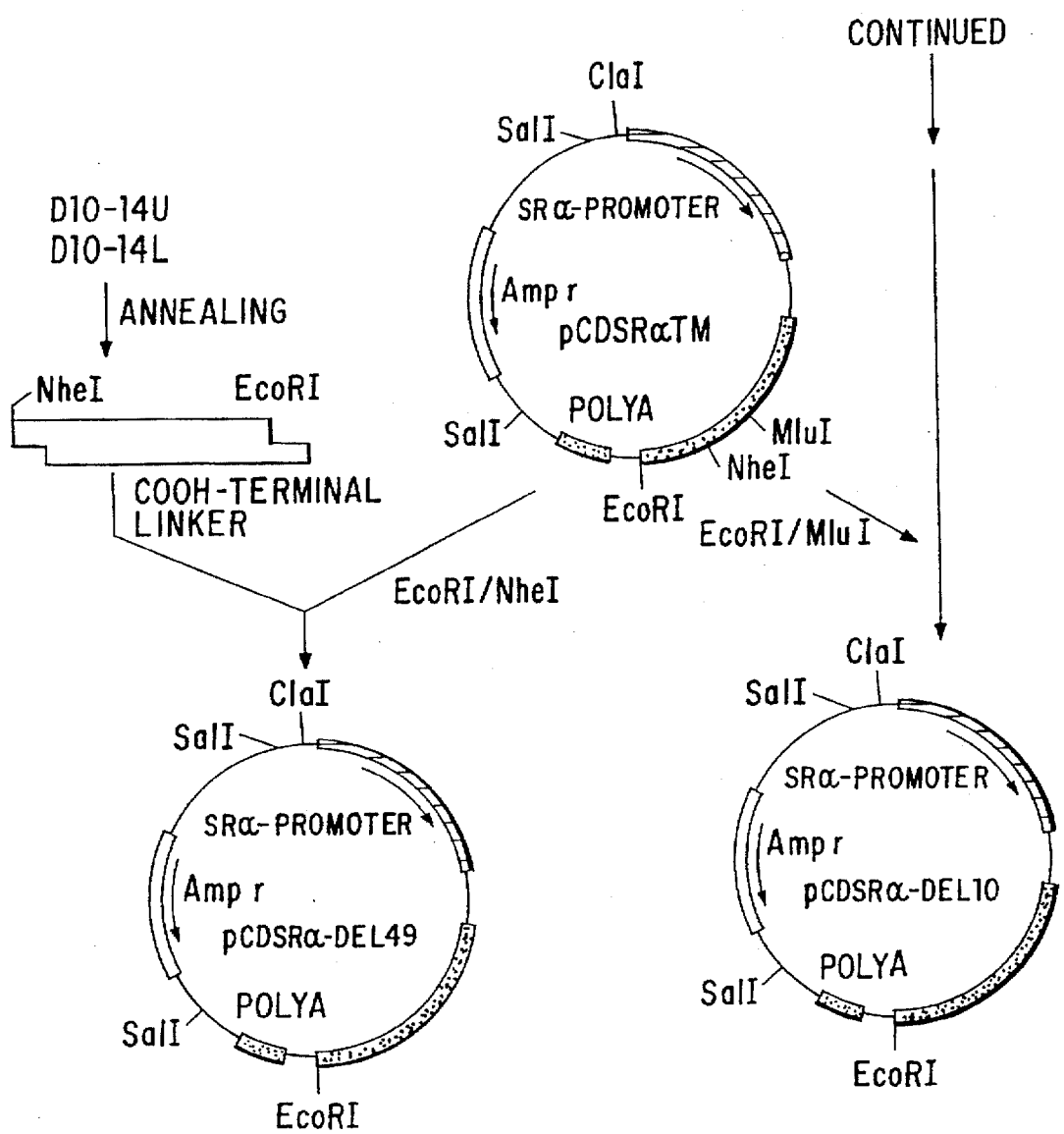

The polypeptide of the present invention imparts an effect of inhibiting both blood coagulation and platelet aggregation because of its function to bind to thrombin and inactivate the activity thereof and, at the same time, exhibits anticoagulant and thrombolytic activities by activating protein C. Because of such effects, it is possible to use the polypeptide for the treatment of a broad range of hypercoagulability-related diseases, based on its thrombus formation inhibiting activity, thrombolytic activity, anti-DIC activity and the like. Especially, reduction of side effects can be expected because of its excellent function to activate protein C.

In addition, the polypeptide of the present invention has been produced for the first time by means of genetic engineering techniques. In consequence, when it is applied to a pharmaceutical drug as an agent for the treatment or prevention of hypercoagulability-related diseases such as thrombosis, DIC and the like, more stronger effect than the prior art counterpart, or similar effect with smaller dose, can be expected, thus rendering possible economical use of the drug with less danger of generating side effects. Also, it is possible to find an entirely new effect such as treatment of a disease which is difficult to cure in the present situation.

Also, the polypeptide of the present invention can be used more safely as a pharmaceutical drug, because it is not necessary to use a surface active agent which is essential for the solubilization of prior art human thrombomodulin extracted from tissues of placenta, the lungs and the like.

In addition to its application to pharmaceutical drugs as described above, the polypeptide of the present invention can also be used for the purpose of preventing blood coagulation, by binding and adsorbing it to the surface of an artificial blood vessel, an artificial organ, a catheter or the like making use of a cross-linking agent or the like.

What is claimed is:

1. A recombinant DNA vector having an insert consisting of the DNA sequence corresponding to SEQ ID NO: 6, wherein (a) at least 1 and no more than 21 coding triplets of nucleotides are deleted from the 5' end of SEQ ID NO:6, (b) at least 1 and no more than 11 triplets of nucleotides are deleted from the 3' end of SEQ ID NO:6, or both (a) and (b).

2. A recombinant DNA vector according to claim 1, selected from the group consisting of SEQ ID NO:7 and SEQ ID NO:8.

3. A plasmid selected from the group consisting of pCDSRα-TM and pCDSRα-TM-DHFR.

4. A host cell transformed with a DNA sequence corresponding to SEQ ID NO:6, wherein (a) at least 1 and no more than 21 coding triplets of nucleotides are deleted from the 5' end of SEQ ID NO:6, (b) at least 1 and no more than 11 triplets of nucleotides are deleted from the 3' end of SEQ NO:6, or both (a) and (b).

5. The host cell of claim 4, which is a prokaryotic host cell.

6. The host cell of claim 4, which is a eukaryotic host cell.

7. The host cell of claim 6, which is a CHO cell.

8. The host cell of claim 6, which is a TMM-B1C.

9. A host cell transformed with a recombinant DNA expression vector having an insert consisting of a DNA sequence corresponding to SEQ ID NO:6, wherein (a) at least 1 and no more than 21 coding triplets of nucleotides are deleted from the 5' end of SEQ ID NO:6, (b) at least 1 and no more than 11 triplets of nucleotides are deleted from the 3' end of SEQ ID NO:6, or both (a) or (b).

10. The host cell of claim 9, which is a prokaryotic host cell.

11. The host cell of claim 9, which is a eukaryotic host cell.

12. The host cell of claim 11, which is a CHO cell.

13. The host cell of claim 11, which is a TMM-B1C.

14. A recombinant DNA vector having one or more inserts, each said insert consisting of the DNA of SEQ ID NO:6, wherein (a) at least 1 and no more than 21 coding triplets of nucleotides are deleted from the 5' end of SEQ ID NO:6, (b) at least 1 and no more than 11 triplets of nucleotides are deleted from the 3' end of SEQ ID NO:6, or both (a) and (b).

15. A host cell transformed with a recombinant DNA expression vector having one or more inserts, each said insert consisting of a DNA sequence corresponding to SEQ ID NO:6, wherein (a) at least 1 and no more than 21 coding triplets of nucleotides are deleted from the 5' end of SEQ ID NO:6, (b) at least 1 and no more than 11 triplets of nucleotides are deleted from the 3' end of SEQ ID NO:6, or both (a) or (b).

* * * * *